United States Patent
Lohse et al.

(10) Patent No.: US 9,970,874 B2
(45) Date of Patent: May 15, 2018

(54) METHODS AND SYSTEMS FOR ANALYZING IMAGES OF SPECIMENS PROCESSED BY A PROGRAMMABLE QUANTITATIVE ASSAY

(75) Inventors: Jesper Lohse, Herlev (DK); Hans Christian Pedersen, Hillerod (DK); Joachim Schmid, Santa Barbara, CA (US); Jeff Caron, Orinda, CA (US); Rohit Jain, Ventura, CA (US); Thomas Briscoe, Fort Collins, CO (US)

(73) Assignee: DAKO DENMARK A/S, Glostrup (DK)

( * ) Notice: Subject to any disclaimer, the term of this patent is extended or adjusted under 35 U.S.C. 154(b) by 1633 days.

(21) Appl. No.: 13/306,470

(22) Filed: Nov. 29, 2011

(65) Prior Publication Data
US 2012/0163681 A1 Jun. 28, 2012

Related U.S. Application Data

(60) Provisional application No. 61/417,821, filed on Nov. 29, 2010.

(51) Int. Cl.
*G06K 9/00* (2006.01)
*G01N 21/64* (2006.01)

(52) U.S. Cl.
CPC ..... *G01N 21/6456* (2013.01); *G01N 21/6428* (2013.01); *G01N 2021/6439* (2013.01)

(58) Field of Classification Search
USPC .......................... 382/133; 436/164, 172, 805
See application file for complete search history.

(56) References Cited

U.S. PATENT DOCUMENTS

| | | | | |
|---|---|---|---|---|
| 4,207,554 A * | 6/1980 | Resnick et al. | 382/133 |
| 5,072,382 A * | 12/1991 | Kamentsky | 382/133 |
| 5,187,066 A | 2/1993 | Becker et al. | |
| 5,268,966 A * | 12/1993 | Kasdan | 382/133 |
| 5,671,290 A * | 9/1997 | Vaidyanathan | 382/133 |
| 5,757,954 A * | 5/1998 | Kuan et al. | 382/133 |
| 6,243,486 B1 * | 6/2001 | Weiss | 382/133 |
| 6,317,511 B1 * | 11/2001 | Horiuchi | 382/133 |
| 6,381,353 B1 * | 4/2002 | Weiss | 382/133 |
| 7,760,927 B2 * | 7/2010 | Gholap et al. | 382/133 |
| 7,813,881 B2 * | 10/2010 | Stein et al. | 702/19 |

(Continued)

FOREIGN PATENT DOCUMENTS

| | | |
|---|---|---|
| CN | 1360211 A | 7/2002 |
| CN | 1945333 A | 4/2007 |
| WO | 2009098079 A1 | 8/2009 |

OTHER PUBLICATIONS

PCT International Preliminary Report on Patentablility, Jun. 4, 2013, p. 1-9.*

(Continued)

*Primary Examiner* — Gandhi Thirugnanam

(57) ABSTRACT

Disclosed are methods and systems for analyzing images of specimens processed by a programmable quantitative assay or more specifically a robust programmable quantitative dot assay, PDQA, that enable specimens to be imaged and assessed across a wide variety of conditions and applications. Specific embodiments directed to immunohistochemical applications provide more quantitative methods of imaging and assessing biological samples including tissue samples.

56 Claims, 47 Drawing Sheets

(56) References Cited

U.S. PATENT DOCUMENTS

| | | | |
|---|---|---|---|
| 2001/0002315 A1* | 5/2001 | Schultz et al. | 436/172 |
| 2002/0037847 A1* | 3/2002 | O'Reilly et al. | 514/12 |
| 2002/0064785 A1* | 5/2002 | Mass | 435/6 |
| 2002/0159625 A1* | 10/2002 | Elling | 382/133 |
| 2003/0021457 A1* | 1/2003 | Kirk et al. | 382/133 |
| 2003/0083465 A1* | 5/2003 | Zimrin et al. | 530/350 |
| 2003/0166261 A1* | 9/2003 | Sompuram et al. | 435/287.2 |
| 2004/0023877 A1* | 2/2004 | O'Reilly et al. | 514/12 |
| 2004/0170325 A1* | 9/2004 | Eichhorn et al. | 382/205 |
| 2004/0253226 A1* | 12/2004 | Holaday et al. | 424/94.64 |
| 2006/0188140 A1* | 8/2006 | Gholap et al. | 382/133 |
| 2006/0246524 A1 | 11/2006 | Bauer et al. | |
| 2008/0076186 A1* | 3/2008 | Denny et al. | 436/161 |
| 2008/0285837 A1* | 11/2008 | Kilpatrick et al. | 382/133 |
| 2009/0163406 A1* | 6/2009 | Kornblum et al. | 514/12 |
| 2009/0166570 A1 | 7/2009 | Honda et al. | |
| 2009/0245598 A1* | 10/2009 | Can | G06T 7/0012 382/128 |
| 2009/0275042 A1* | 11/2009 | Emans et al. | 435/6 |
| 2009/0324546 A1 | 12/2009 | Notka et al. | |
| 2010/0080439 A1* | 4/2010 | Karam et al. | 382/133 |
| 2010/0279301 A1* | 11/2010 | Chinnaiyan et al. | 435/6 |
| 2012/0163681 A1* | 6/2012 | Lohse et al. | 382/128 |
| 2012/0245235 A1* | 9/2012 | Rhodes | 514/789 |
| 2013/0337441 A1* | 12/2013 | Lohse | 435/6.1 |
| 2014/0038169 A1* | 2/2014 | Lohse et al. | 435/5 |

OTHER PUBLICATIONS

Examination Report dated Sep. 1, 2015 for Australian Patent Application No. 2011336707, 4 pages.

Examination Report dated Sep. 16, 2016 for Australian Patent Application No. 2015221546, 5 pages.

Office Action dated Oct. 2, 2017 for Canadian Patent Application No. 2819181, 4 pages.

* cited by examiner

530
↓

| cell line | Her2 IHC Score | PDQA dots / nucleus | receptors / cell (published scatchard plot results) |
|---|---|---|---|
| MDA-231 | 0 | 0.04 | 20,000 |
| MDA-175 | 1+ | 0.20 | 100,000 |
| SK-BR-3 | 3+ | 5.90 | 3,000,000 |

540 → MDA-231
542 → MDA-175
544 → SK-BR-3

PDQA - Programmable Dot Quantitative Assay

| Objective Used | Resolution | Manual Dot Count | Automated Dot Count | % dots identified at lower resolution vs. highest resolution image | image bytes (uncompressed whole slide image) at selected resolution | Number of tiles to be scanned vs. lowest resolution |
|---|---|---|---|---|---|---|
| 40X | Highest = 0.25 μm / px | 18 | 18 | 100.0% | 28,449,622,520 | 64 |
| 20X | Medium = 0.5 μm / px | 18 | 18 | 100.0% | 7,084,905,640 | 16 |
| 10X | Low = 1 μm / px | 18 | 18 | 100.0% | 1,771,226,408 | 4 |
| 4X | Lowest = 2 μm / px | 18 | 17 | 94.4% | 442,806,602 | 1 |

640 → 40X row
642 → 20X row
644 → 10X row
648 → 4X row 650, 655, 660, 665, 670, 675, 680

FIG. 6E

Her2 specimen staining by proximity ligation assay (non-PDQA)

| Objective Used | steps out of focus | Manual blob count | Unadjusted HSI Threshold Automated blob count | % blobs automatic vs. manual at selected focus |
|---|---|---|---|---|
| 20X | -2 (46) | 57 | 12 | 21.1% |
| 20X | -1 (47) | 141 | 41 | 41.4% |
| 20X | 0 (48) | 400 | 144 | 47.7% |
| 20X | 1 (49) | 446 | 168 | 48.6% |
| 20X | 2 (40) | 297 | 126 | 42.4% |

FIG. 8C

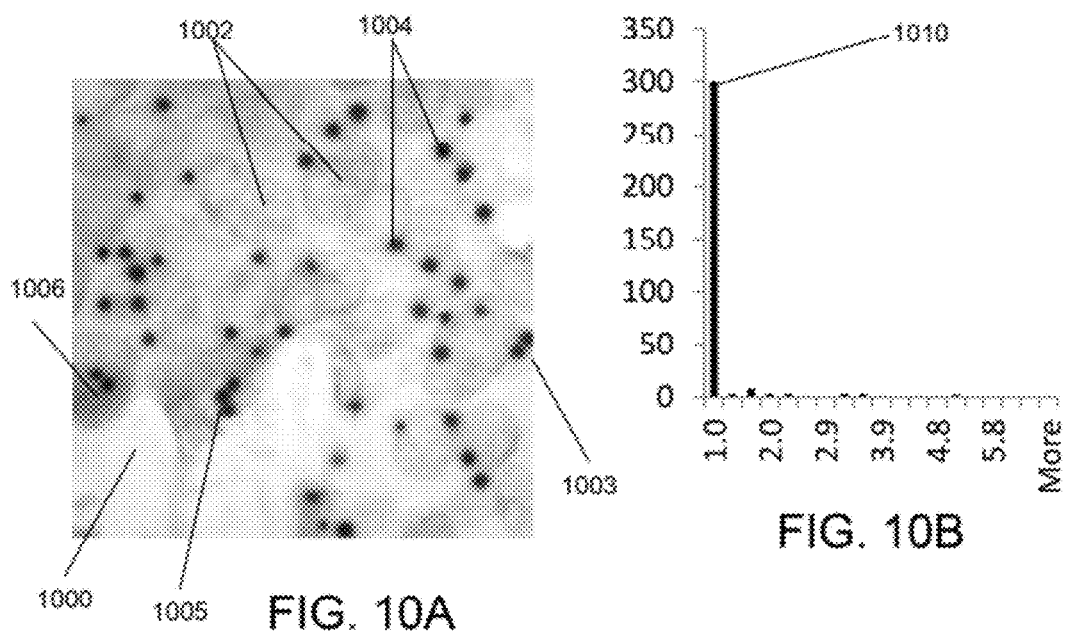
FIG. 10A
FIG. 10B
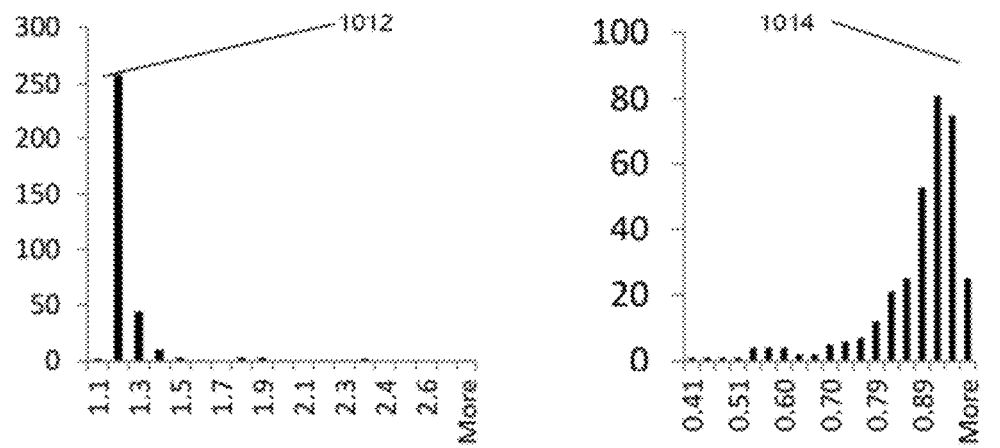
FIG. 10C
FIG. 10D

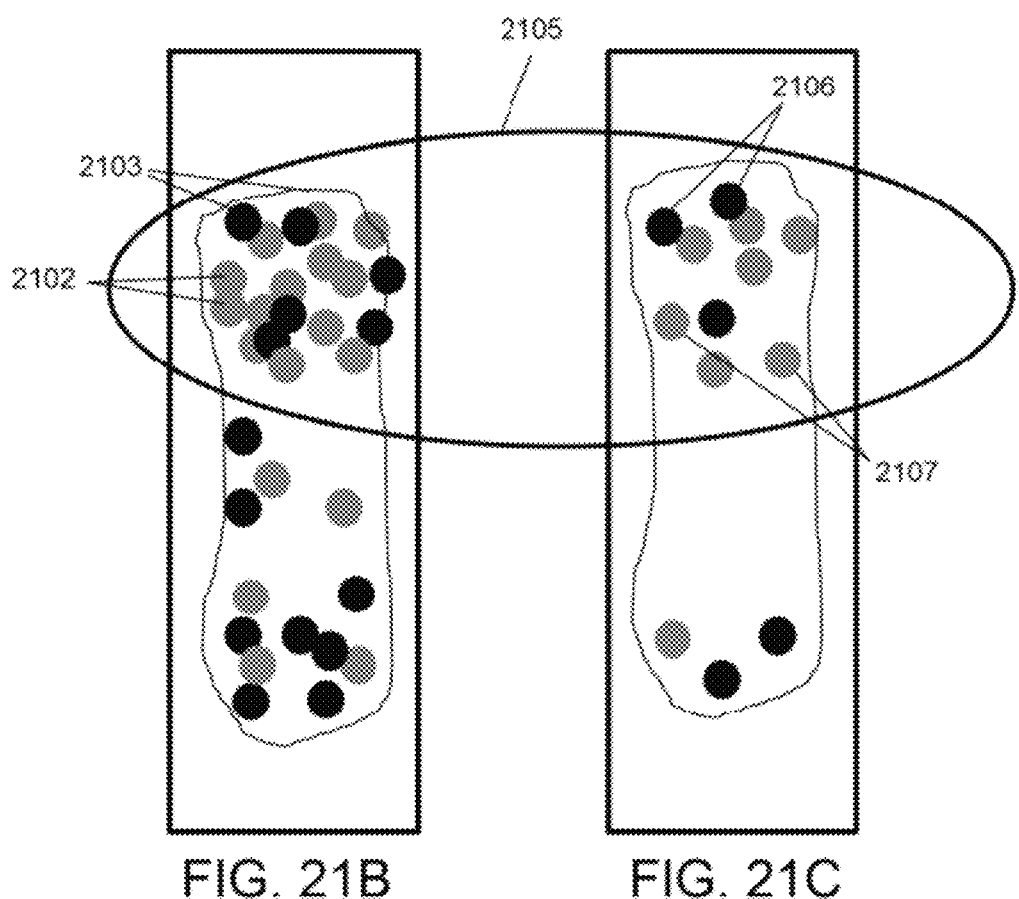

METHODS AND SYSTEMS FOR ANALYZING IMAGES OF SPECIMENS PROCESSED BY A PROGRAMMABLE QUANTITATIVE ASSAY

RELATED APPLICATIONS

This application claims the benefit of priority under 35 U.S.C. § 119(e) of U.S. Provisional Patent Application No. 61/417,821, filed on Nov. 29, 2010, the disclosure of which is incorporated herein by reference.

FIELD OF THE INVENTION

The present disclosure relates to quantitative staining and imaging of specimens and, more particularly, to quantitative staining and imaging of histochemically stained tissue specimens.

BACKGROUND OF THE INVENTION

Advances in analytical science have made it possible to extract a wide variety of information from a biological specimen. For example, it may be possible to assess the health, diagnose a disease state, identify possible future health issues, predict a response to a treatment, and provide information related to the genetic makeup of an individual from which the specimen was obtained.

Histochemical staining has made it possible to highlight morphological features of a specimen and in some cases to detect and visualize the presence of target molecules with a specimen. For example, immunohistochemical staining, also referred to herein as IHC, utilizes antibody-based detection systems to detect and visualize the presence within a specimen of a protein to which an antibody has been developed.

Moreover, advances in digital microscopic imaging have enabled microscopic images to be captured, processed, and analyzed.

However, analysis of histochemical staining has been largely regarded as non-quantitative or semi-quantitative at best. Image analysis of histochemical staining has been utilized in attempts to make the analyses more quantitative. For example, digital image analysis systems may measure the intensity of staining within predetermined thresholds of color. While such systems may assist, for example, in reducing the variation in scoring between different observers, such analysis systems suffer from the fact that the variance of the shape and size of optically discernible objects within the image of the specimen has been as high as the variance of the inherent shape and size of the features present in the specimen prior to staining, which is typically relatively high.

Thus, some conventional image analysis algorithms have avoided attempting to classify objects according to size and shape, and focused primarily on ratios of different color stains within the specimen. Other image analysis algorithms have attempted to use rather complex object recognition techniques, which again have had to deal with the naturally occurring variance of shape and size of features within the specimen.

Therefore, there has been a need to develop methods and systems for imaging specimens that overcome the limitations and disadvantages of conventional assays and imaging systems.

SUMMARY OF THE INVENTION

In the presently disclosed embodiments, several exemplary methods and systems are described that may be used to image and analyze specimens.

One exemplary disclosed embodiment may include a method of optically quantifying expression of at least one target molecule in at least one region of interest of a specimen. The method may include producing optically recognizable dots at sites of the specimen wherein at least one dot corresponds to a single target molecule. The dots may be characterized by in-situ programmable features of size and shape and at least one additional programmable optical feature, and the number of dots produced at the sites within a given region may be representative of a fractional sub-population of a total population of target molecules within that region. The method may further include imaging the specimen, selecting at least one region of interest within the image, recognizing at least one dot within the at least one region of interest, and quantifying the dots within the at least one region of interest.

In another exemplary embodiment of the disclosure, a system for optically quantifying expression of at least one target molecule in at least one region of interest in a specimen may include a first kit for detecting a fractional sub-population of the at least one target molecule in the specimen and a second kit for producing optically recognizable dots at sites of the specimen wherein at least one dot corresponds to a single target molecule. The dots may be characterized by in-situ programmable features of size and shape and at least one additional programmable optical feature. The number of dots produced at the sites within a given region may be representative of a fractional sub-population of a total population of target molecules within that region. Such a system may also include a stainer adapted to execute a staining protocol using the first and second kits, an imager adapted to image the specimen, and a processor configured to recognize at least one dot within the at least one region of interest and quantify the dots within the at least one region of interest.

In yet another exemplary embodiment, a method of optically quantifying expression of at least one target molecule in at least one region of interest in a specimen may include producing optically recognizable dots at sites of the specimen. At least one dot may correspond to a single target molecule. The dots may be characterized by in-situ programmable features of size and shape and at least one additional programmable optical feature. The number of dots produced at the sites within a given region may be representative of a fractional sub-population of a total population of target molecules within that region. Each dot may be representative of a predetermined number of target molecules to within predetermined statistical limits. The method may further include imaging the specimen, selecting the at least one region of interest within the image, recognizing at least one dot within the at least one region of interest, and quantifying the dots within the at least one region of interest.

In a further embodiment, a system for optically quantifying expression of at least one target molecule in at least one region of interest in a specimen may include a first kit for detecting a fractional sub-population of the at least one target molecule in the specimen and a second kit for producing optically recognizable dots at sites of the specimen wherein at least one dot corresponds to a single target molecule. The dots may be characterized by in-situ programmable features of size and shape and at least one additional programmable optical feature. The number of dots produced at the sites within a given region may be representative of a fractional sub-population of a total population of the at least one target molecule within that region. Each dot may be representative of a predetermined number of target molecules to within predetermined statistical limits.

The system may further include a stainer adapted to execute a staining protocol using the first and second kits, an imager adapted to image the specimen, and a processor configured to recognize at least one dot within the at least one region of interest and quantify the dots within the at least one region of interest.

In still another embodiment, a method of optically quantifying expression of at least one target molecule in at least one region of interest in a specimen may include imaging the specimen with an imager, selecting at least one region of interest within the image and recognizing at least one optically recognizable dot at sites of the specimen within the at least one region of interest wherein the at least one dot corresponds to a single target molecule. The dots may be characterized by in-situ programmable features of size and shape and at least one additional programmable optical feature. The number of dots recognized at the sites within a given region may be representative of a fractional sub-population of a total population of target molecules within that region. The dots may be representative of a predetermined number of target molecules to within predetermined statistical limits. The method may further include performing at least one image analysis step based on the at least one recognized dot.

In yet another exemplary embodiment, a system for optically quantifying the expression of at least one target molecule in at least one region of interest in a specimen may include an imager adapted to image the specimen, and at least one processor configured to select at least one region of interest within the image, recognize at least one optically recognizable dot at sites of the specimen within the at least one region of interest wherein at least one dot corresponds to a single target molecule. The dots may be characterized by in-situ programmable features of size and shape and at least one additional programmable optical feature. The number of dots recognized at the sites within a given region may be representative of a fractional sub-population of a total population of target molecules within that region. Each dot may be representative of a predetermined number of target molecules to within predetermined statistical limits. The processor may be further configured to perform at least one image analysis step based on the at least one recognized dot.

In an additional embodiment, a method of optically quantifying multiplexed diagnostic indicators in a tissue specimen may include producing a first multiplexed diagnostic indicator within at least one region of interest in a tissue specimen. The first multiplexed diagnostic indicator may include a first set of optically recognizable dots at sites of the specimen wherein at least one dot corresponds to a single first target molecule. The first set of dots may be characterized by in-situ programmable features of size and shape and at least one additional programmable optical feature. The first set of dots produced at the sites within a given region may be representative of a fractional sub-population of a total population of first target molecules within that region. The method may further include producing a second multiplexed diagnostic indicator within the at least one region of interest, imaging the specimen, and assessing the first multiplexed diagnostic indicator and the second multiplexed diagnostic indicator. Assessing the first multiplexed diagnostic indicator may include recognizing at least one of the first set of dots within the at least one region of interest, and quantifying the first set of dots within the at least one region of interest. The method may further include determining an overall diagnostic assessment of the tissue specimen based at least in part on first and second multiplexed diagnostic indicator assessments.

BRIEF DESCRIPTION OF THE DRAWINGS

FIGS. 5AA-5CC are images of control cell lines with known cancer states processed by a programmable quantitative assay.

FIG. 5D shows a table showing concordance of results from image analysis of a control cell lines processed by a programmable quantitative assay.

FIG. 6E shows a table with substantially matching results from image analysis of the field of view in the images taken at different resolutions as depicted in FIGS. 6A-6D.

FIG. 8C shows a table comparing results of an image taken in focus of a slide with control cell lines processed by a proximity ligation assay with blobs identified and annotated by manual counting and by image analysis software

FIG. 10A depicts an image of a tissue specimen processed by a programmable quantitative assay.

FIG. 10B depicts a histogram of object elongation of dots within the image shown in FIG. 10A.

FIG. 10C depicts a histogram of object compactness of dots within the image shown in FIG. 10A.

FIG. 10D depicts a histogram of object min to max feret ratio of dots within the image shown in FIG. 10A.

FIG. 21B illustrates a ratiometric embodiment of method of analyzing an image with target dots and reference dots for robustness and quality control under normal pre-analytical processing conditions.

FIG. 21C illustrates a ratiometric embodiment of a method of analyzing an image with target dots and reference dots for robustness and quality control under altered pre-analytical processing conditions that suppress the availability of targets and references.

DETAILED DESCRIPTION OF THE EMBODIMENTS

Definitions

Figure 1:
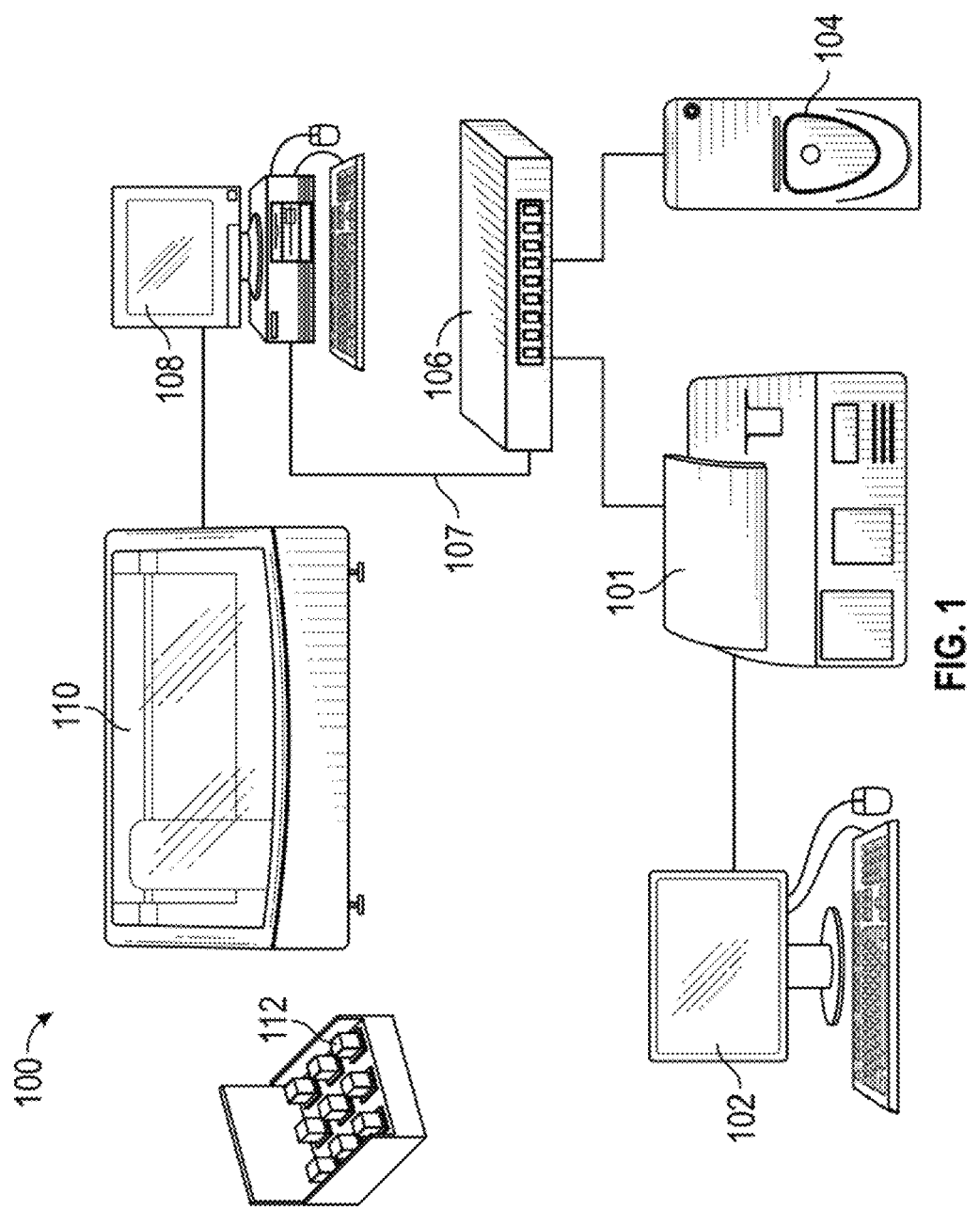
FIG. 1 illustrates a system and kits for processing a specimen including a microscope slide scanner.

Programmable, as used herein, means changeable or variable to produce a predetermined set or range of results in response to intentional variation of chemical reaction conditions including chemical components, temperature, time, concentrations, chemical reactions, immunochemical reactions, etc.

Quantitative, as used herein, refers to an assay or an image including measurable data. For example, an image may include a number of discrete objects, and such objects may be measured by counting, measuring their shape or size, measuring their frequency of occurrence over an area of the image, and any other means of applying an objective numerical classification to the data.

Quantifying, as used herein, means to measure or determine the quantity of; to express as a quantity, or in quantitative terms. Quantifying, may include, for example, counting, measuring width, length, diameter, and area, measuring shape, calculating density, calculating frequency, calculating distances, and performing any other quantitative measurement or determination consistent with the disclosure.

Imaging, as used, herein refers to viewing or capturing an image by optical means including brightfield microscopy, fluorescent microscopy, holographic imaging, photography, phase holographic imaging, phase contrast microscopy, confocal microscopy, 3D microscopy, deconvolution microscopy. Imager, as used herein, refers to any system or apparatus adapted for imaging.

Assess, as used, means to evaluate, to estimate (the quality, value, or extent of), to gauge, to score or judge. Assessing the expression of a target molecule within a specimen or regions of interest within a specimen may involve generating or producing a score. The score may be, for example, an absolute target expression level, i.e., a target expression score that is proportional to and representative of the total number of target molecules within the specimen as opposed to a relative target expression level. Assessing may also include generating a clinically meaningful composite score, related to a conventional pathology score such as an Allred score.

Localized, as used herein, means fixed in a particular part (of a specimen); gathered or concentrated into one point or part, occurring in, or restricted to, some particular part or parts of a specimen. Localized refers to objects and features found within a sub region of a specimen image or region of interest of a specimen image. For example, a localized expression level may refer to an expression level that characterizes the sub region.

In-situ, means occurring at or near the environment of the specimen.

Optically recognizable, as used herein, means detectable or recognizable based on optical features. Optically recognizable may refer to features in an image captured by optical means, or may refer to features detectable or recognizable by the human eye, with or without vision aids.

Optical feature, as used herein, refers to a feature that is discernable by optical means including brightfield microscopy, fluorescent microscopy, holographic imaging, photography, phase holographic imaging, phase contrast microscopy, confocal microscopy, 3D microscopy, deconvolution microscopy, and human vision.

Optically neutral result, as used herein, refers to a result which is not an optical feature.

Dot, as used herein, refers to an optically recognizable object having a substantially round shape including a circle, sphere, clipped circle, or clipped sphere.

Partial dot, as used herein, refers to an optically recognizable object having a shape that is a portion of a substantially round shape including a circle or sphere. A partial dot may include an arc, a clipped circle, or a clipped sphere.

Dot cluster, as used herein, refers to an optically recognizable object comprised of at least partially overlapping dots.

As used herein, the word "target" refers to an object of interest that may be present in a sample and that can be characterized by particular physical and/or functional features. Target molecule, as used herein, may refer to target constituted by a molecule of interest. In the context of the disclosure, the terms "target" and "target molecule" may relate to an entire pool of substantially identical entities or molecules, or may relate to a single entity or molecule.

Sites, as used herein, are the locations of an immobilized target molecule, for example, epitopes, antigens, etc within the specimen to which a binding agent will bind. A single unit of a target molecule bound (directly or indirectly) to a binding agent comprising, may constitute a single target site of the invention. Whether a dot corresponds to a single target molecule can be established by showing a substantially linear correlation between the number of dots and the quantity of target molecules.

The term "binding agent," as used herein, means a molecule that is capable of directly or indirectly specifically binding to a single unit of a target molecule, e.g. an individual molecule of a target protein. Binding agents may include a detectable label, e.g. a fluorescent substance, hapten, enzyme, etc. For example, a binding agent may include an enzyme label that, when exposed to an appropriate substrate, causes a detectable precipitate to form at the site of the enzyme label. Throughout this disclosure, any embodiments that may contemplate the use of a particular label, such as an enzyme, should be understood to contemplate the use of any other appropriate label. Additional examples of suitable labels are described in the Additional Examples and Embodiments section.

Substantially, as used herein, means by an amount greater than that which would typically occur as a result of unintended variances in the chemical process, temperature, etc.

Blob, as used herein, is defined as a group of connected object pixels, where an object pixel is any pixel with a nonzero weight.

As used herein, the term "processor" may include an electric circuit that performs a logic operation on an input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. A processor may be configured to perform an action if it is provided with access to, is programmed with, includes, or is otherwise made capable carrying out instructions for performing the action. A processor may be provided with such instructions either directly through information permanently or temporarily maintained in the processor, or through instructions accessed by or provided to the processor. Instructions provided to the processor may be provided in the form of a computer program comprising instructions tangibly embodied on an information carrier, e.g., in a machine-readable storage device, or any tangible computer-readable medium. A computer program may be written in any form of programming language, including compiled or interpreted languages, and it can be deployed in any form, including as a standalone program or as one or more modules, components, subroutines, or other unit suitable for use in a computing environment. The at least one processor may include specialized hardware, general hardware, or a combination of both to execute related instructions. The processor may also include an integrated communications interface, or a communications interface may be included separate and apart from the processor. The at least one processor may be configured to perform a specified function through a connection to a memory location or storage device in which instructions to perform that function are stored.

The foregoing definitions are not intended to limit the scope of the defined terms, but only to provide some exemplary possibilities for the defined terms. Additional examples and embodiments for the defined terms may be found in the Additional Examples and Embodiments section of the disclosure.

DETAILED DESCRIPTION OF THE DRAWINGS

Reference will now be made in detail to the invention, examples of which are illustrated in the accompanying drawings. The implementations set forth in the following description do not represent all implementations consistent with the claimed invention. Instead, they are merely some examples consistent with certain embodiments of the invention.

Systems and methods consistent with the invention may determine performance data associated with one or more aspects of a pathology laboratory handling one or more specimens. As used herein, the term "specimen" broadly refers to any material or piece of material obtained for the purpose of performing an operation in a laboratory. For example, the laboratory may receive a specimen removed from a living being and prepare the specimen for analysis, testing, and/or storage. Exemplary types of specimens include tissue or other biologic samples taken from an animal or human. Additionally, specimens may include other types of samples as further described in the Additional Examples and Embodiments section of the disclosure. As used herein, the word "slides" may refer to slides with specimen mounted thereupon and may include any type of mounting media, coverslips, and any other support suitable for carrying a specimen.

FIG. 1 illustrates a system 100 and kits 112 for processing a specimen. System 100 may be used for producing images of specimens processed by a programmable dot quantitative assay. Exemplary embodiments of kits 112 comprising a programmable dot quantitative assay are described in the Additional Examples and Embodiments section of this document.

Kits 112 may include reagents for producing optically recognizable dots at sites of single detected target molecules. The dots are characterized by a plurality of programmable optical features, for example, size, shape, color, hue, saturation, intensity, sharpness, phase shift, concentric-ringedness, sphericity, area, perimeter, length, width, orientation, axial ratio, feret diameter, elongation, roundness, circularity, eccentricity, light diffraction, focus, fluorescence, and compactness.

Many specimens such as for example, human cells, include hundreds of thousands of protein molecules of different types per cell. In embodiments of the invention, programmable dots may be produced at the sites of a fractional sub-population of a total population of target molecules. The assay may be programmed to have a dot production rate such that each dot may represent a single molecule, hundreds or thousands of detected molecules, or even more.

Because embodiments of the programmable dot quantitative assay have programmable optical features such as size and shape and other features such as color, it is possible in some cases to detect desired programmable optical features and even assess regional target molecule expression within a specimen by use of a conventional microscope slide scanners such as scanner 101; however low cost microscopes or other optical detection systems or even human vision may be sufficient to detect optical features of specimens stained by a programmable quantitative dot assay.

Moreover, the processing of specimens may be done using the same types of equipment and processes used to process conventionally stained immunohistochemistry ("IHC") slides, slides stained by hematoxylin and eosin, also referred to herein as H&E slides, or any type of specimen mounted on a slide or any type of specimen carrier. Stainer 110 may be an autostainer which automatically processes slides. Stainer 110 may connect to a stainer network 107 which also may connect to a workstation 108 which may be a server or a client or a combined client/server. Stainer network 107 may connect via networking hardware 106 to slide scanner 101 which may have a viewing terminal 102 co-located with scanner 101 or located remotely. Any of the network connections may comprise local or wide area connections including the internet or other public networks. Image storage and processing hardware may be integrated within scanner 101 or may be a separate workstation 104.

Figure 2A:
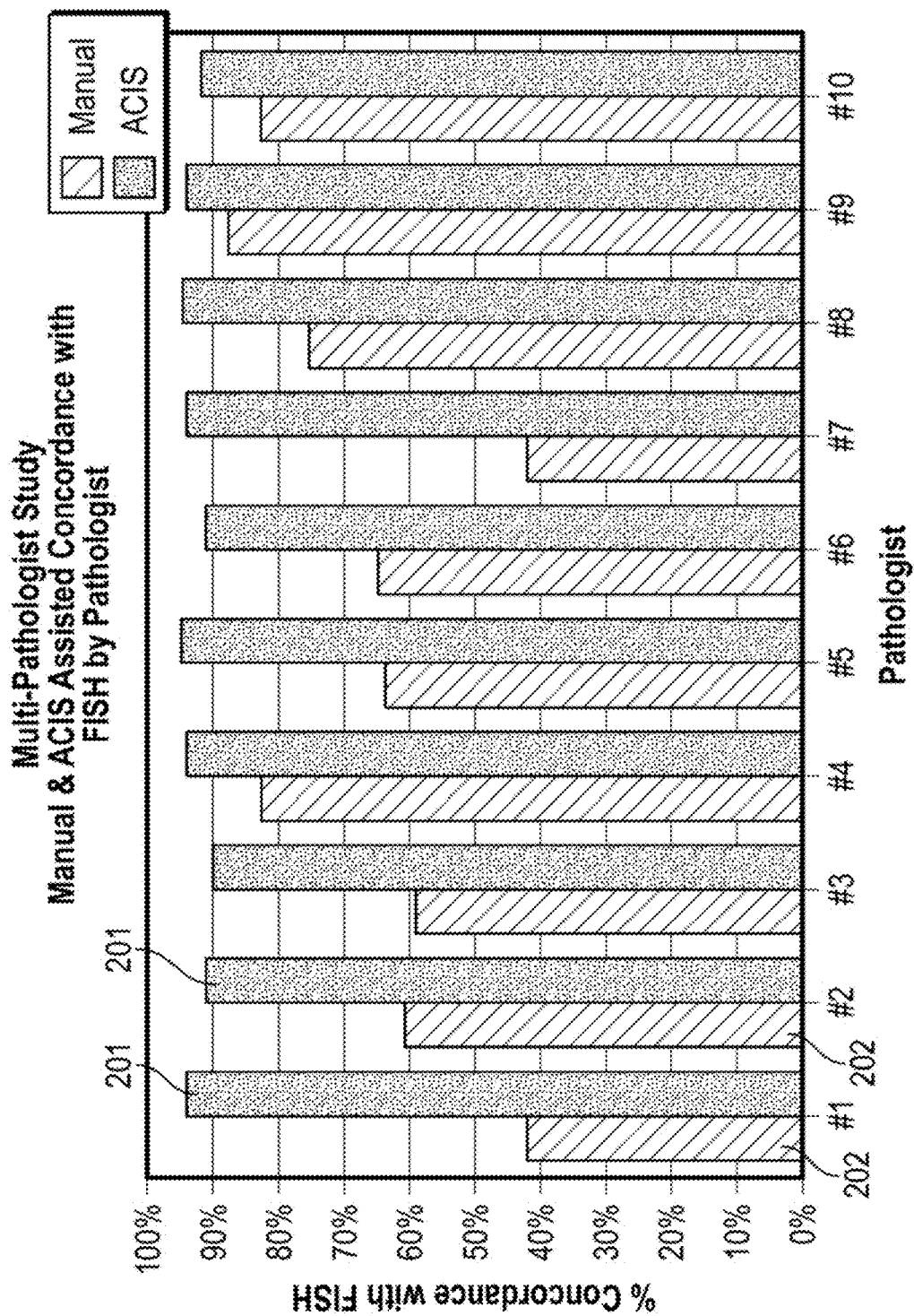
FIG. 2A shows a chart comparing results for manual and automated image analysis of scoring specimens stained by conventional staining.

FIG. 2A shows a chart comparing results for manual and automated image analysis of scoring specimens stained by conventional staining. Concordance of manually assessed IHC staining 202 with fluorescent in situ hybridization generally varied from about 60% to greater than 90%. Use of an automated cellular imaging system and accompanying algorithms, also referred to as ACIS, helped improve concordance across all participating pathologists.

Figure 2C:
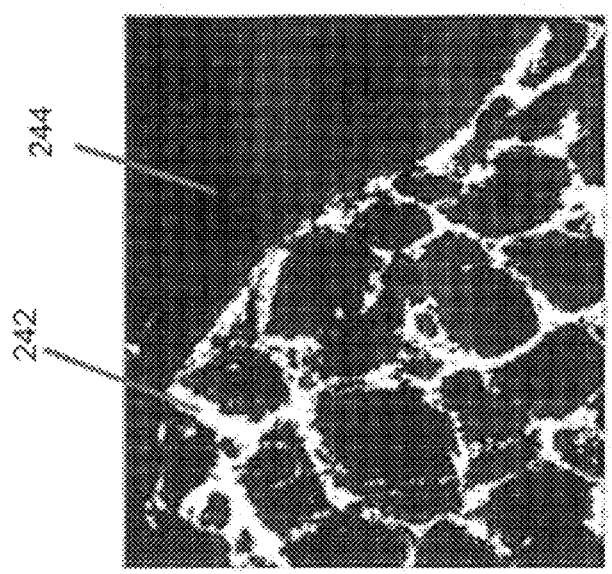
FIG. 2C is a processed image showing brown stained tissue as white pixels and background as black pixels.
Figure 2B:
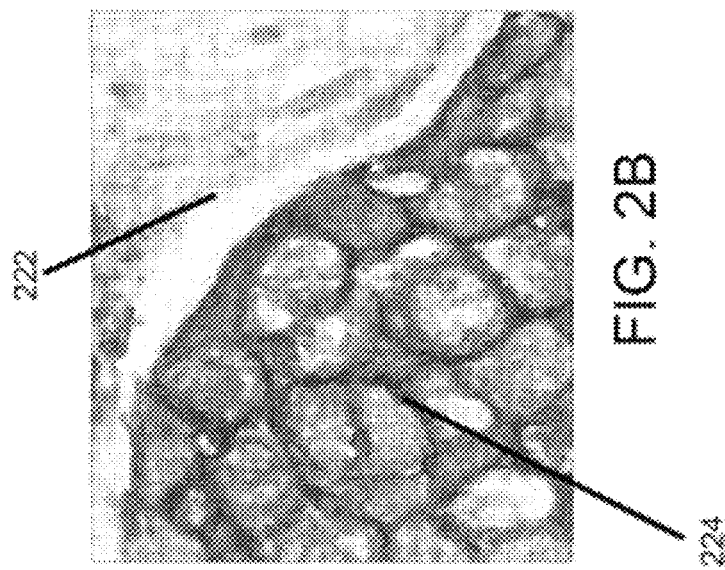
FIG. 2B is an image of tissue stained using conventional immunohistochemistry.

FIG. 2B is an image of tissue stained using conventional immunohistochemistry. As an example, manual assessment or scoring of Her2 expression of HER2 may be assessed as follows: 0 representing normal levels of Her2 is assessed for specimens having membrane staining in <10% of tumor cells; 1+, faint or incomplete membrane staining in >10% of cells; 2+, weak or moderate complete or incomplete staining in >10% of cells; 3+, strong complete membrane staining in >10% of cells. Tumors scored as 3+ are regarded as clearly HER2-positive cases; tumors scored as 0/1+ may be designated as HER2-negative cases; borderline cases (2+) may require further investigation by fluorescence in situ hybridization to assess whether they show gene amplification. Pixels corresponding to open spaces within the specimen or to connective tissue are regarded as background 222. Where HER2 is strongly over expressed, pixels corresponding to darkly stained tissue cell membranes 224 can be seen.

FIG. 2C is a processed image generated from FIG. 2B showing an example where the image has been segmented into brown stained tissue, represented as white pixels 242, and all other pixels are regarded as background which is represented as black pixels 244.

Figure 3A:
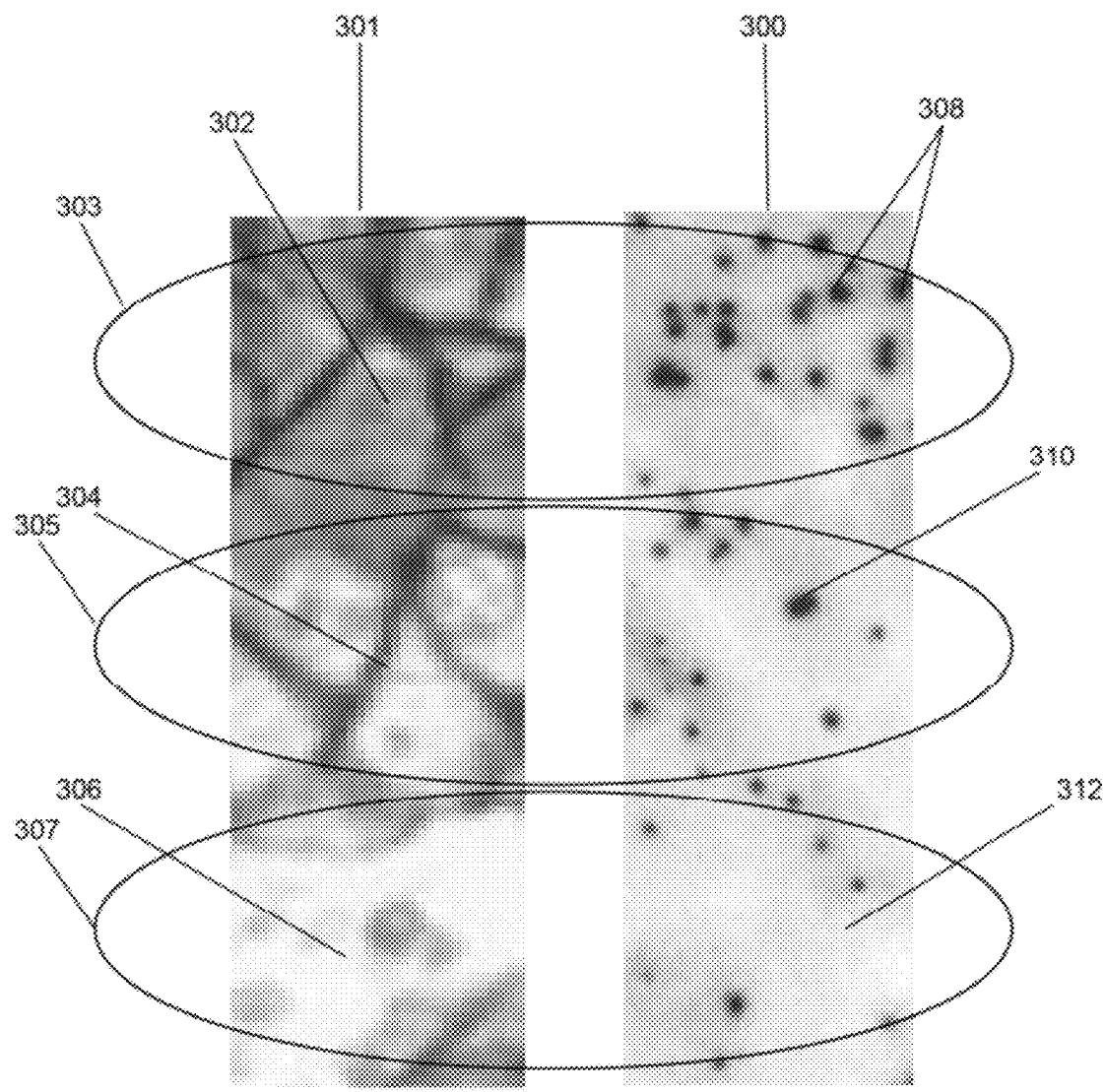
FIG. 3A is a representation of specimen staining by conventional immunohistochemistry assay (left panel) and specimen staining by a programmable dot quantitative assay (right panel) that shows how each assay appears in regions with different levels of target expression.

FIG. 3A is a representation of an image 301 of specimen staining by a conventional immunohistochemistry assay, for example as described above with respect to Her2 IHC staining, and an image 300 of specimen staining by a programmable dot quantitative assay. The Additional Examples and Embodiments section describes chemical compositions, protocols and methods for producing and utilizing some embodiments of a programmable dot quantitative assay.

For both images 301 and 300, elliptical region 303 encompasses a relatively high target expression region, elliptical region 305 encompasses a mid-level target expression region, and elliptical region 307 encompasses a relatively low target expression region. Image analysis of conventional image 301 may be typically performed manually or digitally by assessing the intensity and area of the staining. For example, within region 303 for conventional image 301, high staining intensity, i.e., dark staining such as indicated at area 302, is indicative of the higher target expression levels. Within region 305 for conventional image 301, dark staining intensity over a partial area, such as area 304, is indicative of mid-level target expression within the area. Within region 307, moderate staining over a small area 306 is indicative of low target expression levels with the region.

In one embodiment of the invention, a quantitative image 300 of a specimen processed by a programmable quantitative assay is shown. The programmable quantitative assay has produced a quantitative image 300, which has a large number of dots 308 within region 303. The image is quantitative in that prior to imaging, the high target expression levels within region 303 of image 300 have been effectively converted to discrete quantitative objects, i.e., dots which can be imaged, recognized, and classified, to assess the regional level of target molecules within the specimen. Dots 310 in region 305 of image 300 are fewer and more disperse, indicating a mid-level regional target expression level. A large open area 312 within region 307 of image 300, where relatively few dots have been produced and where the dots are somewhat scattered, is indicative of a lower target molecule expression level.

Figure 3B:
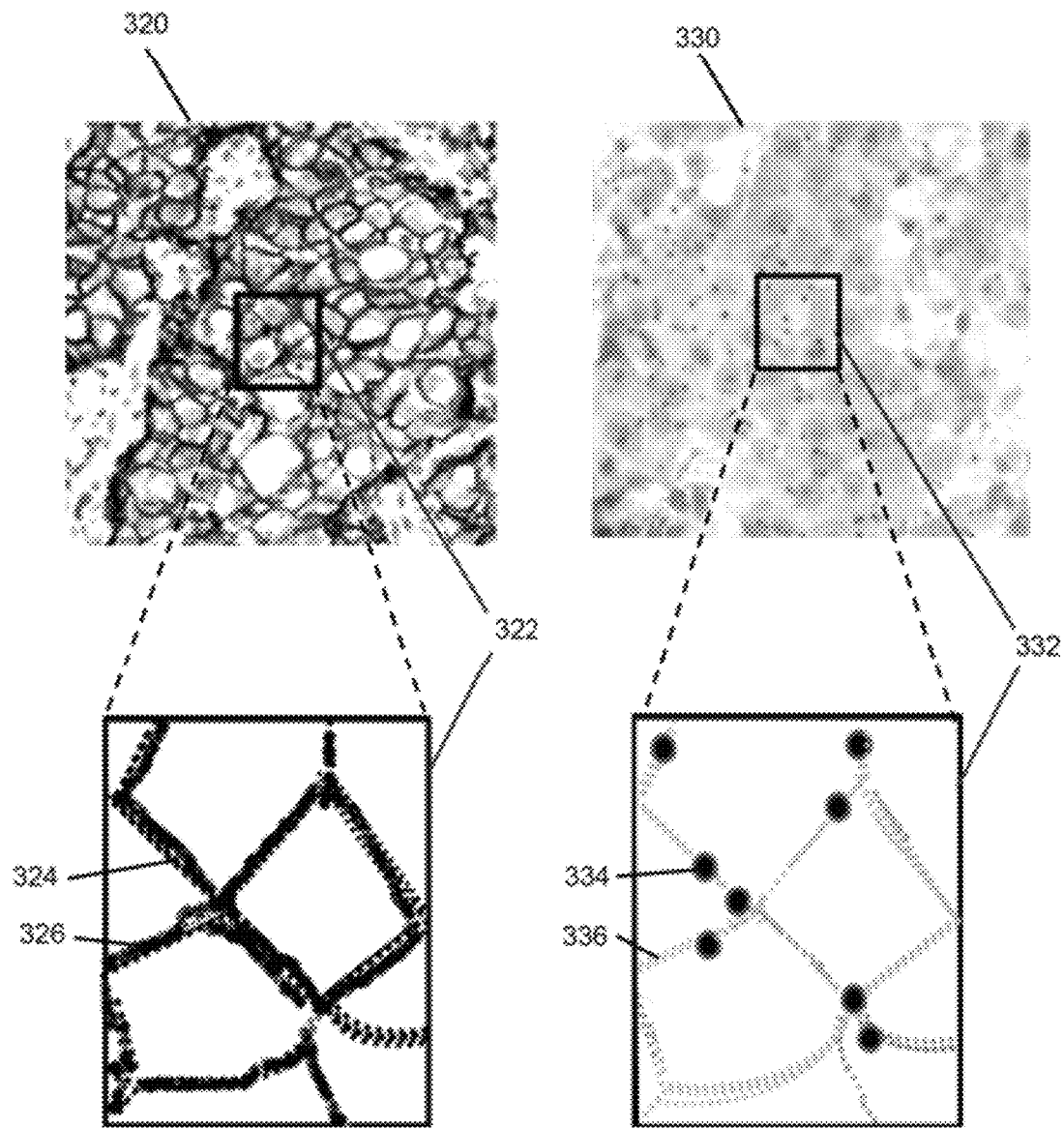
FIG. 3B compares conventional IHC staining (left panel) with intensity-based quantitation versus PDQA staining (right panel) with dot based quantitation.

FIG. 3B depicts a comparison of two tissue specimens. On the left, a tissue section stained by conventional IHC staining is shown in image 320. On the right a tissue section stained by an embodiment of the programmable dot quantitative assay is shown in image 330 . . . A rectangular bounding box 322 is also illustrated superimposed over image 320. Bounding box 322 is also shown enlarged with an illustration of conventional IHC staining of cancer cells depicted within. As can be seen throughout image 320 and in the enlarged representation of bounding box 322, dark staining can be observed around the perimeter of the cells, i.e. the cell membranes. HER2/neu (also known as ErbB-2) stands for "Human Epidermal growth factor Receptor 2" and is a protein giving higher aggressiveness in breast cancers. It is a member of the ErbB protein family, more commonly known as the epidermal growth factor receptor family. In the illustration within enlarge bounding box 322, two segments of cell membrane 326 and 324 are depicted as dark lines representing the darkly stained membrane which can be seen throughout the photomicrograph image 320. In a typical example of conventional IHC, primary antibodies to the target protein are incubated on the tissue section. Then enzyme labels (e.g. horseradish peroxidase) which are conjugated to the primary antibodies in the direct IHC method, or to secondary antibodies that bind to the primary antibodies in the indirect IHC method are incubated on the tissue section. The enzyme labels are reacted with a substrate to yield a staining precipitate wherever the enzymes are bound, for example diamino benzadine (DAB) yields a brown staining. Where the expression of the target protein is higher, more chromogen is precipitated causing the intensity or darkness of the staining to be greater. Image analysis of conventional IHC typical includes measuring the intensity of the staining which is typically indicative of the expression level of the target protein.

In image 330, staining by a programmable dot quantitative assay (PDQA) is depicted. In one typical PDQA staining indirect method, primary antibodies are applied as with conventional IHC to detect and bind to target antigens within the tissue section. Then secondary antibodies are applied. However with embodiments of PDQA only a predetermined fraction of secondary antibodies are labeled. Prior to the final staining step, an amplification reaction occurs leading to an intense spherical precipitation extending radially from the site of a single bound target antigen which results in optically distinguishable dot of a programmable size and shape being formed at the sites of a predetermined fraction of the target antigen sites. A more detailed explanation of exemplary embodiments is described below in the Additional Examples and Embodiments section.

From an image analysis perspective, the result is that, instead of determining the regional target protein expression within a specimen by measuring the intensity of nondiscrete staining as typically done in image analysis of IHC stained tissue, with PDQA the expression level is measured by recognizing dots having the programmed size, shape and other programmable optically recognizable characteristics such as color, intensity, sharpness, refractive profile, and so forth, and then quantifying the dots (e.g. by counting or other quantification method). Because the proportion of tagged antibodies is known, the results of the dot quantifying step can be used to calculate the absolute expression level of target antigen for a region of tissue within statistical margins of error. Additional detailed description and examples of how embodiments of PDQA may be used to determine absolute target antigen expression levels are provided in the Additional Examples and Embodiments section.

In convention IHC staining, the size and shape of stained objects within the image is determined primarily by the size and shape of the tissue components where the target antigens are located. This is illustrated in bounding box 322 of FIG. 3b when the shape of the stained areas follows the shape of the cell membranes and the size of the staining is the size of membranes expressing sufficient target antigen to result in staining.

In contrast, the dots produced by PDQA as illustrated in bounding box 332 have a size, shape, and other programmable optically recognizable characteristics that are statistically consistent and predictably generally independent of the size and shape of the tissue components, such as, in this example the size and shape of the membranes expressing sufficient target antigen to cause the primary antibodies to bind.

Figure 4:
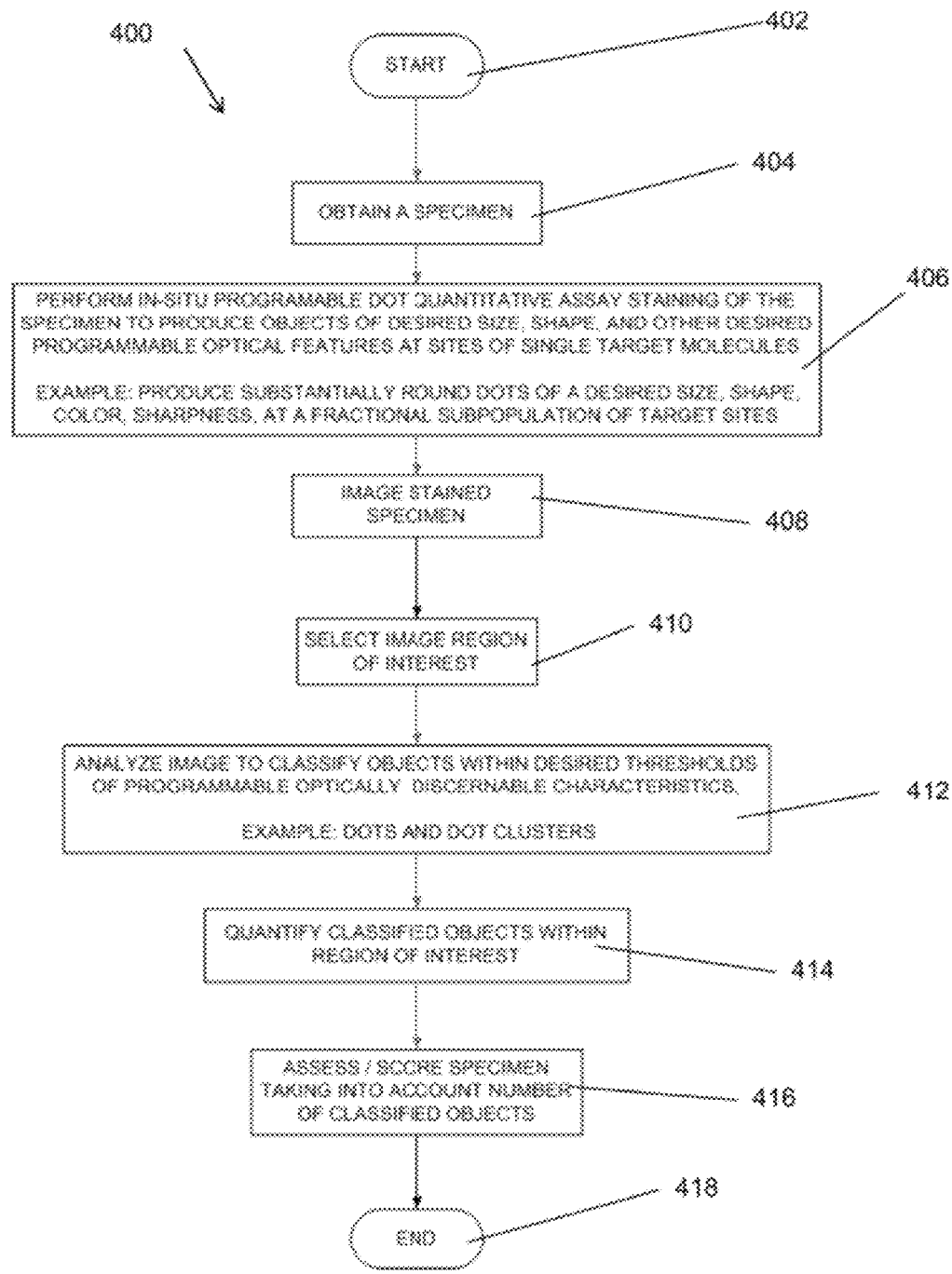
FIG. 4 illustrates process steps of an embodiment of a method for analyzing images of specimens processed by a programmable quantitative assay.

FIG. 4 illustrates process steps of an embodiment of a method 400 for analyzing images of specimens processed by a programmable quantitative assay. In some embodiments, a specimen is obtained 404. Pre-analytical steps (not shown in FIG. 4 but discussed in more detail with relation to FIGS. 21A-21C) may be performed if desired, after which processing, i.e., staining is performed by a programmable dot quantitative assay 406. The staining includes producing optically recognizable or recognizable objects within or on the specimen. For example, in some embodiments, substantially round dots of a size suitable for performing image analysis on an image of the specimen are produced at sites such as a fractional subpopulation of target sites.

The stained or processed specimen is then imaged 408, for example optically in the case of image via conventional microscope or human vision. In some embodiments the stained or processed specimen may be imaged digitally, for example by a microscope with an attached digital camera, or a microscope slide scanner.

A region of interest within the image is selected 410, again manually or digitally, for which region it is desired to assess a target expression level.

The image may then be analyzed manually or automatically, or in some embodiments semi-automatically. Objects such as, for example, dots, which are chemically programmed to have optically discernable or recognizable characteristics, may have been produced within or on the specimen. In some cases, objects may overlap or form a cluster, for example, a cluster of dots. The step of analyzing the images 412 may include preprocessing such as background subtraction or deconvolution. Step 412 may further include segmentation. Segmentation may be manual or automatic. Segmentation may be based on intensity of pixels, whether in one of many possible color spaces, or in black and white, or in grayscale. Edge base segmentation may also be used, for example kernel based segmentation or segmentation using structuring elements. Region based segmentation may also be used based on principles of image energy, probabilistic models, constraint models, or inside/outside functions.

Feature extraction, i.e., object detection or recognition may be performed on the image as part of step 412 based on any of the programmable optical features. For example in some embodiments, the objects produced are substantially round dots. In other embodiments the objects may appear optically as concentric rings. This will be discussed further with respect to FIGS. 17A-17B and FIGS. 18A-18C.

Step 412 may further include filtering processes, for example based on shape or intensity.

Step 412 may also include object classification processes, for example construction of a Voronoi diagram or analysis of nuclei or periphery. Dot tracing via triangulation and mesh generation are other examples of structure analysis.

With conventional IHC staining, segmentation is often performed using the color or hue of the staining as primary parameter to segment unstained tissue and stained tissue. Typically pixels of an image having a hue or color in a range predetermined to correspond to unstained connective tissue or to open unstained areas within the section or to areas of the slide where no tissue is present are considered background pixels. Likewise, pixels of an image having a hue or color in a range predetermined to correspond to a chosen stain are identified as pixels for further analysis. The further analysis could include measurement of intensity, object recognition or any number of image processing analyses. However, in embodiments of PDQA staining, one need not segment the image first by color or hue of the staining. Since the dots produced by PDQA staining have a programmable size and shape that is optically recognizable independent of color, the programmable characteristics of the dots may be recognized by size and shape first, followed by further classification by color or hue. Alternatively, recognition and quantification of the set of optically programmable features can occur with multiple parameters simultaneously or in any desired order. Image analysis techniques for recognizing object of certain shapes or sizes can be found. As one example, Hough transform is a technique used to detect circles. There are generalized and probabilistic versions of Hough transform. Ellipse fitting methods can be used as well.

Classification of the image may include step 414, quantifying the objects within the regions of interest. In some embodiments the step of quantifying may include for example dot counting, normalized dot counting, dot counting per unit area, dot counting per cell, counting dots per nucleus, dots per region, or ratiometric counting of different types of objects or dots. Quantification could also be done by quantifying the dot area, stained pixel area, position of dots relative to specimen features, position of dots relative to other dots, or position of dots relative to other features including morphological features.

Also notable, is the fact that since the PDQA dots may be programmed to have a substantially round shape and a size within a predetermined range, a center point or dot origin may be calculated for each dot. Once a dot origin has mathematically defined for each dot, and dots have been classified using any of the available programmable characteristics, geometric analysis techniques may be used which do not require computation taking into account and the size and shape of the dots but are performed using the coordinates of the dot origins for each class of dots. Distance between dot origins, regional density of dot origins and so forth may be utilized in further computation and analysis.

All of the features (size, shape, color, intensity, sharpness, refractive profile, and so forth) can be used together to separate out one or more kind of dots (single or multiplexing) by either using unsupervised learning techniques (e.g. clustering using k-means, k-nearest neighbors, principal component analysis (PCA), independent component analysis (ICA), singular value decomposition (SVD), matrix factorizations, neural networks, Bayesian methods, expectation-maximization, self organizing map (SOM), graph based methods like grab cut or normalized cut, information theoretic methods such MDL, Minimum Message Length (MML), kernel variants of PCA and other techniques) or using supervised methods directly or after clustering (using neural networks, kernel methods, Bayesian methods, decision trees, boosting, SVMs, randomized algorithms). One could also use semi-supervised algorithms which would include most of these techniques.

Images of the specimen, processed images, or graphical, numerical, or textual data may be displayed.

Step 416, assessing or scoring of the specimen image or regions of the image based on the image analysis performed in steps 412 and 414, involves generating or producing a score. In some embodiments, the score may be an absolute target expression level, i.e., a target expression score that is proportional to and representative of the total number of target molecules within the specimen as opposed to a relative target expression level.

The step of assessing or scoring 416 may further include generating a clinically meaningful composite score, related to a conventional pathology score such as an Allred score.

Figure 5A:
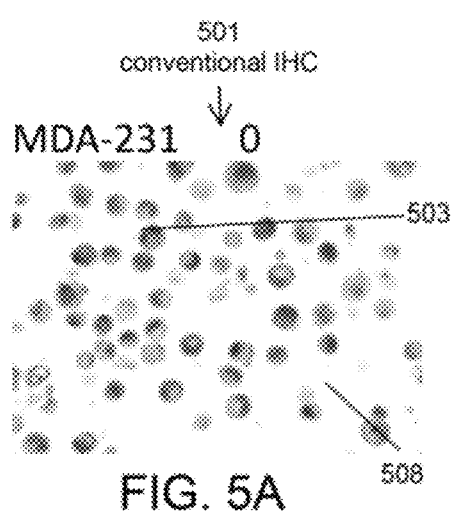
FIGS. 5A-5C are images of control cell lines with known cancer states stained by conventional immunohistochemistry.
Figure 5A:
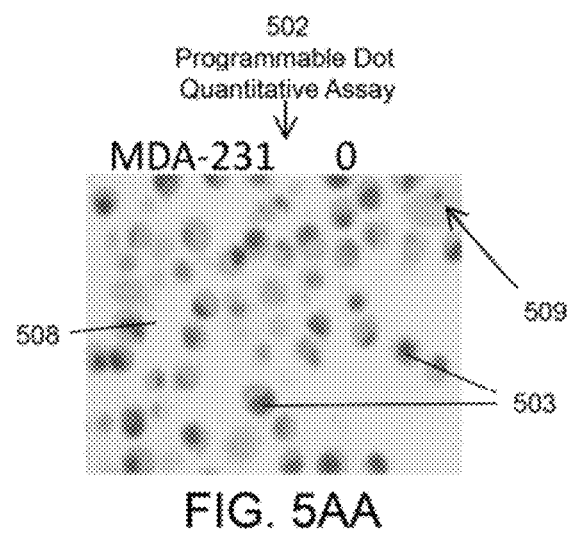
Figure 5B:
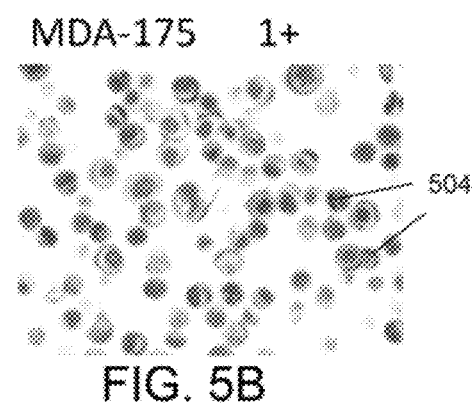
Figure 5B:
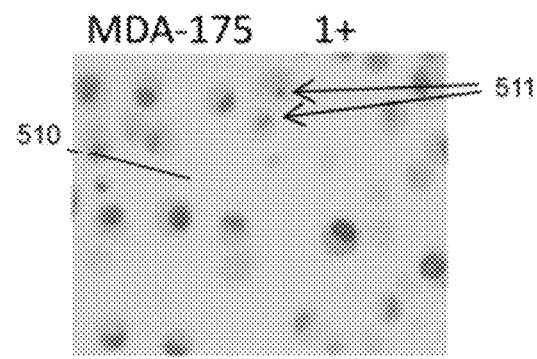
Figure 5C:
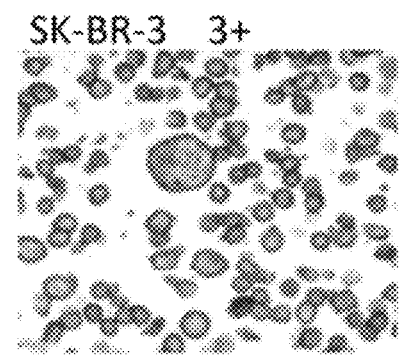
Figure 5C:
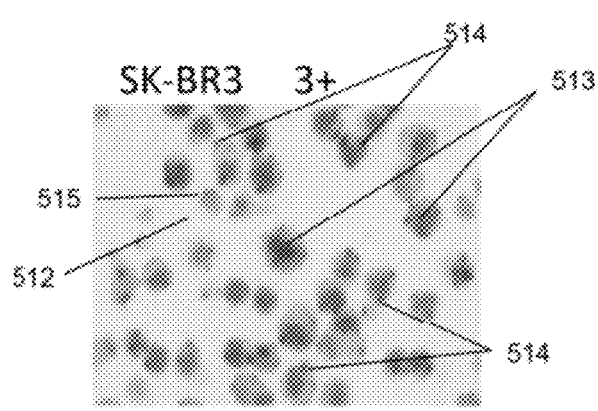

FIGS. 5A-5C are images of control cell lines with known cancer states stained by conventional immunohistochemistry. Human breast cancer cell lines with different levels of Her2 expression are represented. These images are presented for later comparison with quantitative staining using a programmable dot quantitative assay.

FIG. 5A is an image of cell line MDA-231, an example of breast cancer cells that do not express high levels of Her2. FIG. 5A as well as FIGS. 5B and 5C show cells 503 which have been counterstained blue with hematoxylin which makes the cell nuclei appear dark blue in the image. Background areas 508 where no cells are present may or may not appear to have some weak blue hematoxylin staining or background staining. In FIG. 5A there is no apparent brown diaminobenzidine, herein after DAB, staining.

In FIG. 5B, partial membrane staining 504 may be seen as brown DAB staining in arcs or portions of certain cell membranes, indicating a low level of target expression (in this example, Her2). Cell line MDA-175 acts as a control cell line to give a visual example of the type of staining that should be scored as a 1+. It may also serve as a quality control mechanism for checking the staining process. If the control cell line MDA-175 undergoes the prescribed processing protocols and conditions are normal, one would expect to see images similar to the image of FIG. 5B.

The image of FIG. 5C shows complete membrane staining around >10% of SK-BR-3 cells within the region of interest; thus cell line SK-BR-3 as shown in FIG. 5C is scored as a 3+, i.e., positive for Her2.

Thus, the images of FIGS. 5A-5C may be assessed/scored manually or with the help of an image analysis system. However, the size of the stained region is not produced via a programmable quantitative assay. Rather, the size and shape of the stained region is determined by size and shape of the inherent structure of the specimen and associated levels of target expression located within that structure.

FIGS. 5AA-5CC are images of control cell lines with known cancer states processed by a programmable quantitative assay.

In FIG. 5AA, blue counterstained cells with dark blue stained nuclei, such as nucleus 503, can be seen. The number of blue stained nuclei may serve as an estimate of the number of cells which can be used as a reference. Non-specimen area 508 or background can also be seen. Depending upon the lighting conditions, a bluish tint may be visible in background area 508. This can, in certain conditions, require additional filtering so that none of the pixels with a blue tint are inadvertently classified together with the objects of interest, for example the blue stained nuclei. For both the nuclei 503 and the background, the size and shape of the staining is determined by the size and shape of the specimen and its surrounding environment.

Significantly, with embodiments of the method of analyzing images processed with a programmable dot quantitative assay, also referred to as a programmable discrete quantitative assay or PDQA, dots such as dot 509 shown in FIG. 5AA are produced. With PDQA, also known as Single Molecule Detection or PDQA, the size and shape of the dots are not determined by the size and shape of the specimen or its surrounding environment. The size and shape of the dots to be produced may be programmed in situ, i.e., while the PDQA reagents are processing, i.e., staining, the specimen. Other optical features or characteristics such as dot color may be programmed into the PDQA which make it easier to optically recognize the dots. For example, dot 509 has a reddish hue which is recognizable as being different from the light blue tint of the background 508 and the dark blue staining of the nuclei 503.

Thus, optical features of the dots produced in this example are intentionally programmable and consistent. Their size and shape is independent of the size and shape of elements within or surrounding the specimen. Nor is the size, shape or color of the dots significantly dependent on the target expression levels within the specimen. This can make it easier to optically detect and/or recognize/classify the dots regardless of the nature or state of the specimen.

Notably, the number of dots is in fact dependent on the target expression levels for a given region or compared with references such as the number of cell nuclei. Also, the positioning of the dots and distance between dots is related to the regional target expression levels. High levels of target expression are processed by a programmable dot quantitative assay to produce more dots within the high expression region.

As expected, FIG. 5BB shows more dots 511 produced for a cancer cell line scored as 1+ than in FIG. 5AA, a cancer cell line with lower Her2 target expression.

FIG. 5CC shows a significantly higher number of red dots 514 and some double dots or dot clusters may be seen such as dot cluster 515 in which three dots form an arc positioned at an arc shaped portion of a cell membrane.

FIG. 5D shows a table 530 which shows concordance of results from image analysis of a control cell lines processed by a programmable quantitative assay.

Column 550 of table 530 holds the names of the cancer cell line used, starting with the lowest target expressing cell line MDA-231 on row 540, with the somewhat higher target expressing cell line MDA-175 next on row 540 and the highest target expressing cell line SK-BR-3 at the bottom in row 544.

Column 560 shows the designated score from 0 to 3+ for each of the cell lines.

Column 570 shows the PDQA number of dots within the region of interest of the image, the number of dots being normalized by the number of nuclei within the region of interest of the image.

Column 580 shows the number of target molecules, i.e. Her2 receptors, per cell, as summarized in scientific publications.

Notably, the ratios of dots per nucleus 570 across the different cell lines as quantified by the programmable dot quantitative assay concords significantly with the ratios of the number of receptors per cell across the cell lines shown in column 580.

The number of PDQA dots for a given target expression level may be programmed. In some embodiments, the number of dots for a given target expression level may be programmed to be such that at the highest expected target expression levels, there is some overlapping of dots but the dots are still generally identifiable as individual dots rather that mostly dot clusters. In other embodiments, the number of dots for a given expression level may be programmed to produce a significant quantity of generally overlapping dots and large areas of dot clusters. An example of this can be seen in the images shown in FIG. 15.

FIGS. 6A-6D depicts one field of view with images of one specimen processed by a programmable quantitative assay at four different resolutions.

Figure 6A:
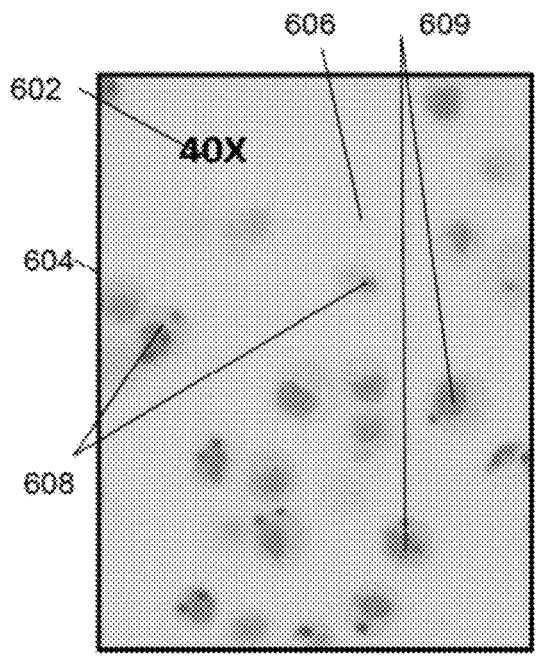
FIGS. 6A-6D depicts one field of view with images of one specimen processed by a programmable quantitative assay at four different resolutions.

FIG. 6A shows an image taken of a PDQA stained slide in field of view 604. The image was captured using at a 40× setting 602. The 40× setting corresponds to the use of a 40× objective which for many digital microscope systems and scanner provides a resolution of about 0.25 microns per pixel. Blue counterstained nuclei 609 can be seen along with red stained PDQA dots 608 against a light background 606.

Figure 6B:
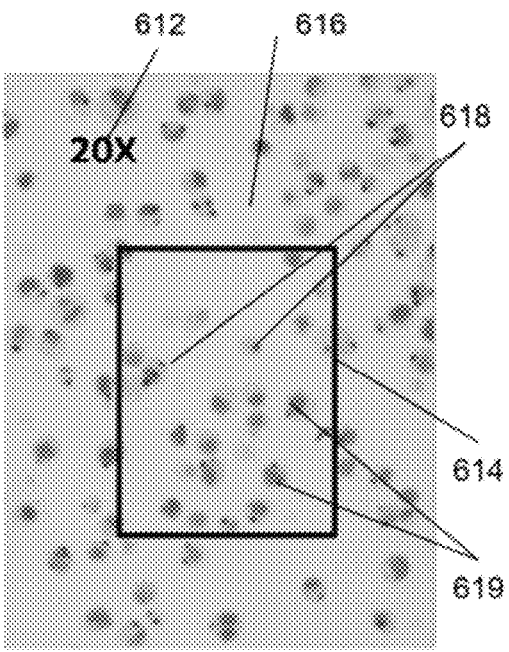
Figure 6C:
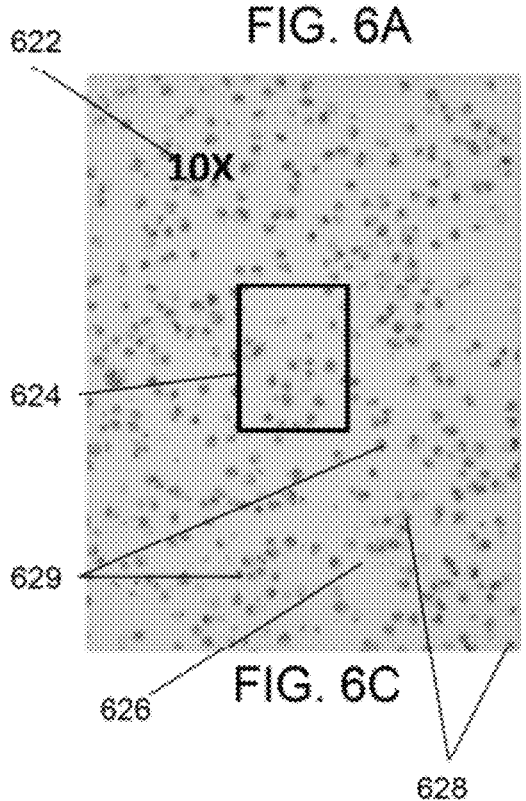
Figure 6D:
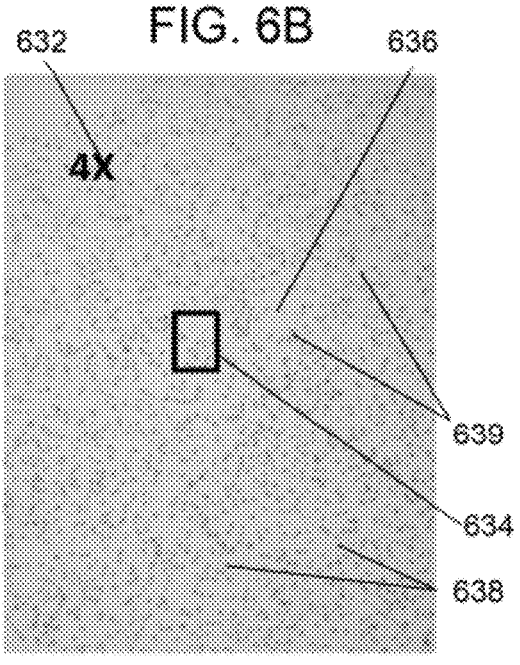

FIG. 6B is an image of the exact same microscope slide and cell line specimens imaged at a 20× setting 612. FIG. 6B shows an image in a field of view 614. The image of FIG. 6B has a larger overall field of view, i.e. a larger portion of the microscope slide and specimen has been imaged. However, field of view 614 is the same as field of view 604 shown in FIG. 6A. Therefore, the optically recognizable objects and features such as red stained PDQA dots 618 are the same dots as the dots 608 seen in the image shown in FIG. 6A. Likewise the blue counterstained nuclei 619 of FIG. 6B are the same nuclei 609 seen in FIG. 6A. Corresponding fields of view 624 and 634 are shown in FIG. 6C imaged at 10× and FIG. 6D imaged at 4× respectively.

FIG. 6E shows a table with substantially matching results from image analysis of the field of view in the images taken at different resolutions as depicted in FIGS. 6A-6D. Rows 640, 642, 644, and 648 contain data related to the images of FIGS. 6A, 6B, 6C, and 6D respectively.

Table column 660 shows the number of dots counted in fields of view 604, 614, 624, and 634 which are in fact the same field of view of the same slide taken at the 40×, 20×, 10×, and 4× settings respectively. The number of dots counted manually was 18 in all cases.

Table column 665 shows the number of dots counted using an automated embodiment of the method of image analysis. Threshold parameters for the hue of the dots were set in the image analysis algorithm. The objects, i.e., dots, were then recognized, classified and counted automatically, with the result as shown in table column 665 that the same dots were identified in all four images taken at four very different resolutions. Significantly, the image analysis and counting algorithm used was identical for all four images. This demonstrates that by appropriately programming the size, shape, and color of the dots to be produced, the robustness and clarity of the programmed optical features may enable image analysis to be reliably performed at lower resolutions such as 10× or even 4× with a less than 10% error rate as illustrated in table column 670.

Advantages of embodiments of the method and systems for analyzing images processed by a programmable quantitative assay which includes dot optical feature programmability can be seen in columns 675 and 680 where one can see that the storage, data transfer, and microscope stage positioning requirements, are much greater for images captured at the 40× setting than the corresponding requirements for images captured at the 10× or 4× settings.

Figure 7A:
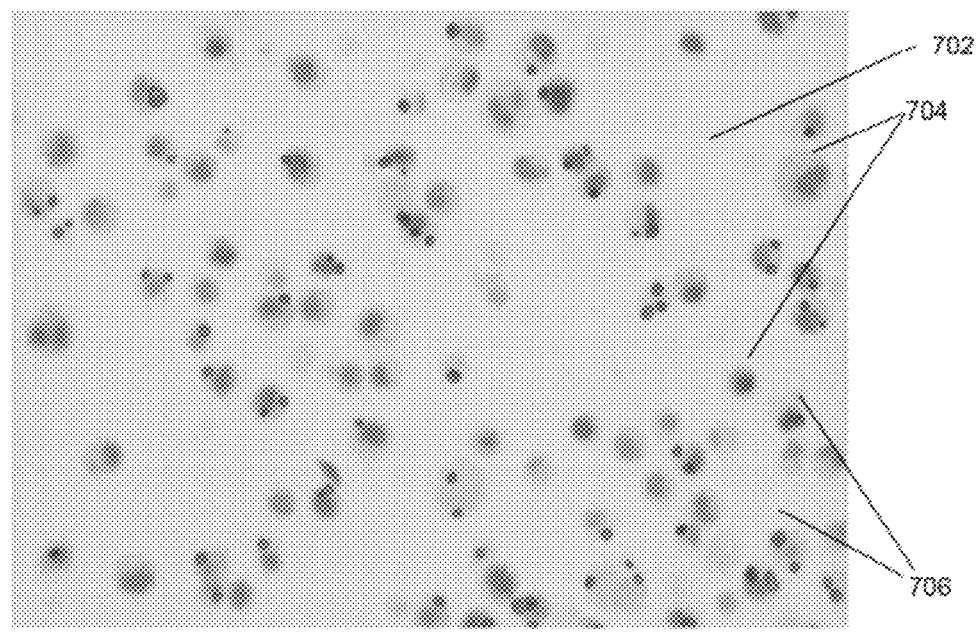
FIG. 7A shows an image taken two steps out of focus above a slide with control cell lines processed by a programmable quantitative assay.

Because the PDQA dots can be programmed to be of a size that is readily quantifiable even at relatively low magnifications (e.g. 4×), the amount of data and processing requirements to perform whole slide analysis is greatly reduced. To achieve even greater reductions in data to be handled and processing needed, dot origins can be determine for each dot after which quantitation and other types of density, geometric, and ratiometric quantitation/assessments may be perform using the dot origins rather than using all of the pixels classified as belonging to each dot, To demonstrate another aspect of PDQA staining and imaging, FIG. 7A shows an image of a slide with control cell lines processed by a programmable quantitative assay. The image shown in FIG. 7A was taken two steps out of focus above, i.e., the focal plane of the microscope was higher than the focal plane designated as in focus or 0.

This was done by first focusing the microscope to a focus depth where the edges of most cells visible were clear and sharp. Then the microscope was brought by steps to two steps out of focus above when the image of FIG. 7A was captured, and to two steps out of focus below when the image shown in FIG. 7B was captured. As before, red stained dots 706 and blue counterstained nuclei 704 can be clearly seen in both FIG. 7A and FIG. 7B even though the image of FIG. 7A was captured at two steps out of focus above and the image of FIG. 7B was captured at two steps out of focus below.

Figure 7B:
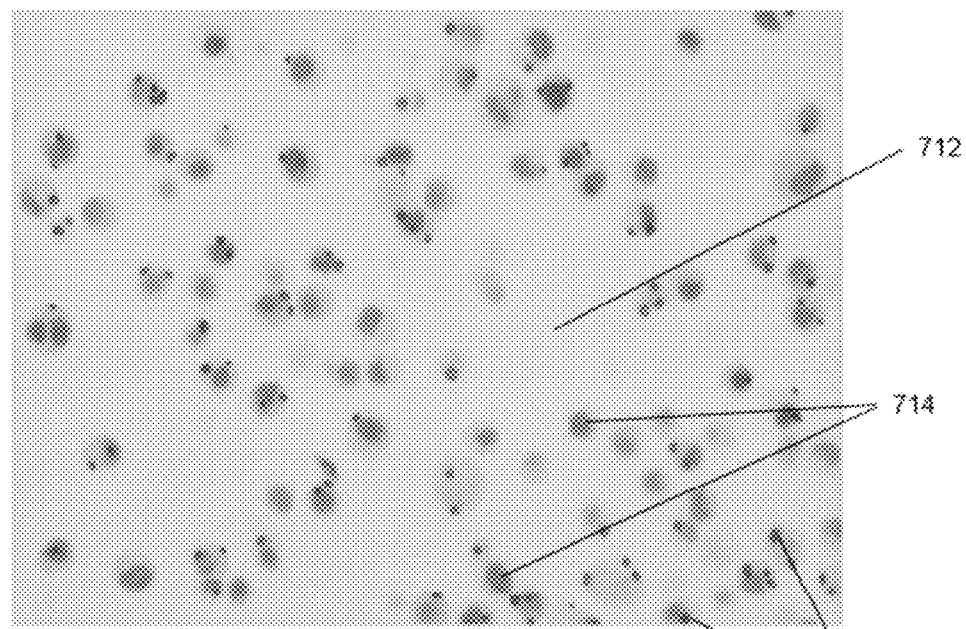
FIG. 7B shows an image taken two steps out of focus below a slide with control cell lines processed by a programmable quantitative assay.
Figure 7C:
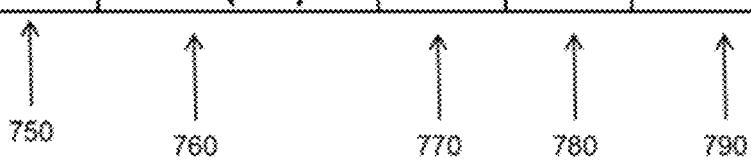
FIG. 7C shows a table with substantially matching results from image analysis of one field of view in the images taken at five different focal planes including those illustrated in FIGS. 7A and 7B.

FIG. 7C shows a table with substantially matching results from image analysis of one field of view in the images taken at five different focal planes, namely in focus, one and two steps above focus, and one and two steps below focus as shown in table column 760. Data in row 740 corresponds to the image shown in FIG. 7A and data in row 748 corresponds to the image shown in FIG. 7B.

Column 770 shows a manual dot count taken at each of the five focal planes based on subjective pre-established criteria regarding when to count a dot and when to not count a dot. For example, in the manual counting method used, a group of pixels which appeared very diffuse and very light red is not to be counted, particularly if it appears to be separated from other objects such as cell perimeters or cell nuclei. Such a phenomenon may be observed for example when a cell has been cut by a microtome in the section process so that just a tiny sliver of an outer perimeter of a cell remains. When such a cell portion is stained by PDQA, a dot may in fact be formed centered around the binding point of the detecting antibody at the site of a single target molecule. However, because the cells are being stained which are not held within the connective matrix or substrate of a tissue, the dot formed may have no substrate to which it holds and thus may be partially or completely washed away during the latter parts of the staining process.

As one would expect, the degree to which the image is in focus may impact the hue, intensity, or sharpness of Objects being imaged. However as shown in column 770 the number of dots counted manually at all focus levels is very close to the same. Further, the number of dots counted using an embodiment of an automated dot counting method is also very close to the same across focus levels. Also, the number of dots counted by automated algorithm as shown in column 780 corresponds substantially with the manual count 770. The automated dot counts 780 are unadjusted which means that any overlapping dots are counted as a single object, even though in the manual dot count they can be seen to be for example two individual dots. Thus a relatively high success rate can be seen, i.e., the number of dots counted by the automated method compared to the number of dots counted manually matches well (see columns 770, 780, and 790) at the individual focus depths as shown in rows 740, 742, 744, 746, and 748. Also the success rate across focal depths as shown in column 790 is typically greater than 90%

Figure 8A:
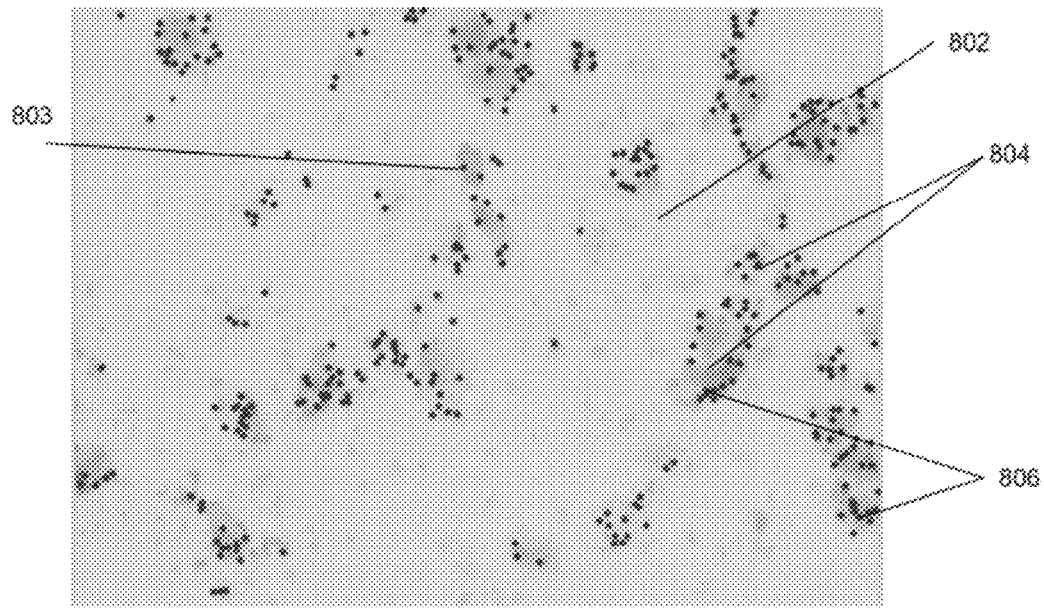
FIG. 8A shows an image taken in focus of a slide with control cell lines processed by a proximity ligation assay with blobs identified and annotated manually.
Figure 8B:
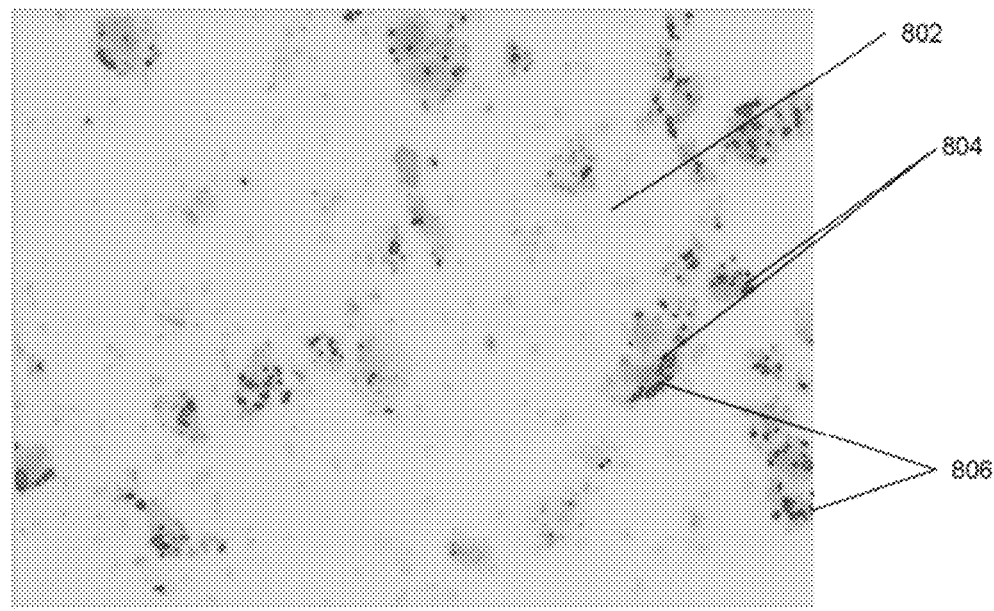
FIG. 8B shows the image of FIG. 8A with blobs identified and annotated by image analysis software.

For purposes of comparison, in FIGS. 8A and 8B, another set of images was captured using specimens and image settings similar to those used to generate the images and results represented in FIGS. 7A, 7B and 7C. However, a proximity ligation assay or PLA was used to produce blobs of staining within the image. This assay is targeted at staining sites expressing Her2 within a specimen. But the assay itself as well as the images produced differ substantially from the images shown in FIGS. 8A and 8B in which the specimen to be imaged was processed by a programmable dot quantitative assay.

Also in the comparison case of PLA staining, both the images 8A and 8B were captured in focus rather than at different steps out of focus. In other words, the image shown in FIG. 8A and FIG. 8B corresponds to an in focus image referred to by row 824 of the table shown in FIG. 8C. Additional images were captured at different focus depths but these individual images are not shown in the drawings. However, data from these images taken at the same specific focus points is shown in FIG. 8C.

FIG. 8A is an image captured in focus with red dots placed in a manual blob counting process. FIG. 8B is the same image as in FIG. 8A, but in which a red perimeter has been automatically added around blobs identified via automated image analysis. A proximity ligation assay may be obtained from Olink Bioscience of Uppsala, Sweden. The assay used was a DuoLink Q targeted at staining Her2 molecules. Object counting software called BlobFinder may also be obtained from Olink.

In the image of FIG. 8A, blobs were counted manually using substantially similar criteria to those described above with respect to FIGS. 7A and 7B. In FIG. 7A, the sharp bright red dots 806 are not the blobs produced by the assay. Rather they are manually placed image markers added as part of the manual counting process. The observer places a round red dot at locations within the image where he or she perceives a blob to have been formed.

FIG. 8B shows the image of FIG. 8A with blobs identified and annotated by image analysis software. In some areas such as area 804 and 806, blobs were identified manually and red dots were manually placed on top of the blobs in the image of FIG. 8A, and corresponding blobs were automatically recognized in areas in FIG. 8B, i.e., 804 and 806. It should be noted that the manually placed dots are circular dots of a uniform size, and are not representative of the size of the blobs, which appear to vary significantly in size and shape. It is also notable that blobs identified manually at areas such as area 803 were not sufficiently optically distinct from surrounding pixels to be classified and counted at blobs by the automated counting algorithm used to count blobs in FIG. 8B.

Further, as seen in both FIGS. 8A and 8B, areas of no staining or light background 802 may also be observed. Some areas such as area 804 appear to have staining, but it is not clear whether the staining is a result of darker background staining, i.e., chromogen deposited at sites other than target molecule sites, or whether the staining is a target molecule site but is substantially overlapping to the point that individual small blobs are not readily recognizable, either manually as performed in the image of FIG. 8A, or by automated analysis as shown in FIG. 8B.

FIG. 8C shows a table comparing results of an image taken in focus of a slide with control cell lines processed by a proximity ligation assay with blobs identified and annotated by manual counting and by image analysis software. Significant discrepancies can be seen between the manual blob counts 850 for the various focal depths. Further, discrepancies can be observed for the automated blob count across focus depths as shown in column 860 and between manual and automated blob counts as described in each of the rows at column 870.

Figure 9A:
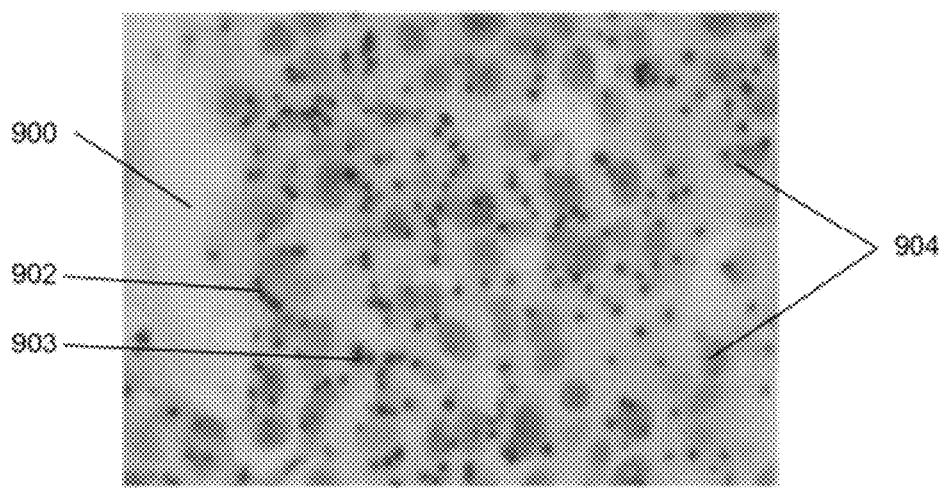
FIG. 9A depicts an image of a tissue specimen processed by a programmable quantitative assay.

FIG. 9A depicts an image of a tissue specimen processed by a programmable quantitative assay. Some background staining can be observed at connective tissue area 900. Bright red round dots were programmed to be produced at Her2 target sites, such as can be observed around the cell membranes at 902 and 903. Some dots at 902 and 903 appear to form dot clusters, but are still recognizable as dots having a programmed size and shape. However, automated dot recognition done by image analysis software may require dot count adjustment steps in order to improve the automated dot count, since an unadjusted dot counting algorithm may count these clusters as single objects having a larger than expected area and having optical features characteristic of dot clusters, i.e., appearing to be overlapping round dots and potentially having a darker, more intense staining of the programmed hue, as is perceptible at 902 and 903.

Figure 9B:
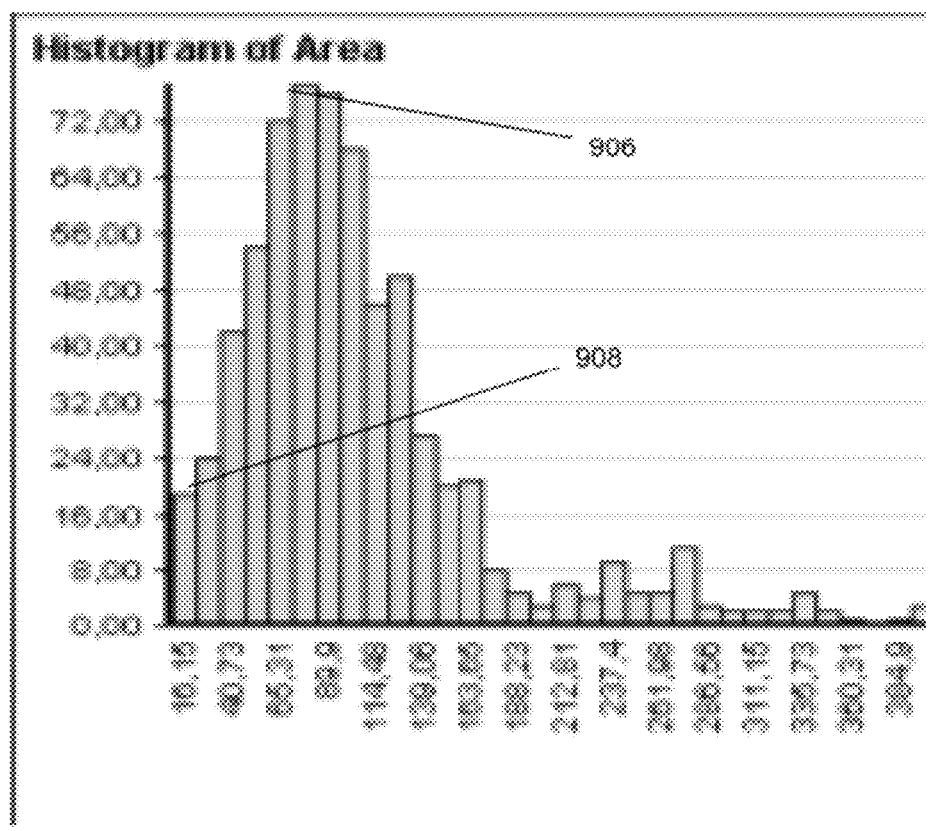
FIG. 9B depicts a histogram of dot size demonstrating statistical bounding of a population of dots within an image of a tissue specimen processed by a programmable quantitative assay.

FIG. 9B depicts a histogram of dot size demonstrating statistical bounding of a population of dots within an image of a tissue specimen processed by a programmable quantitative assay. The software used to implement an embodiment of the image analysis method for PDQA dots in this case was JMicroVision which is published by Nicolas Roduit, University of Geneva, Department of Geology, 13, rue des Maraichers, 1205 Geneva, Switzerland and was available for download at www.jmicrovision.com. The smallest objects recognizable with the version and settings of JMicroVision at the time it was used for the analysis are objects with a minimum area of ten pixels. As can be seen at 908 of FIG. 9B, about twenty objects recognized and classified by the software fell within the bin for objects with areas in the range of 10 to 16.15 pixels. However, as can be seen in FIG. 9B, the size of the objects has been programmed such that, for a given resolution of imaging, the separation between the median dot size 906, i.e., dot area, and the smallest measurable dot size/area and the shape of the relatively normal distribution statistically preclude the likelihood that a significant portion of the dots comprise dots with areas below the minimal recognizable area, i.e. less than ten pixels.

FIG. 10A depicts an image of a tissue specimen processed by a programmable quantitative assay. Dark reddish dots 1004 are present, as well as blue counterstained cells 1002 and darker blue counterstained cell nuclei 1006. Also observed are unstained areas 1000 with relatively light blue background staining. Dots were recognized using Matrox Inspector and Matrox Image Library image analysis software, which may be obtained from Matrox Electronic Systems Ltd., 1055 St-Regis Blvd., Dorval, Quebec, Canada, H9P 2T4. Dots were produced, images were segmented and dots were recognized and classified. Measurements of the optical features of the dots were derived and graphed.

For example, FIG. 10B depicts a histogram of object elongation of dots within the image shown in FIG. 10A. As can be seen at 1010 of FIG. 10B the vast majority of the classified dots have an elongation of around 1.0 which is the elongation of a circle. Of course, dot clusters such as 1003 and 1005, where overlapping dots may be classified as single individual objects, may have an elongation closer to 2.0, depending on the amount of overlap.

FIG. 10C depicts a histogram of object compactness of dots within the image shown in FIG. 10A. Compactness is the ratio of the area of an object to the area of a circle with the same perimeter. Therefore, a circle or substantially circular object with a smooth perimeter would have a compactness measure of 1.0 or near to 1.0. A circular object having a rough or jagged perimeter would have a larger compactness measure depending on the depth of the jags, which affects the perimeter measurement. As can be seen at 1012 in FIG. 10C, the vast majority of PDQA dots have a programmed substantially round shape that results in a compactness of around 1.2.

FIG. 10D depicts a histogram of object min to max feret ratio of dots within the image shown in FIG. 10A. Min to max feret ratio is a measurement that compares the distance between two parallel tangents of the object at an arbitrary angle. In some cases this may provide a more sensitive measurement of the shape of an object. Again, the min to max feret ratio of a circular object would be 1.0. As shown in FIG. 10D at 1014, the majority of the objects have a min to max feret ratio around 1.0.

Figure 10E:
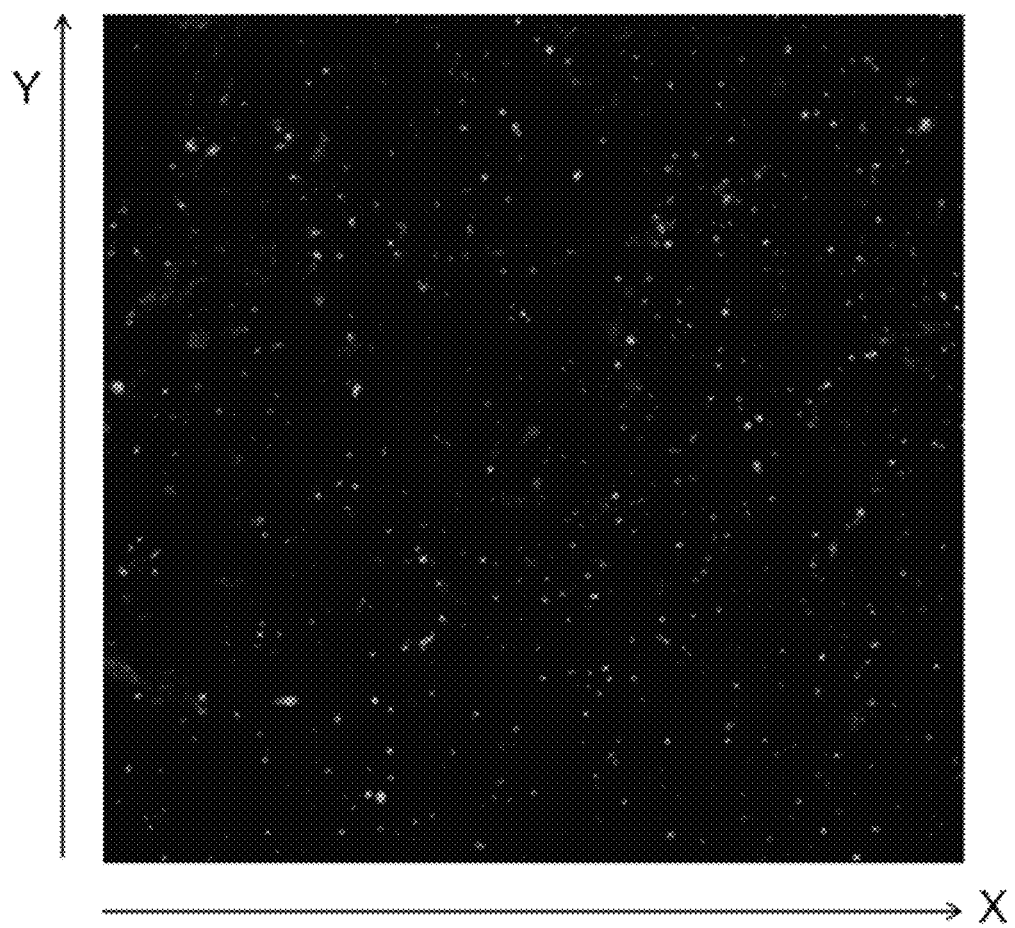
FIG. 10E is an XY 2D image of PDQA dots images using confocal microscopy.
Figure 10F:
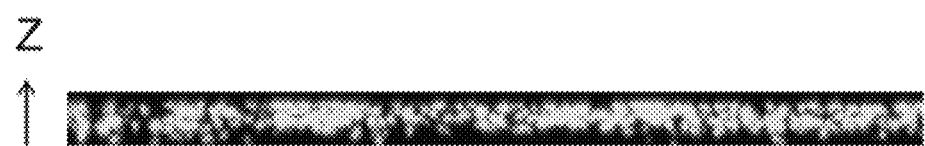
FIG. 10F shows a Z-axis cross section view of PDQA dots

FIG. 10E is an image created by confocal microscopy analysis of PDQA dots in a tissue specimen. In this analysis, PDQA dots were produced with DAB as the chromagen. When viewed in the XY plane, the PDQA dots appears substantially round. When viewed in a tissue cross section i.e. in the XZ or the YZ plane, it can be observed that the dots are in fact substantially spherical. Moreover, the dots are relatively evenly distributed throughout the tissue in the Z-axis. The three-dimensional substantially spherical shape of PDQA dots is an additional optically recognizable characteristic that may be utilized performing image processing and quantifying the assay.

Figure 11A:
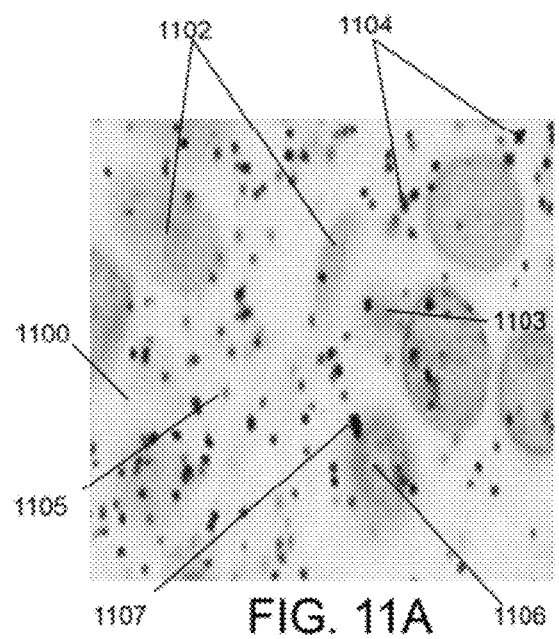
FIG. 11A depicts an image of a tissue specimen processed by a programmable quantitative assay.

For comparison purposes, FIG. 11A depicts an image of a tissue specimen processed by the proximity ligation assay or PLA. The image was taken from an electronically published publication by the providers of the assay. Blue counterstained cells 1102 and 1106 may be observed, as well as areas with no apparent intentional staining, such as area. 1100. Other areas, such as area 1103, appear to have a somewhat diffuse reddish hue, but no distinct object is readily recognizable. Blobs of various shapes, sizes, intensities and hues may be observed, such as the light reddish brown blob at 1105 and the dark brown oblong blob at 1107.

Figure 11B:
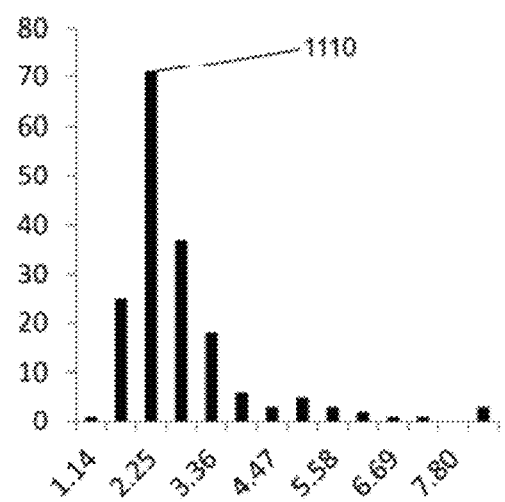
FIG. 11B depicts a histogram of object elongation of dots within the image shown in FIG. 11A.

FIG. 11B depicts a histogram of object elongation of blobs within the image shown in FIG. 11A.

Figure 11C:
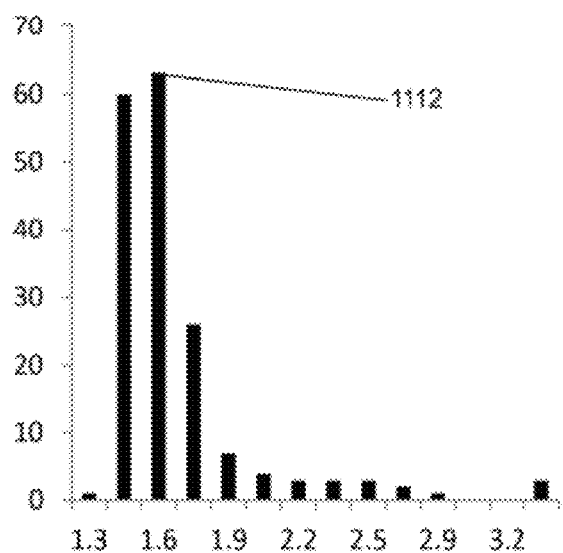
FIG. 11C depicts a histogram of object compactness of dots within the image shown in FIG. 11A.

FIG. 11C depicts a histogram of object compactness of dots within the image shown in FIG. 11A.

Figure 11D:
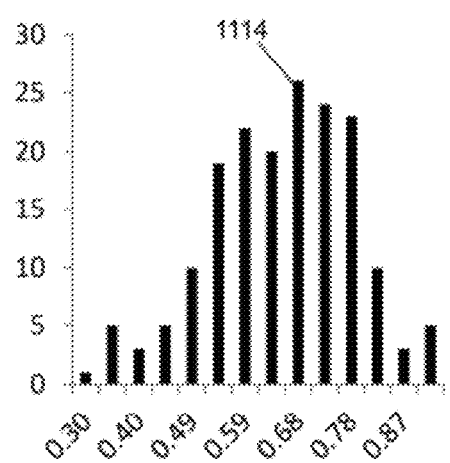
FIG. 11D depicts a histogram of object min to max feret ratio of dots within the image shown in FIG. 11A.

FIG. 11D depicts a histogram of object min to max feret ratio of dots within the image shown in FIG. 11A.

As can be observed in FIGS. 11B, 11C and 11D, the blobs are countable but do not appear to have programmed shape, size, and hue sufficient to perform a blob count adjustment along the lines of that which has been described with respect to the programmable quantitative dot assay described in the various embodiments of the invention.

Figure 12A:
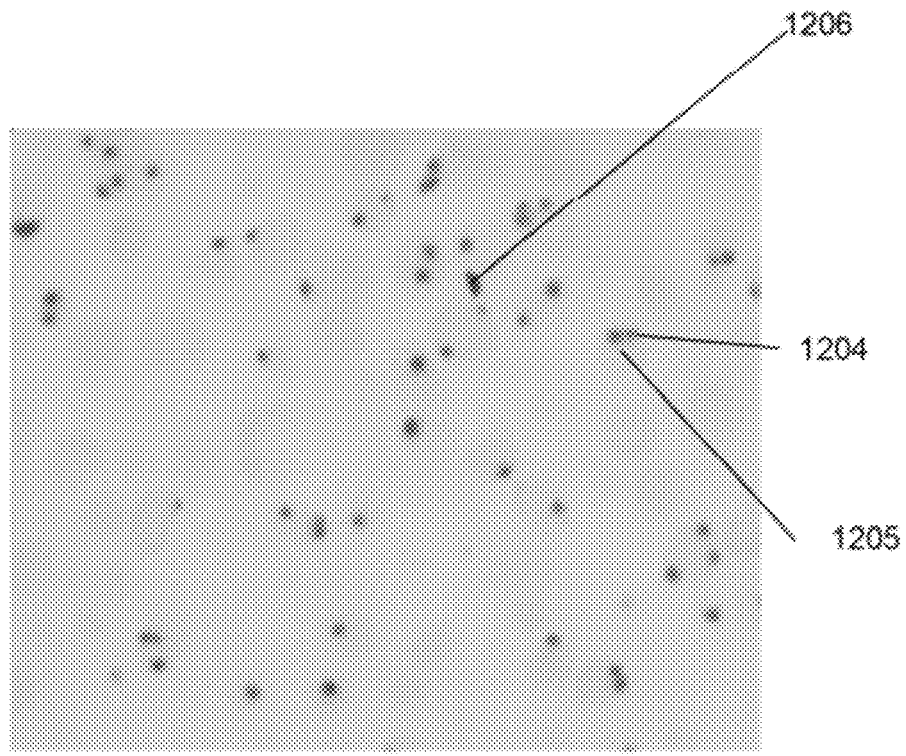
FIG. 12A shows an image of a specimen processed by a programmable quantitative assay.

FIG. 12A shows an image of a specimen processed by a programmable quantitative assay, where the image includes target dots, such as red round dots 1204 and 1205, and an artifact 1206. It may be noted that in the images of FIGS. 12A and 12B, there is no noticeable dark blue counterstaining of cells or cell nuclei. Artifact 1206 appears as a dark object. As an example, object 1206 may appear as a dark object due to being a particle which has lodged on the surface of the specimen and through which light may not readily pass.

Figure 12B:
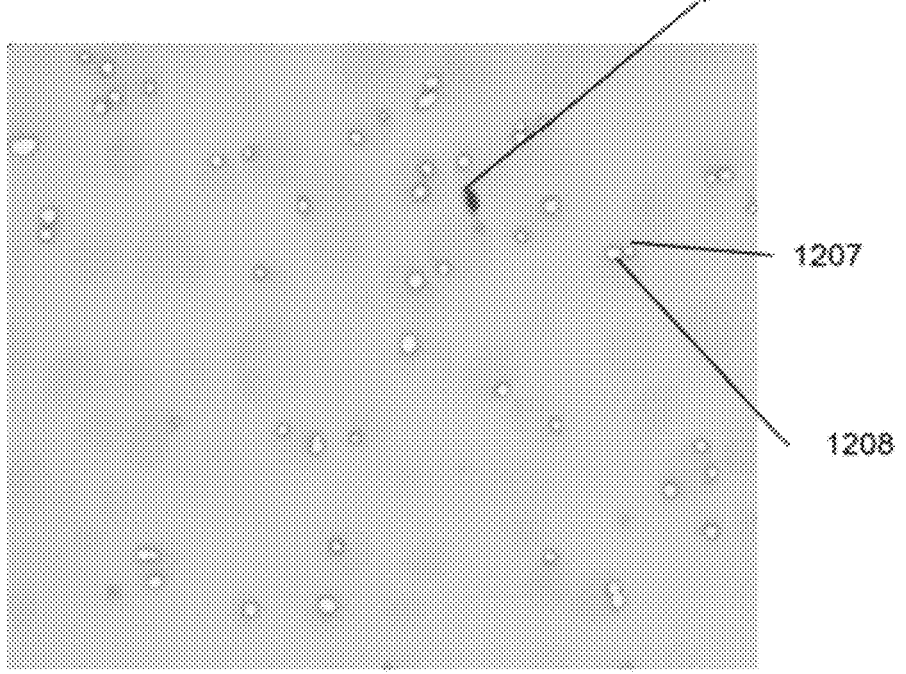
FIG. 12B shows a processed image that distinguishes the target dots and the artifact 1206 shown in FIG. 12A.

FIG. 12B shows a processed image that distinguishes the target dots and the artifact shown in FIG. 12A. Dots 1207 and 1208 have been shown as yellow dots having the same shape and location as dots 1204 and 1205 produced by the programmable dot quantitative assay and shown in FIG. 12A. It may be noticed that artifact 1206 was not recognized as a PDQA dot even though it has a shape and size similar to the shape and size of a dot cluster comprising dots 1207 and 1208. Thus it can be seen that, in addition to the programmable optical feature of size and shape, other programmable features such as hue, saturation, intensity, and so forth may be programmed to help separate or segment objects of interest, i.e., dots, from other objects, i.e., artifacts.

Figure 12C:
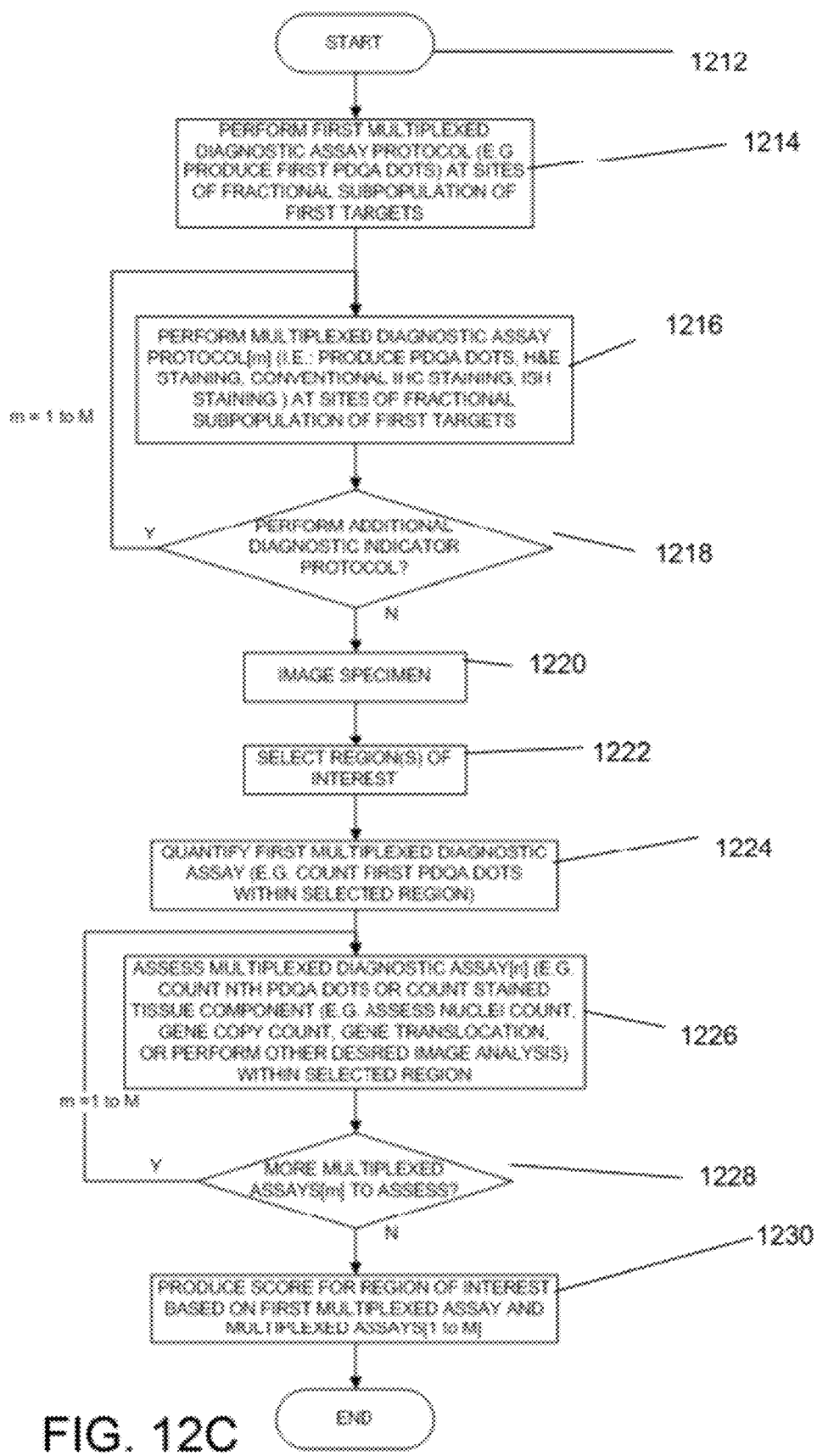
FIG. 12C show processing steps of a method of performing multiplexed diagnostics with PDQA dots as at least one of the multiplexed components.

FIG. 12C illustrates process steps of an embodiment of a method of scoring multiplexed diagnostic assays with a region of a specimen. In step 1214 a first multiplexed diagnostic assay protocol is performed at sites of a fraction subpopulation of first targets. For example, in some embodiments a PDQA protocol is performed where the first target is her2 protein. A primary antibody to Her2 protein is applied to breast cancer tissue. A predetermined fraction of tagged secondary antibody is applied causing the precipitation of the reporters and crosslinkers which are then chromogenically visualized.

At step 1216, additional multiplexed diagnostic assays protocols are performed. For example, in some embodiments the nth multiplexed diagnostic assay may comprise PDQA dots produced at a fractional subpopulation of from 1 to M target sites.

However, multiplexing assays may be performed an assessed where only one of the multiplexed-assay components comprises PDQA dots. Any of the 1 to M additional multiplexed assays may comprise producing and assessing PDQA dots having different programmable optical characteristics. Alternatively, any of the 1 to M assay may comprise other staining protocols in which the size and shape of the staining pattern follows the size and shape of the locations in the tissue where the staining targets are found rather than having a programmed shape like the round shape of the PDQA dots. Other embodiments may include H&E staining to highlight the morphology of the tissue. Still other embodiments may include In Situ Hybridization where certain genes are stained. Special staining protocols including histochemical assays may also be performed. The programmable dots quantitative assay may be performed before, after, or together with any combination of additional assays in any desired order If no more multiplexed assays are to be performed at step 1218, then the specimen may be imaged at step 1220.

At step 1222, regions of interest may be selected manually by a pathologist or technician, automatically, or semi-automatically. One example of a selected region of interest may be the whole slide. As discussed above with respect to FIGS. 6A-6E, whole slide analysis may require many fewer data points and greatly reduced computational power due to the readily optically discernable nature of the PDQA dots.

Quantitation of the first multiplexed assay, e.g. counting first PDQA dots and deriving dots counts from PDQA dot clusters may be accomplished using any suitable technique such as those described above with respect to FIG. 4.

When at step 1228, no more assessments 1226 remain to be performed, step 1230 may be performed.

At step 1230, a score may be produced by algorithmically combining results from step 1224 PDQA quantitation with results from M iterations of step 1228.

Figure 13A:
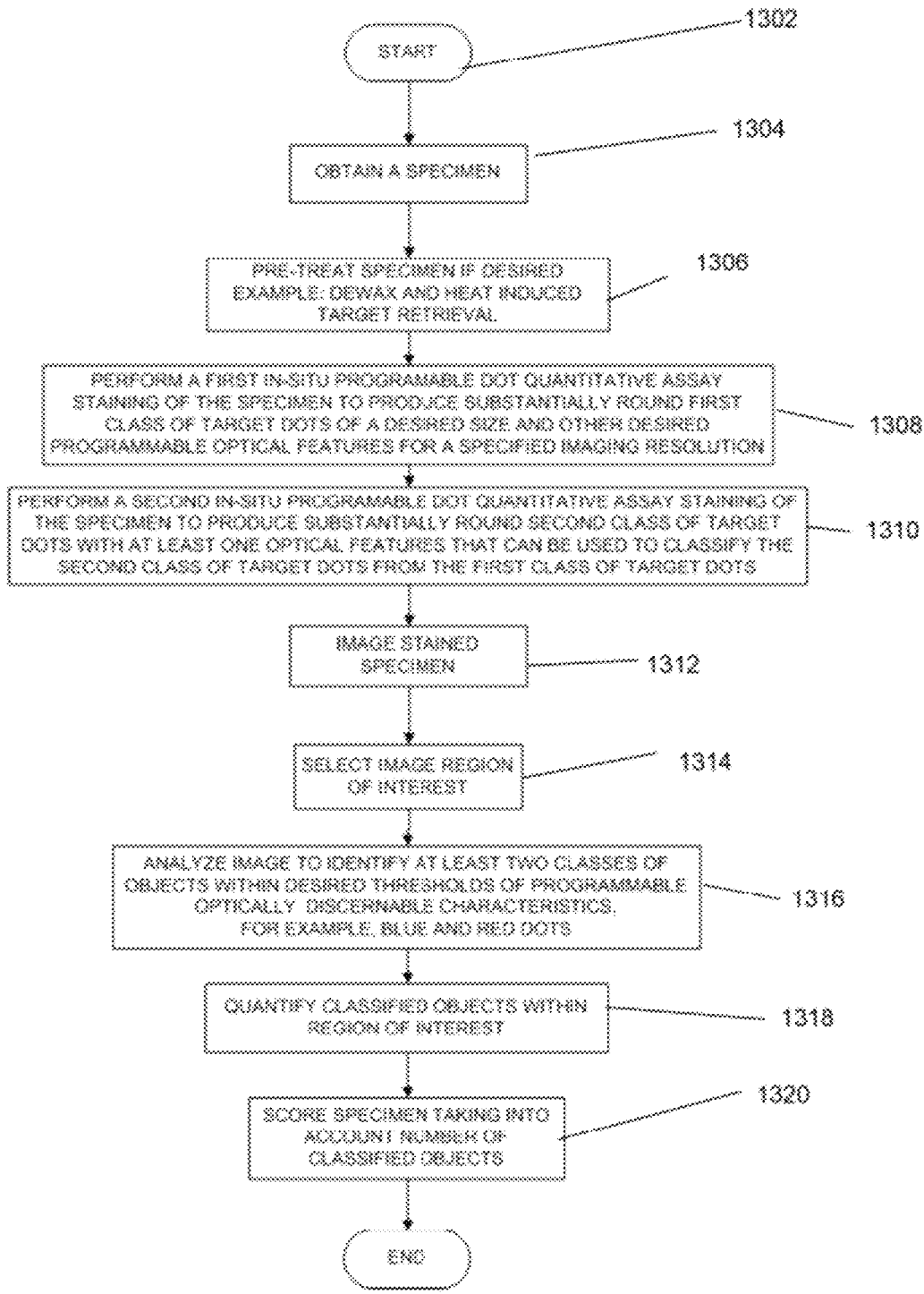
FIG. 13A illustrates process steps of an embodiment of a method of assessing a specimen by performing image analysis to classify and count at least two classes of objects and scoring, taking into account the number of classified objects.

FIG. 13A illustrates process steps of an embodiment of a multiplexed method of assessing a specimen by performing image analysis to classify and count at least two classes of objects and scoring, taking into account the number of classified objects.

An embodiment of method of FIG. 13A is similar to the method embodied in FIG. 4 and described with respect to FIG. 4. In addition to using a programmable dot quantitative assay to process a specimen to detect and produce dots at target sites associated with a single type of molecule, for example Her2, the embodiment includes step 1310, which includes performing a second in-situ programmable dot quantitative assay staining of the specimen to produce a second class of substantially round target dots with at least one optical feature that can be used to recognize the second class of target dots separately from the first class of target dots. Also, the step of analyzing the image 1316 includes identifying at least two classes of objects based on programmable optical features.

Figure 13B:
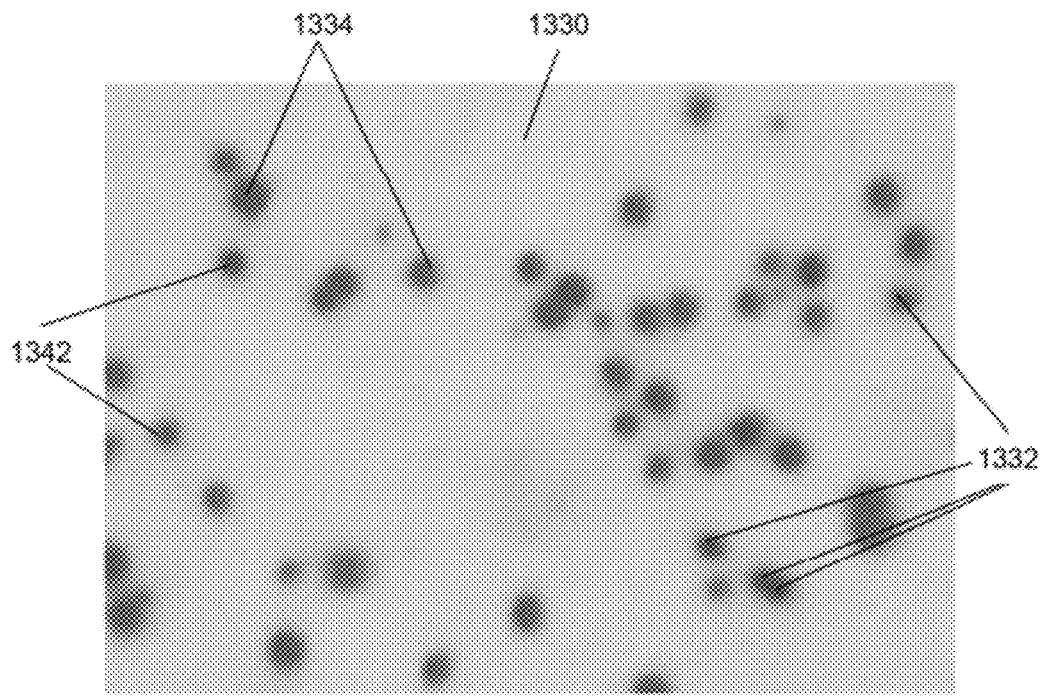
FIG. 13B shows an image of a specimen with target dots and reference dots with optical features (e.g., color) differentiating the target dots and reference dots.

FIG. 13B shows an image of a specimen with multiplexed target dots and reference dots with optical features differentiating a first class of target dots and a second class of target dots. Either a first or a second class of target dots may be reference dots. A first staining step 1308, as illustrated in FIG. 13A, was programmed and performed to produce red dots 1334 at sites of a first target type of molecule, and a second staining step 1310 was programmed and performed, as illustrated in FIG. 13A, to produce blue dots 1332 at sites of a second type of target molecule.

Figure 13C:
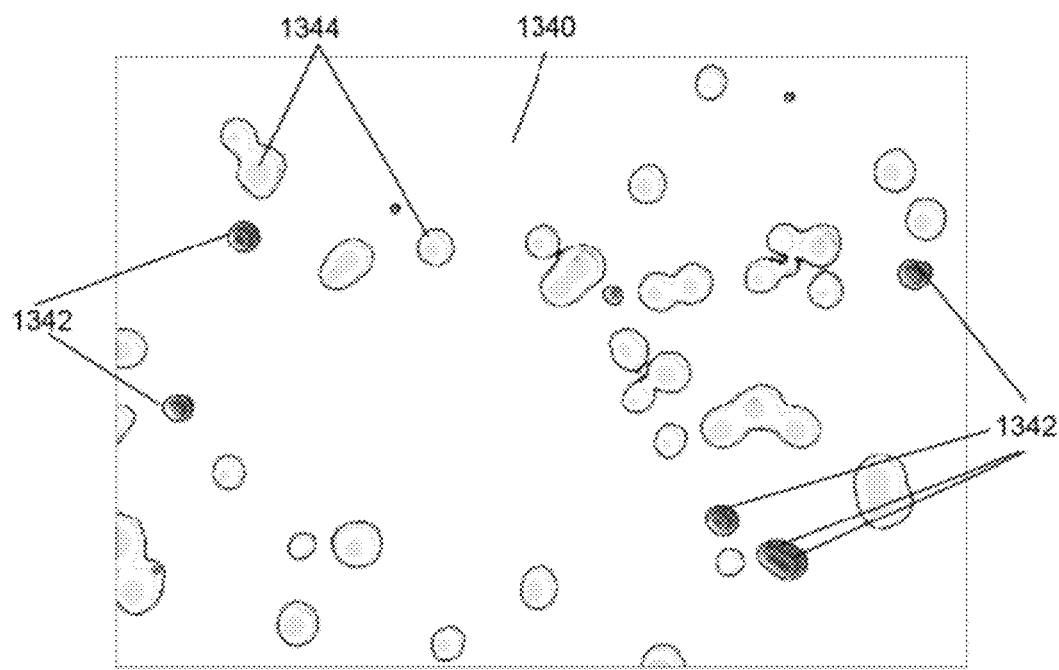
FIG. 13C shows image processing enhancement of contrast between target dots and reference dots, and reduction of background.

FIG. 13C shows a processed image where contrast and gamma settings have been modified in the image analysis software to enhance the contrast between the first class of blue target dots 1342 which appear as darkly filled dots and dot clusters and the second class of red target dots 1344 which appear as lightly filled dots and dot cluster outlines. Image processing may also be used to reduce background color of area 1340 where no cells are present FIG. 13D is an image of an embodiment of multiplexed staining as described in FIG. 12C where the PDQA assay for quantifying her2 protein is performed in accordance with step 1214 and where conventional IHC staining for her2 protein is performed on the same tissue according to step 1216 of FIG. 12C.

Figure 13D:
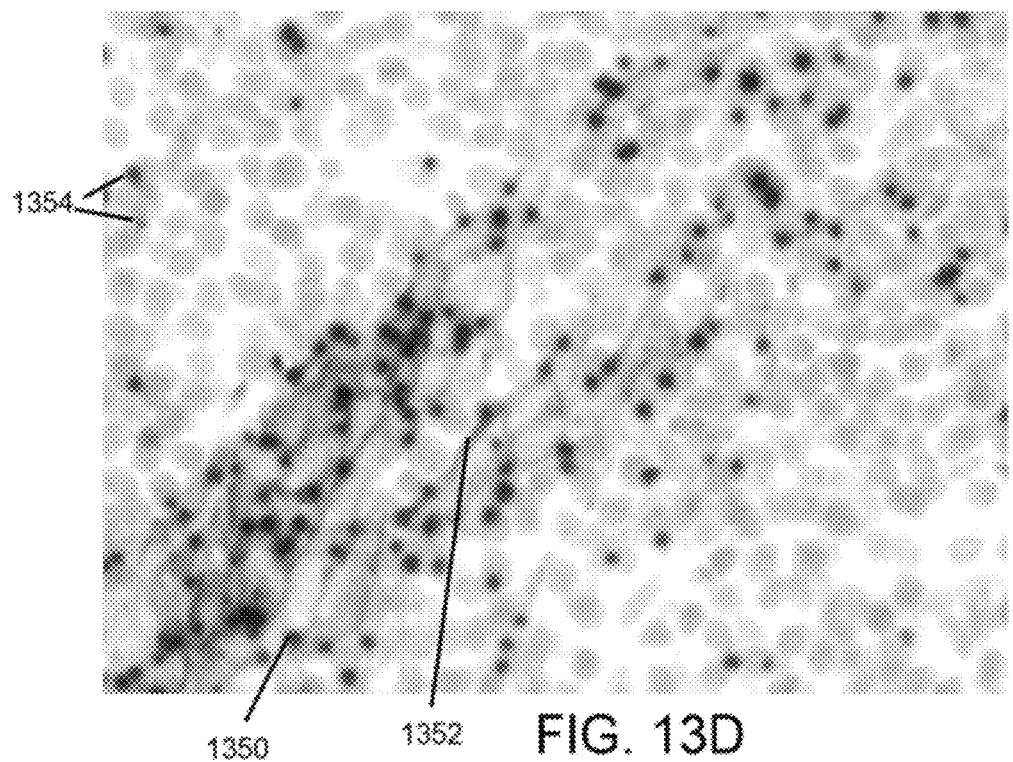
FIGS. 13D and 13E show PDQA dots multiplexed with conventional IHC on the same slide.
Figure 13E:
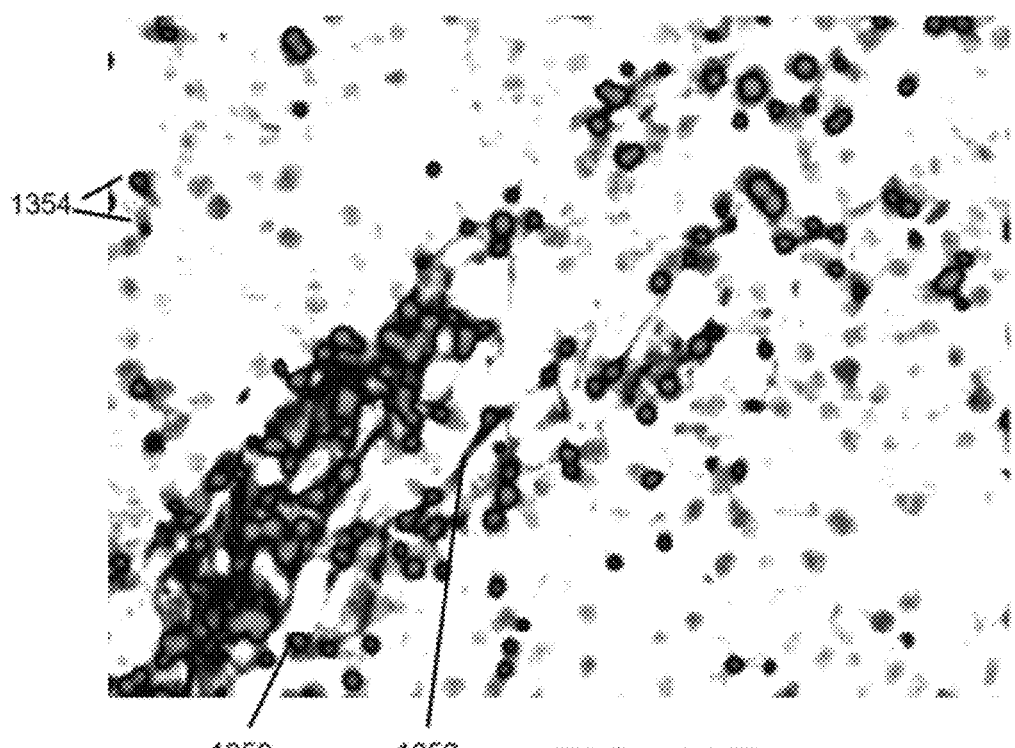

A PDQA dot 1350 produced at the site of a her2 antigen is shown in FIG. 13D and the same dot is show in corresponding image FIG. 13E which has been processed using image processing techniques to enhance the discernability of dots and conventional IHC staining in a grey scale type drawing.

Conventional IHC membrane staining 1352 can be seen on the image of FIG. 13D and corresponding enhanced image FIG. 13E.

This type of multiplexed assessment may be useful for several reasons. For example, one can see that regions of highest PDQA dot density correspond to regions where conventional IHC membrane staining is most visible.

One can also see some PDQA dots such as dots 1354 which appear to be outside the nuclei at locations consistent with where cell membrane and for at which locations no conventional IHC staining is readily apparent. This evidence tends to confirm the principle PDQA dots are discernable in less densely spaced patterns in regions where target expression levels are too low to be readily observable by staining with conventional IHC staining protocols.

Figure 14A:
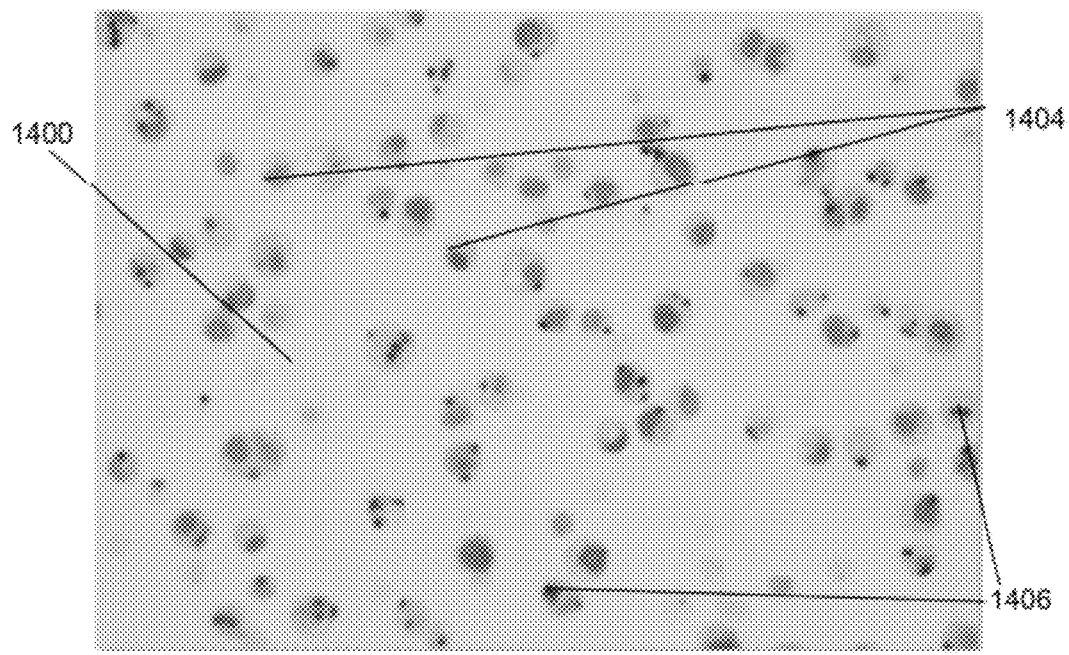
FIG. 14A is an image of a control cell line specimen processed by a programmable quantitative assay.

FIG. 14A is an image of a control cell line specimen processed by a programmable quantitative assay. In this case, a Her2 control cell line is stained; cell nuclei 1404 are counterstained blue and Her2 target molecules are stained by PDQA to produce dots 1406 that are large enough to be optically recognizable.

Figure 14B:
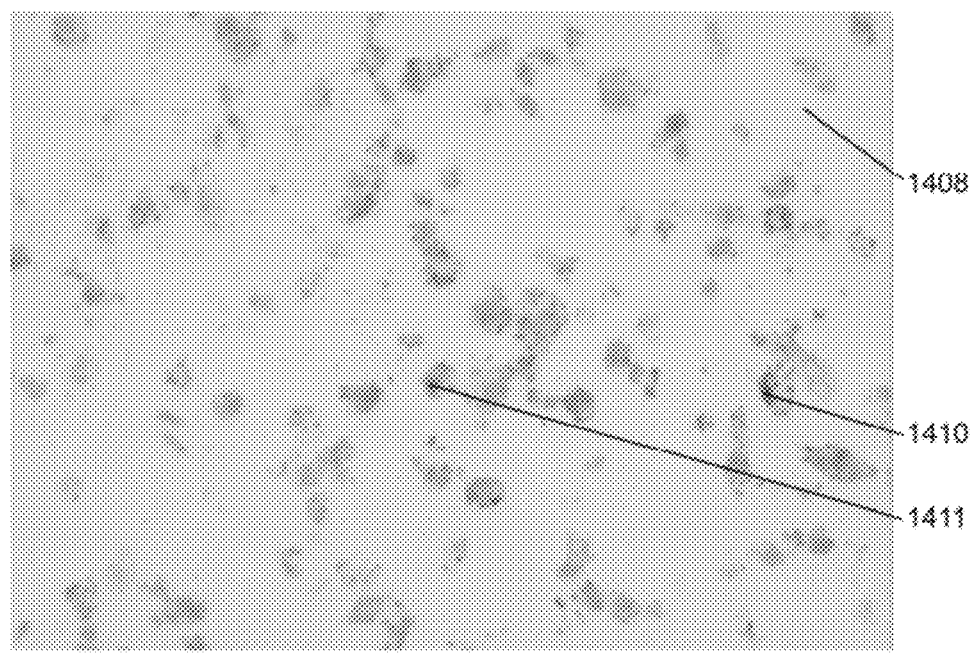
FIG. 14B is an image of a control cell line specimen processed by a proximity ligation assay.

For comparison, FIG. 14B is an image of a Her2 control cell line specimen processed by a proximity ligation assay. The imaging settings are the same as those used to capture the image of FIG. 14A. However, the blobs visible at 1410 and 1411 are not necessarily readily classifiable as single, substantially larger and differently shaped blobs, or alternatively as connected/overlapping blobs.

Figure 15:
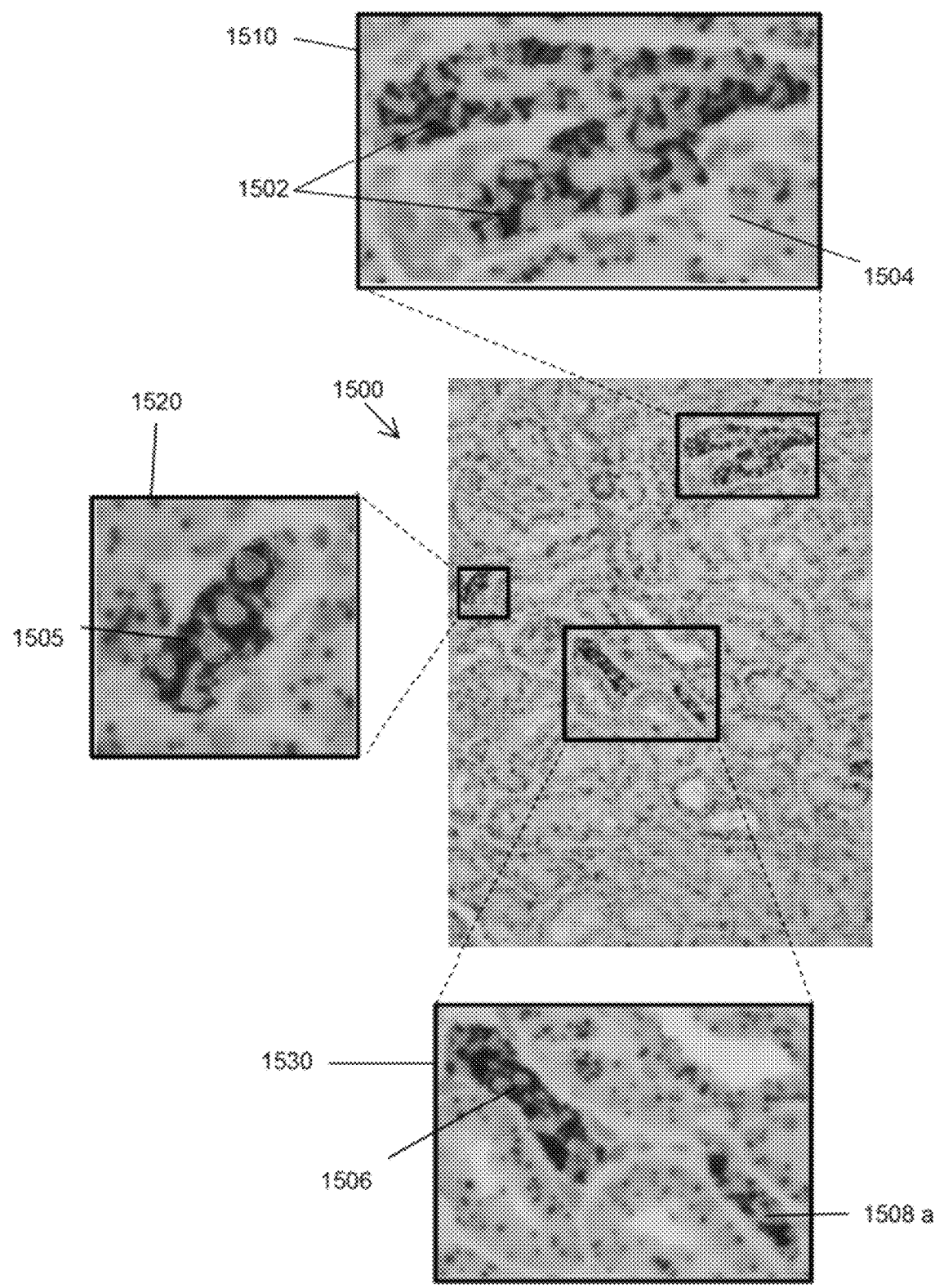
FIG. 15 shows an image of a specimen processed by a programmable quantitative assay and shows enlarged images of cancerous regions where the high target expression levels are highlighted by overlapping dots.

In some embodiments, as shown in FIG. 15, it may be possible to assess regions of interest and also regional levels of target expression with or without any image processing. FIG. 15 shows an image 1500 of a specimen processed by a programmable quantitative assay. Also shown are enlarged images 1510, 1520 and 1530, in which cancerous regions 1502 show high target expression levels and are highlighted by many dark red overlapping dots 1502, 1505, 1506, and 1508. Because the PDQA dots are programmed to have optical features including size, shape, color, etc., large structural components of the specimen may be identified by using geometric object recognition algorithms. As an analogy, in geometric object face recognition, features such as eyes, lips, face outline, etc. may have a predictable range of shapes, sizes, colors, etc. Therefore by analyzing the spatial geometric relationships between recognized objects, i.e., eyes, nose, etc., faces may be algorithmically recognized.

Thus the ability to use geometric object recognition in pathology applications, for example in tissues, may be significantly enhanced by the programmable optical characteristics of PDQA as clearly observable in FIG. 15.

Figure 16A:
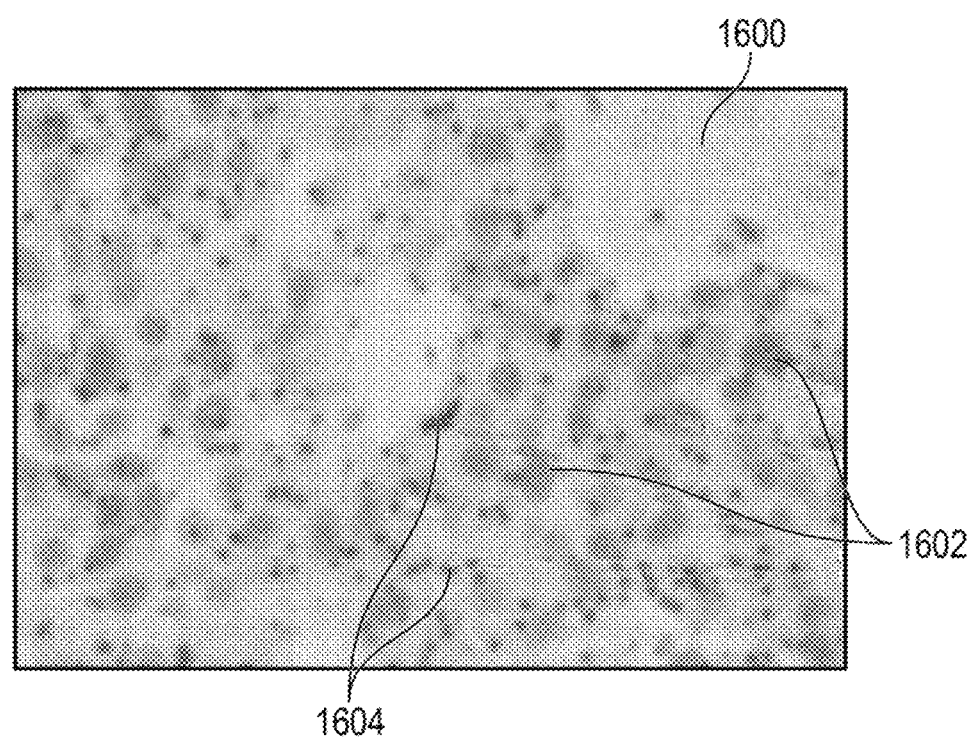
FIG. 16A shows an image of a specimen processed by a programmable quantitative assay with background staining related to counterstaining of cell nuclei.

FIG. 16A shows an image of a specimen processed by a programmable quantitative assay with light blue background staining at 1600 related to dark blue counterstaining of cell nuclei such as at 1602. PDQA dots can also be observed at 1604 in the image of FIG. 16A.

Figure 16B:
FIG. 16B shows an image of a specimen with reduced background processed by an embodiment of an image analysis friendly counterstaining method.

FIG. 16B shows an image of a specimen with reduced background staining, i.e., as shown at 1606. The specimen in the image of FIG. 16 was processed by an embodiment of an "image analysis"-friendly enhanced counterstaining method. In an embodiment of the enhanced counterstaining method, IHC staining is performed for histone targets in the cells to produce relatively even staining. Background staining is reduced because none or few of the histone direct antibodies are found in the areas outside the cells. Use of the enhanced counterstaining method may be combined with staining of targets using PDQA and may result in images that may require less or simpler image processing than H and E counterstaining to enable consistent classification of target objects distinctly from morphological features.

Figure 17A:
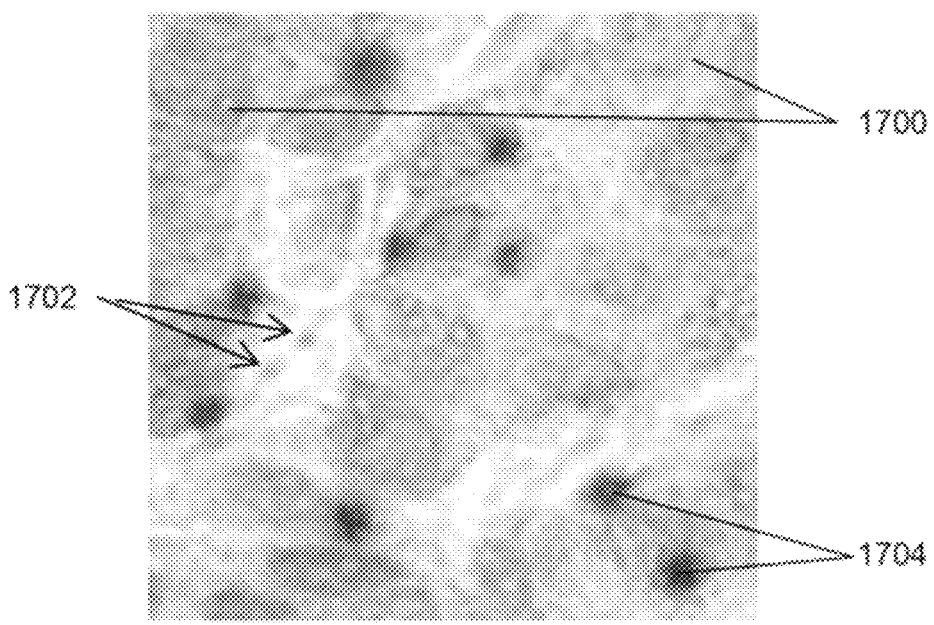
FIGS. 17A-17B show images of a specimen stained by a programmable quantitative assay programmed to exhibit a color shift optical feature.
Figure 17B:
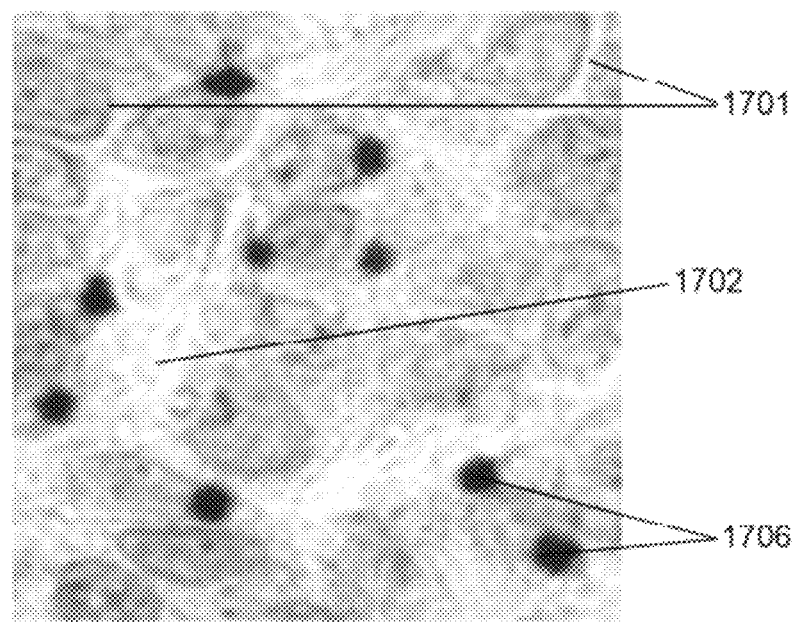

FIGS. 17A-17B show images of a specimen stained by a programmable quantitative assay programmed to exhibit a color shift optical feature. Areas 1700 without PDQA dots have approximately the same hue in the image of FIG. 17A, which was imaged at a focus depth slightly above the "in focus" level, as can be observed in the relative fuzziness of the cell borders at 1700, in contrast to the distinct lines of the same cell borders shown at areas 1701 of the image of FIG. 17B. Certain dark spots 1702 not at sites stained by PDQA can be observed at 1702 in the image of FIG. 17A. Similar spots are not found in the image of FIG. 17B indicating that the focus plane has shifted.

Embodiments of the PDQA may be programmed to produce dots whose color shifts as the focal distance varies. Bright red dots with a dark blue perimeter can be seen at 1704 in FIG. 17A. When imaged at a different focal plane, the dots such as dots 1706 appear dark blue, and neither a bright red center nor a contrasting outer perimeter is visible, as seen in FIG. 17B.

Figure 17C:
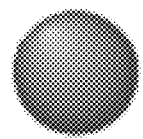
FIGS. 17C-17D illustrate dots programmed to have relatively high and low degrees of sharpness, respectively.
Figure 17D:
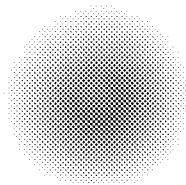

The sharpness of the perimeter of the dots may also be programmed. In embodiments of PDQA, by using short time (in-situ programmable) and high linker concentration (pre-programmed) and high hydrogen peroxide (pre-programmed) in the final staining step, a high edge-contrast staining pattern is obtained, as illustrated in FIG. 17C, and the dots appear of quite uniform intensity with sharp edges and no "halo". On the other hand, the last staining step can be performed in ten minutes with Fast Red, and the edge will be more diffuse with a pale red halo around an intensely red center as shown in FIG. 17D. These more diffuse edged dots may be referred to as having a sloping "Gaussian"-like intensity profile. To the human eye, sharp edged plateaus are appealing, and even very closely spaced dots are clearly separated. To image analysis software, the increasing intensity towards the center of volcanoes could be an additional aid in identifying these since artifacts or particles may also have sharp edges.

Figure 17E:
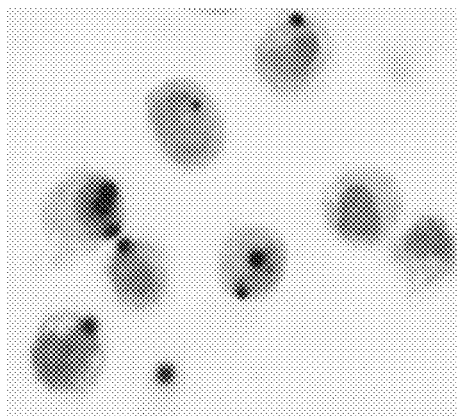
FIG. 17E is an image of PDQA dots programmed to have sharp perimeters and low background.
Figure 17F:
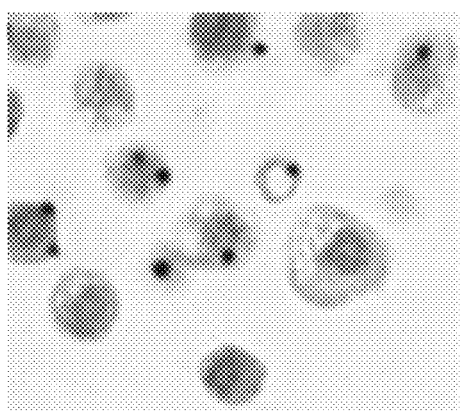
FIG. 17F is an image of PDQA dots programmed to have sharp perimeters.
Figure 17G:
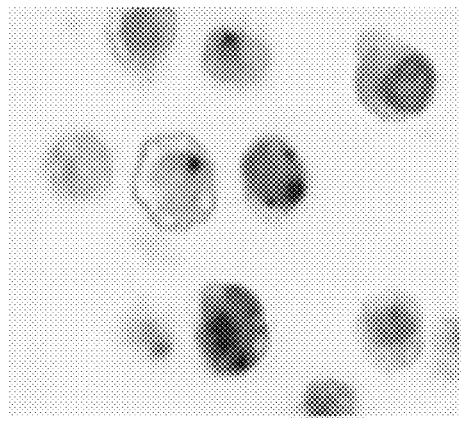
FIG. 17G is an image of PDQA dots programmed to have less sharp perimeters.

FIGS. 17E-17G show the effects of dot programming via cross linker selected. FIG. 17E shows PDQA dots produced with 1 g/L alpha-CHC as cross linker, 5 microM (Fer)4-L150-Flu as reporter, 0.002% hydrogen peroxide, pH 6.8 imidazole buffer, 5 min deposition developed with anti-FITC-alkaline phosphatase followed by Liquid permanent red. When viewed below focus, these PDQA dots exhibit a high degree of ringed diffraction pattern which is optically discernable as a toroidal shape, FIG. 17F show PDQA dots with 0.05 g/L DAB as cross linker 5 microM (Sin)3-150-Flu as reporter, 0.005% hydrogen peroxide, pH 7.4 imidazole buffer 5 min deposition, developed with anti-FITC-alkaline phosphatase followed by Liquid permanent red . . . Dot size and sharpness the PDQA dots shown in 17F is quite similar to the PDQA dots of 17E. However alpha-CHC-crosslinker-based dots of 17E have lower background staining.

FIG. 17G is an image of PDQA dots produced with 0.3 g/L ferulic acid as cross linker, 5 micoM (Fer)4-L150-Flu as reporter, 0.003% hydrogen peroxide, pH 6.8 imidazole buffer, 10 min deposition developed with anti-FITC-alkaline phosphatase followed by Liquid permanent red. The shape of the PDQA dots in FIG. 17G are generally round, however the edge contrast is less pronounced, thus producing a Gaussian intensity profile such as illustrated by FIG. 17D.

FIGS. 18A-18E show a set of images of a specimen processed by a programmable quantitative assay programmed to exhibit a concentric ringedness optical feature.

Figure 18A:
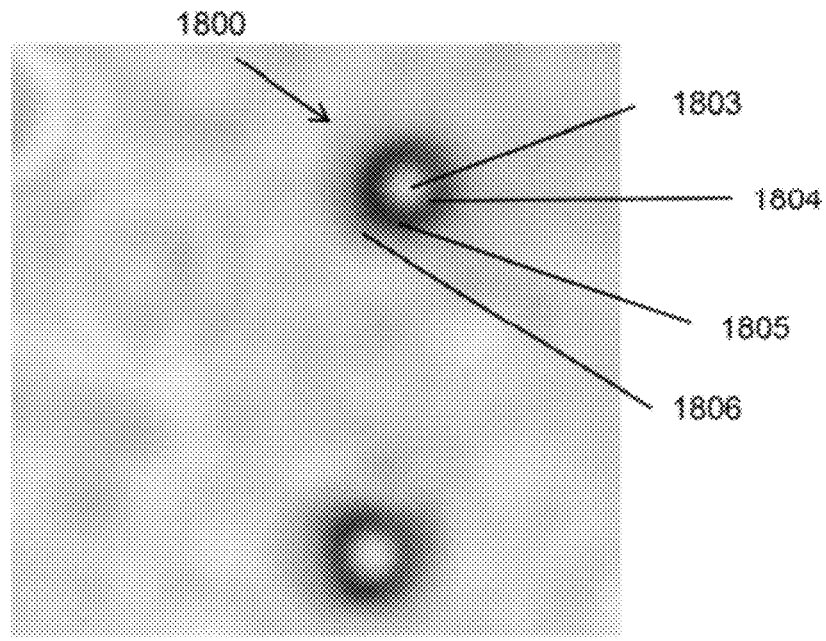
FIGS. 18A-18B show images of a specimen processed by a programmable quantitative assay programmed to exhibit a concentric ringedness optical feature.
Figure 18B:
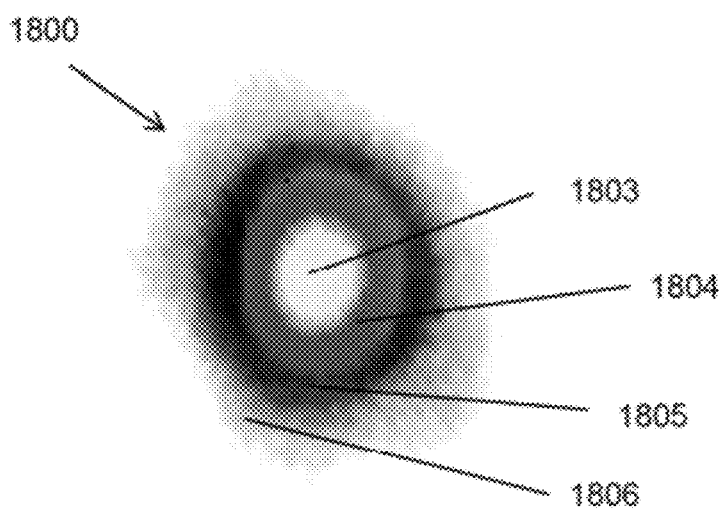

FIG. 18A and FIG. 18B both show an image of a PDQA dot programmed to exhibit a concentrically ringed diffusion pattern. FIG. 18B is an enlarged image of FIG. 18A that has been enhanced to highlight the discernability of the ringed diffraction pattern in grey scale. PDQA dot 18A (seen enlarged and enhance in 18B) is programmed to exhibit a yellowish orange hue center portion 1803 concentrically ringed by a ring exhibiting a reddish hue 1804, which in turn is concentrically ringed by a ring exhibiting a bluish hue 1805. The bluish ring 1805 is surrounded by a diffuse pink halo. Programming of embodiments of PDQA to produce dots which exhibit a concentric ringedness optical feature does not require any additional staining steps to produce the different colors. Rather, the colors are observed for dots programmed to have a pre-determined size range, predetermine hue and predetermined diffuseness.

Figure 18C:
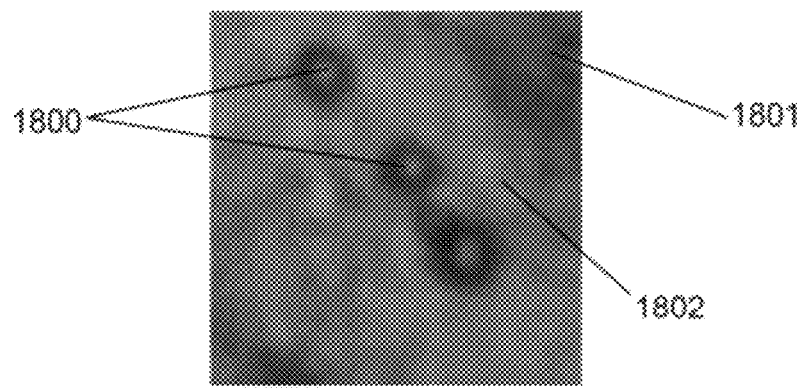
FIGS. 18C-18E show the effect of focus depth on the ringed diffraction feature.
Figure 18D:
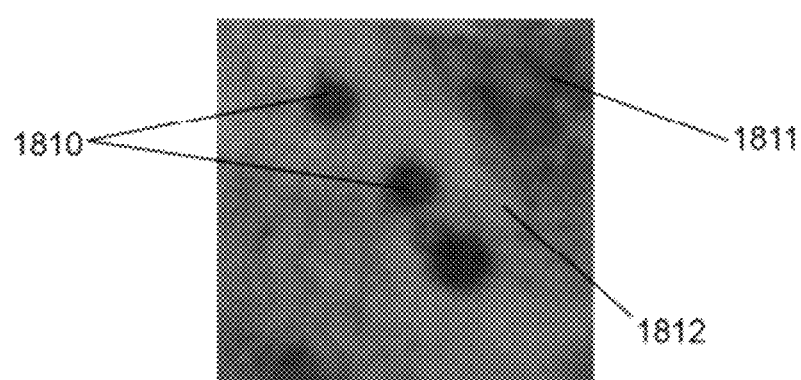
Figure 18E:
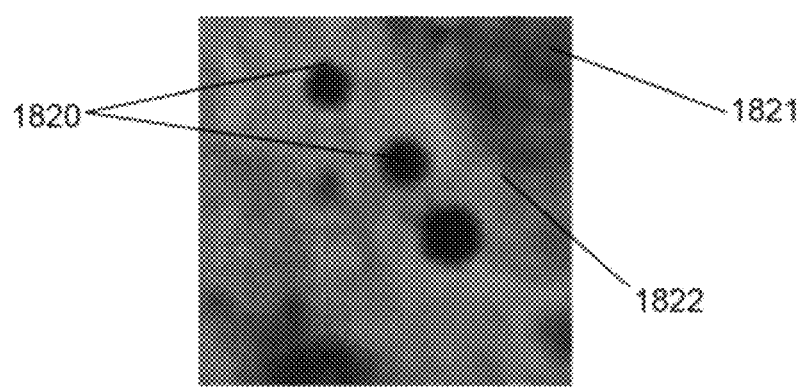

FIGS. 18B-18D provide another view of images of PDQA dots programmed to exhibit the concentric ringedness optical feature or not depending on the focus plane.

Because the PDQA dots may be programmed to have very optically distinct diffraction patterns that vary with the focus plane, in some embodiments this feature may also be used to determine an optimal focus plane, Once a median dot size has been determined, a degree of ringed diffraction over distance may be determined. This enables an inverse calculation to be performed, i.e. finding dots exhibiting ringed diffraction and then calculating the focal distance by knowing the median dot size and the degree of ringedness one may calculate a distance above or below focus. By comparing degrees of ringedness between dots, a vertical distance along the Z-axis between the two dots may also be calculated.

Figure 18F:
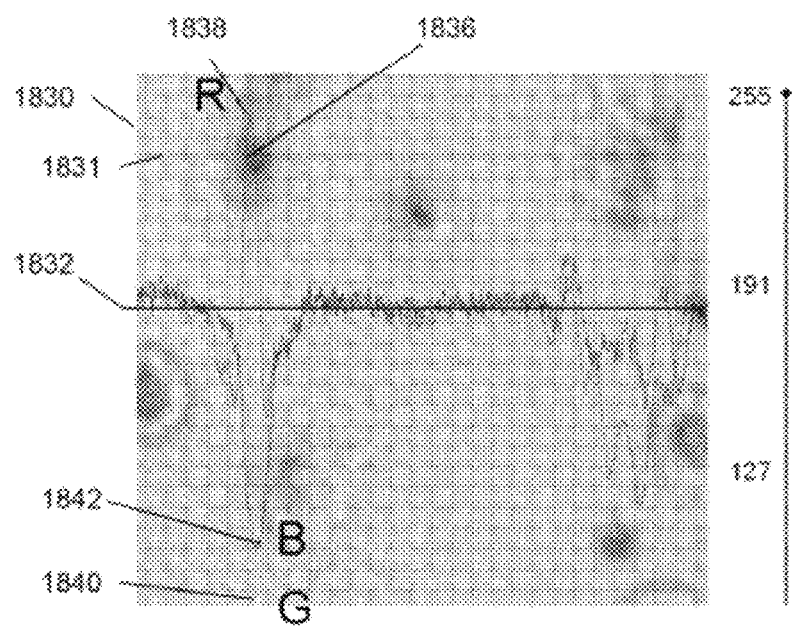
FIGS. 18F-18G show the RGB intensity profile components of PDQA dots exhibiting a ringed diffraction feature.
Figure 18G:
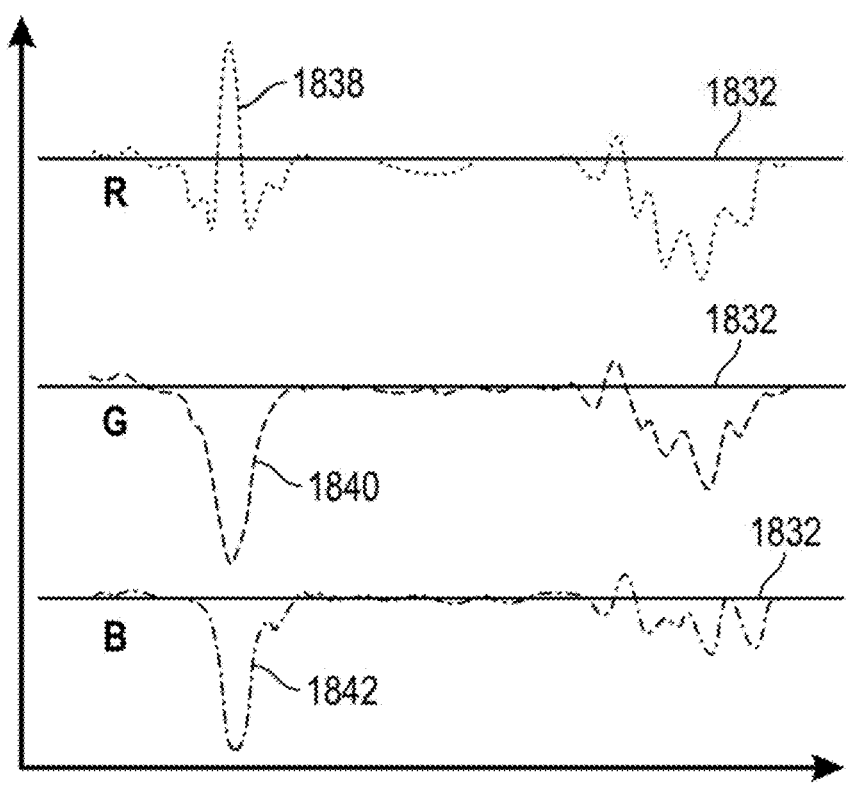

FIG. 18F shows a PDQA dot 1836. A sampling line 1831 shows the y coordinate of the pixels for which intensity levels are superimposed as a graph with intensity values in the range of 0 to 255. FIG. 18G shows a representation of the same image where separate graphs of the intensity levels of the R, G, and B channels are shown.

Figure 18H:
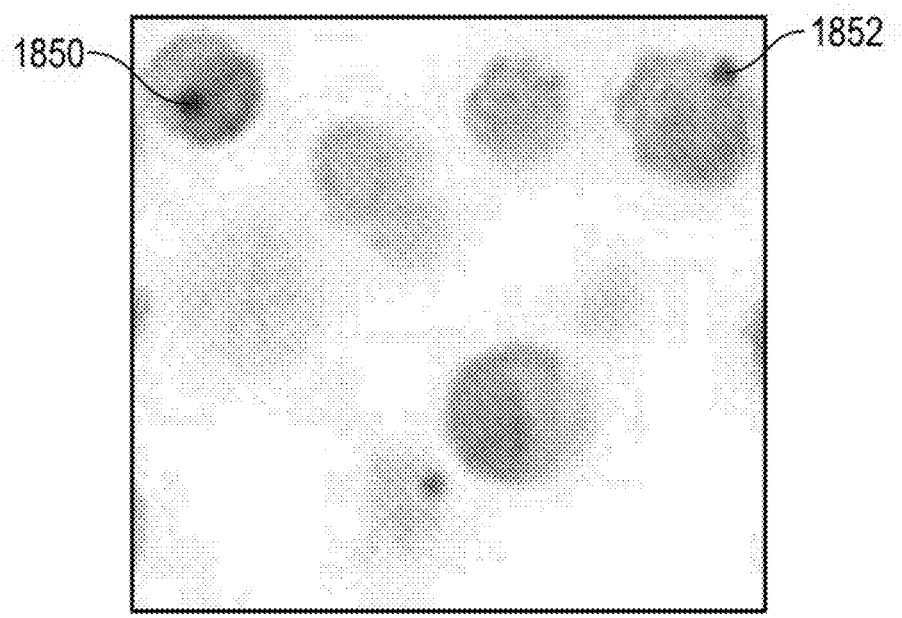
FIGS. 18H and 18I show PDQA dots programmable to produce circular shape dots in brightfield lighting and toroidal shapes.
Figure 18I:
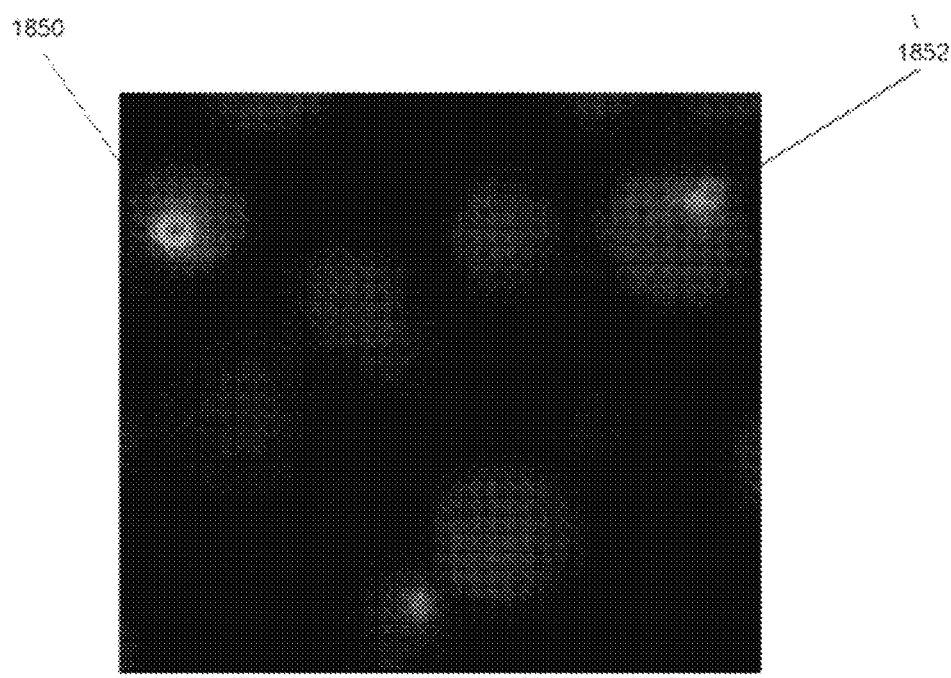

Line 1830 represents the average intensity of "open" or "unstained" area. The intensity of line 1830 is about 187 red, 187 green and 187 red. So one might expect the intensity of pixel where stain is present to be lower (i.e. darker) than the value of unstained tissue or glass. Point 1840 is a minimum point on a graph of the green channel intensity value at the dot origin of dot 1836. The intensity value of green at point 1840 is about 75 out of 255. Point 1842 is a minimum point on a graph of the blue channel intensity value at the dot origin of dot 1836. The intensity value of point 1842 is about 100 out of 255. Point 1838 is the intensity level of the dot origin of PDQA dot 1836. Because the dot has been programmed to exhibit a red-centered diffraction pattern, the level of red at point 1836 is in fact 255 out of 255, significantly higher than the "background intensity level, i.e. level 1832 which is about 187 in R, G, and B channels. FIG. 18H and FIG. 18I are images of breast cancer cell lines on a microscope slide stained using PDQA dots comprising a mixture of red and green fluorophores. FIG. 18H is a brightfield image where PDQA dots 1850 and 1852 have a round shape. FIG. 18I is the same microscope slide where a fluorescent image has been captured. In fluorescent light PDQA dots 1850 and 1852 exhibit a toroid shape. In this case, the toroidal shape results not from a diffraction pattern feature but rather as a result of the dense red fluorophores quenching the less dominant green fluorophores in the center of dots 1850 and 1852.

The dots were produced FFPE sections of HER2 cell lines. Slides were de paraffinated with xylene and ethanol, and target retrieved for 10 min in citrate buffer pH 6 for 10 min in a microwave oven. They were then subjected to the following staining protocol at room temperature on the Autostainer:

Peroxidase block with 3% hydrogen peroxide, 5 min
Wash
antiHER2 antibody 1 microg/mL, 10 min
Wash
4 pM Goat-anti-Rabbit-Dex70-(HRP)10, 10 min
Wash
1 g/L alpha-CHC as cross linker, 5 micoM (Fer)4-L150-Flu as reporter, 0.002% hydrogen peroxide, pH 6.8 imidazole buffer, 10 min.
wash
20 nM anti-FITC-HRP, 10 min
wash
1 g/L alpha-CHC as cross linker, 40 micoM (Fer)4-L150-Flu and 80 microM (Fer)2-L150-Lissamine as reporter, 0.002% hydrogen peroxide, pH 6.8 imidazole buffer, 10 min.
Wash
Mounted with glycerol based antifade with DAPI for fluorescent imaging.

Note that control experiment without 40 microM (Fer)4-L150-Flu in the final deposition mixture produced dots that were indistinguishable purple in bright field, but did not produce any green fluorescent. Omitting instead 80 microM (Fer)2-L150-Lissamine in the final deposition mixture produced very faint yellowish dots in bright field that produced bright filled spherical dots green dots with fluorescence.

Programming the dots to produce such shapes may be utilized in discerning and quantifying different types of dots.

Other multiplexed image processed under brightfield and fluorescent microscope scanners may provide additional benefits. For example, conventional staining of tissue could be combined with fluorescent PDQA dots so that when viewed under a brightfield microscope, staining appears essentially the same as if no PDQA dots had been produced. However, by producing PDQA dots, the dots may be automatically quantified using fluorescent image analysis without impairing or interrupting visual manual interpretation.

Figure 19:
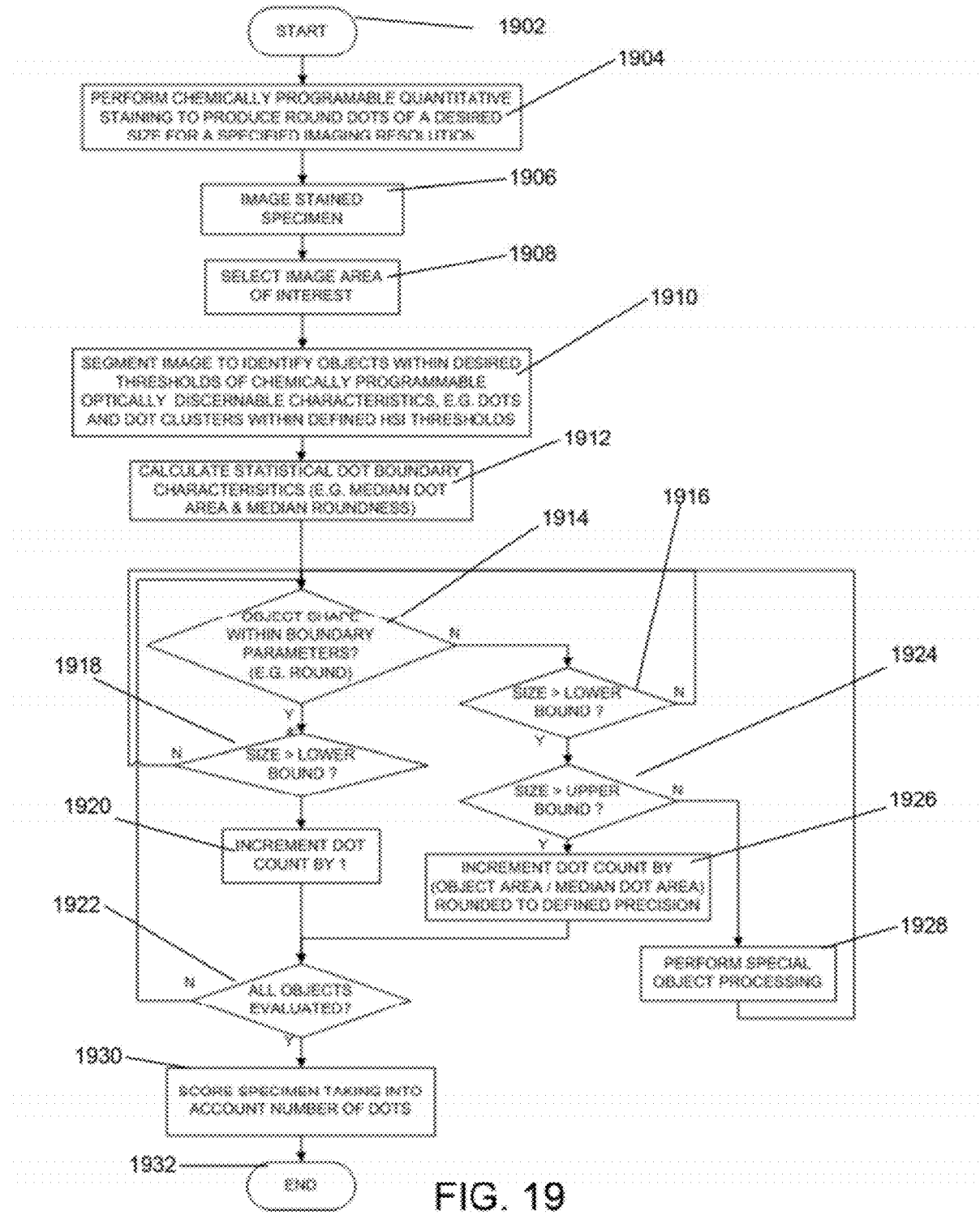
FIG. 19 illustrates process steps on an embodiment of a method of assessing an image by image analysis to classify and count objects and to adjust dot count through use of statistical measures.

FIG. 19 illustrates process steps of an embodiment of a method of assessing an image by image analysis to detect and count objects and to adjust dot count through use of statistical measures. The example illustrated is but one of many potential embodiments. For example in one embodiment, the image is segmented by hue thresholding to identify all red objects which may be classified as dots or dot clusters as shown in step 1910 of FIG. 19. The individual dots can be readily recognized by their roundness, size, intensity, or any combination thereof. Statistical measures such as median values for various optical features can be computed for all of the dots in the image as shown at step 1912. Then these statistical measures can be compared as shown in steps 1914, 1916, 1918, 1922, and 1926 against objects being classified, and appropriate adjustments may made to the dot count as shown in steps 1920, 1926, and 1928.

Figure 20A:
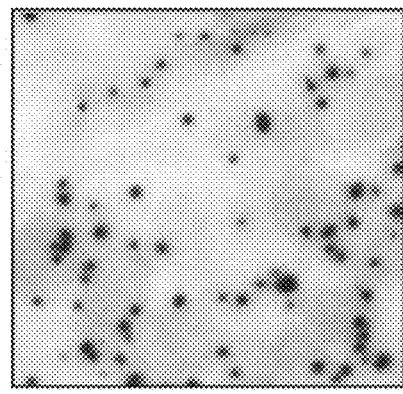
FIG. 20A illustrates an image of a specimen processed by a programmable quantitative assay.
Figure 20B:
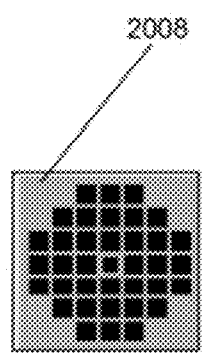
FIGS. 20B-20C show image processing results from an embodiment of an image processing method using a round structuring element.
Figure 20B:
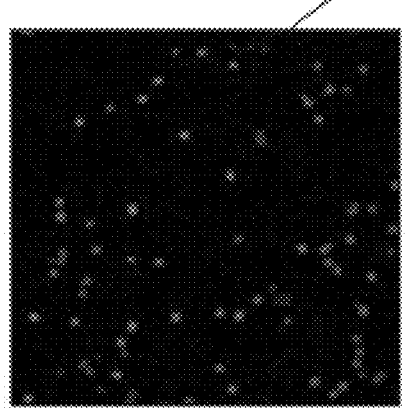
Figure 20B:
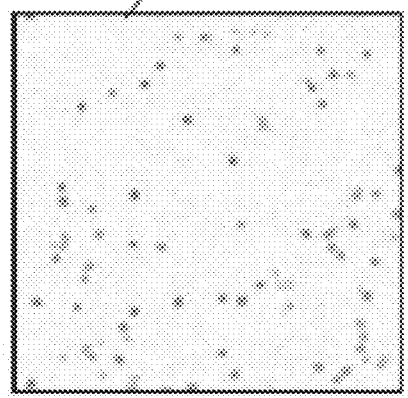
Figure 20C:
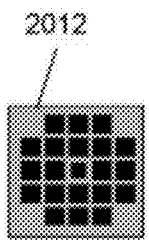
Figure 20C:
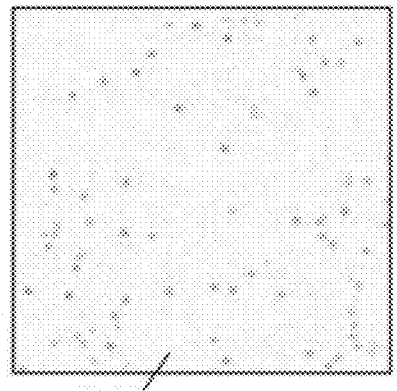

FIG. 20A illustrates an image 2002 of a specimen processed by a programmable dot quantitative assay. FIGS. 20B-20C show a processed version of image 2002 from an embodiment of an image processing method using a round structuring element 2008 or 2012. Intermediate image processing results 2004 and 2010 show that this method of image analysis is effective for dots with a programmed size and shape that is appropriate for the structuring element. Images 2006 and 2014 show that different size dots may be recognized and classified.

Figure 21A:
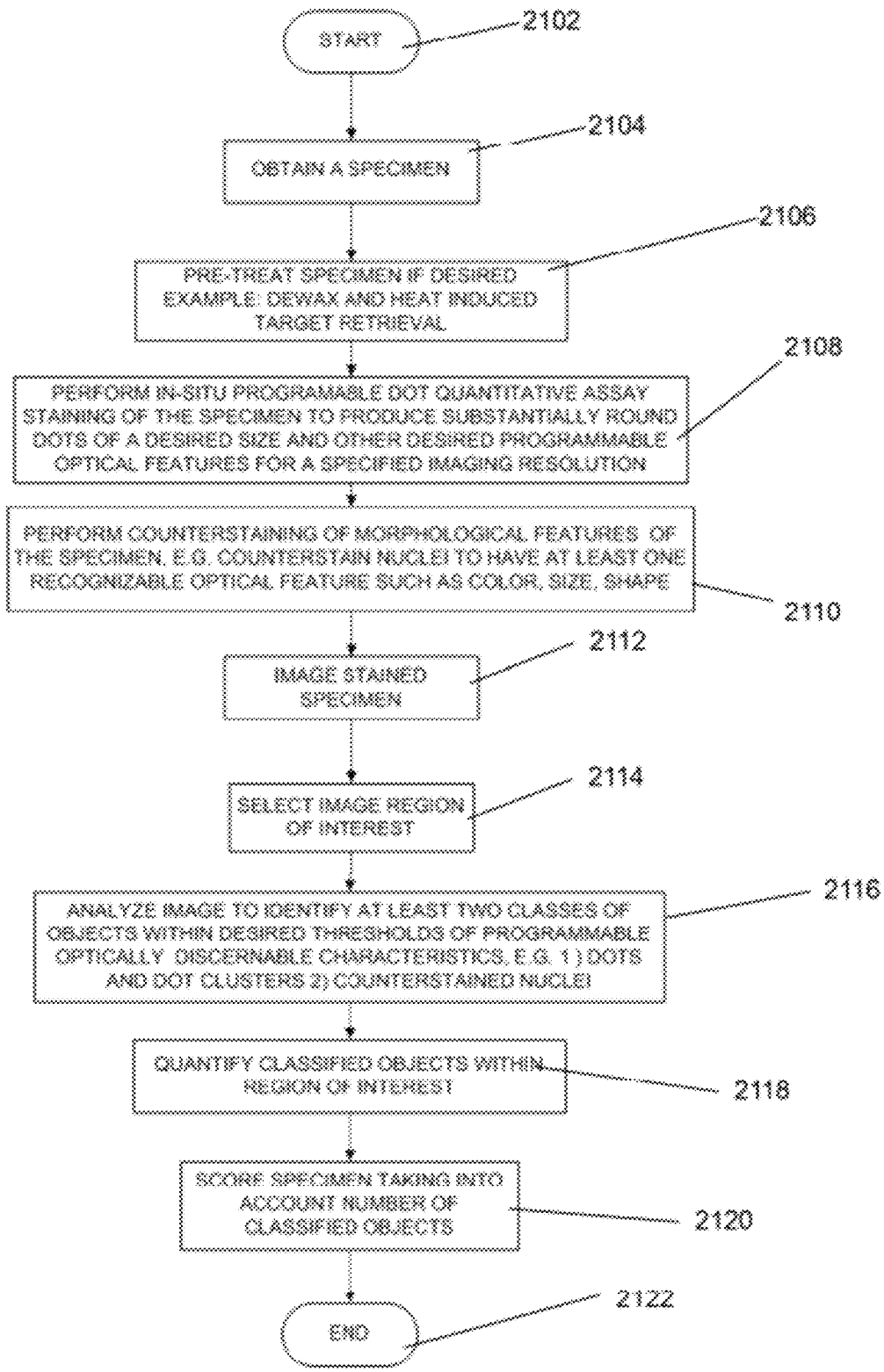
FIG. 21A illustrates process steps for a ratiometric embodiment of method of imaging target dots and reference dots for robustness and quality control under varying pre-analytical processing conditions.

FIG. 21A illustrates process steps for a ratiometric embodiment of a method of imaging target dots and reference dots for robustness and quality control under varying pre-analytical processing conditions. For example at step 2106, a pre-treatment step may be performed, for example, dewaxing a formalin fixed paraffin embedded tissue specimen, or performing heat induced target retrieval on a paraffin embedded tissue specimen.

However, in some embodiments, while a pre-treatment may be advantageous for conventional IHC staining, it may be skipped in some cases with the highly sensitive programmable dot quantitative assay since some target molecules are typically available even without heat induced target retrieval. For example, a room temperature PDQA staining directed at widely present target molecules such as cytokeratin could be combined with routine H&E staining and performed on all slides as they enter a lab. The programmable time and sensitivity of PDQA could be programmed to match the timing required for H&E staining and the results could be analyzed as a method of measuring whether the degree of fixation of a specimen is appropriate. Time and temperature of the steps for producing the dots may vary, but advantages of many of the embodiments of the invention are that time and temperature requirements for PDQA may be very similar to those for conventional IHC (i.e. they can all be performed at a single temperature e.g. room temperature and within a relatively short time period e.g. less than 100 minutes.

Moreover as illustrated in FIGS. 21B and 21C, embodiments of PDQA may be used to implement a ratiometric embodiment of method of analyzing an image with target dots and reference dots for robustness and quality control. Red target dots such as dots 2102 may be produced with a first PDQA staining and blue reference dots such as dots 2103 may be produced with a second PDQA staining. Under normal pre-analytical processing conditions, for example, normal target retrieval is performed to verify that the specimen has been formalin fixed appropriately. In FIG. 21B there are 14 red targets, such as dots 2102, and 6 blue reference dots, such as dots 2103, illustrated within high expression region 2105. Thus the ratio of 14 target dots to 6 reference dots may be represented as a fraction 14/6 or a decimal 2.333. FIG. 21C illustrates the same specimen which has been either over fixed or under retrieved during the pre-analytical processing. Over fixation and under retrieval can both produce the result that a certain portion of molecules are crosslinked and not bound by an assay's antibodies. Thus, when the antibodies are amplified and produce dots using the programmable dot quantitative assay, a smaller number of dots will be produced for the same concentration and protocol of PDQA. For example, if half of the dots are suppressed, i.e., not produced, the ratio of the 7 red dots, such as dots 2107, to the 3 blue dots, such as dots 2016, is 7/3 or 2.333, assuming that the effect of the pre-analytical steps, such as fixation and/or target retrieval, is the same for the target molecules as for the reference molecules. Even if the effect differs, a calibration curve may be generated, which enables one to determine a dot count adjustment for the target dots based on the number of reference dots within the region.

Figure 22:
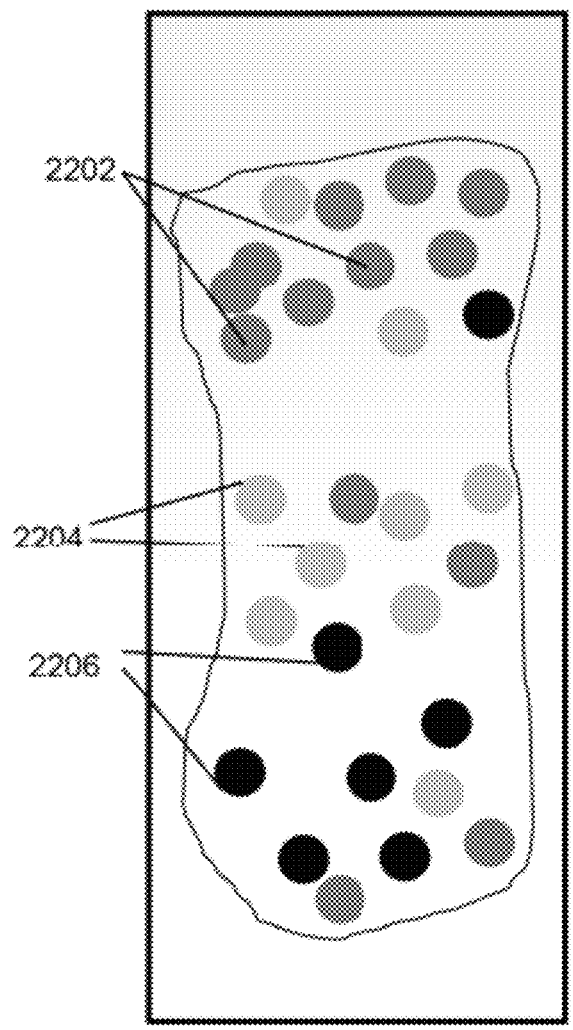
FIG. 22 illustrates a method of imaging analyzing images of specimens processed by a programmable quantitative assay programmed to produce dots of multiple programmed colors corresponding to multiple targets.

FIG. 22 illustrates a method of imaging analyzing images of specimens processed by a programmable quantitative assay programmed to produce dots of multiple programmed colors corresponding to multiple targets. Besides producing PDQA dots of two colors as demonstrated in the image of FIG. 13B, a plurality of PDQA dot classes can be produced by performing multiple staining steps, each with a desired programmed color. PDQA has been programmed to produce brown dots like dots 2204 as illustrated in image 2210 of FIG. 22, red dots like dots 2202, blue dots like 2206, and so forth including black, purple, and yellow dots. Additional colored dots may be produced by using different chromogens.

In some embodiments, each programmed color may be associated with a different target molecule type. Alternatively, a single target molecule type may be stained multiple times with PDQA staining programmed each time to produce a dots with different optical features. For example staining with a low concentration of primary antibody with PDQA amplification programmed to produce a first color could be followed by a second antibody at high concentration and a second PDQA staining to produce dots of a second color and so forth. One application of such an embodiment may be to produce a multicolored heat map showing for example red PDQA dots produced in regions of abundant target expression bound by a low concentration of primary antibodies, followed by blue dots at medium expression regions and so forth.

Figure 23:
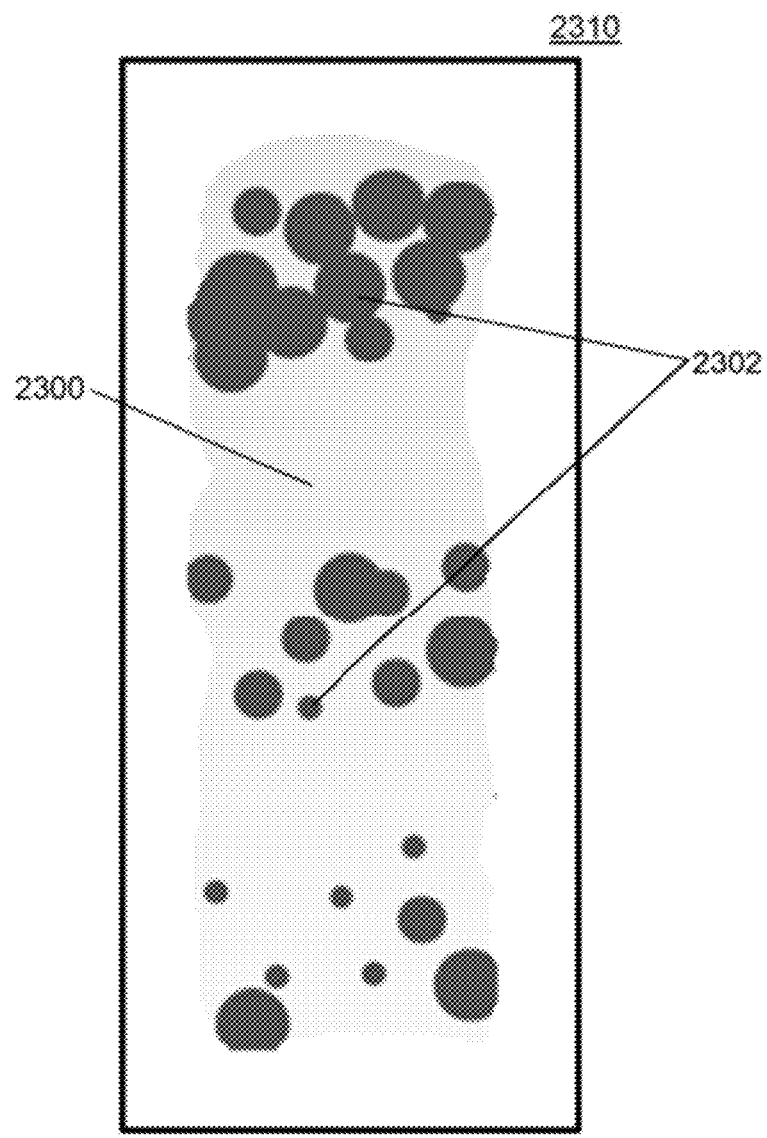
FIG. 23 illustrates a method of imaging analyzing images of specimens processed by a programmable quantitative assay programmed to produce dots of multiple programmed sizes corresponding to multiple targets.

FIG. 23 illustrates a method of imaging analyzing images of specimens processed by a programmable quantitative assay programmed to produce dots 2302 of multiple programmed sizes corresponding to multiple targets.

Figure 24A:
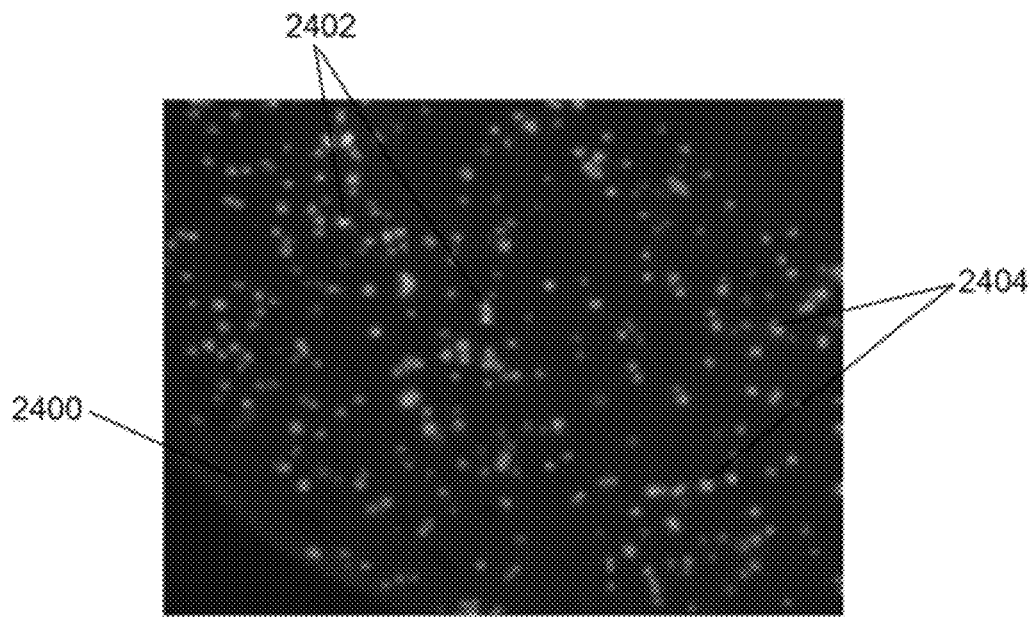
FIGS. 24A-B show an image of a specimen stained by red and green quantitative fluorescence assays providing evidence that the programmable dots are each attached to a single target molecule.
Figure 24B:
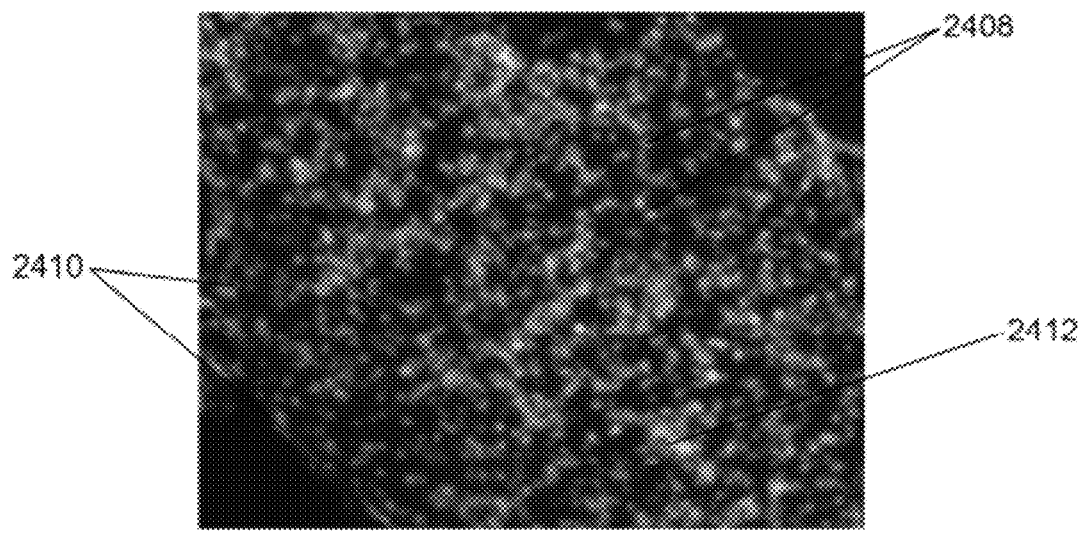
Figure 25A:
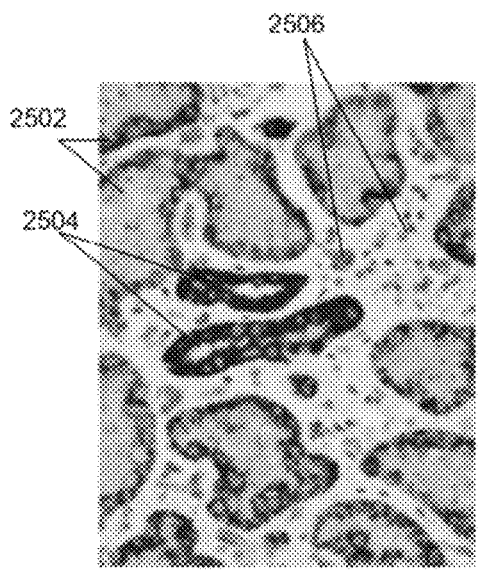
FIGS. 25A-25D show images of a specimen processed four times using decreasing concentrations of secondary tagged antibodies with a programmable quantitative assay.
Figure 25B:
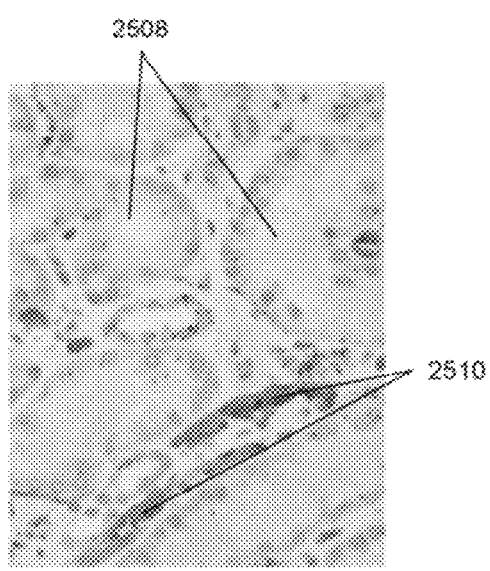
Figure 25C:
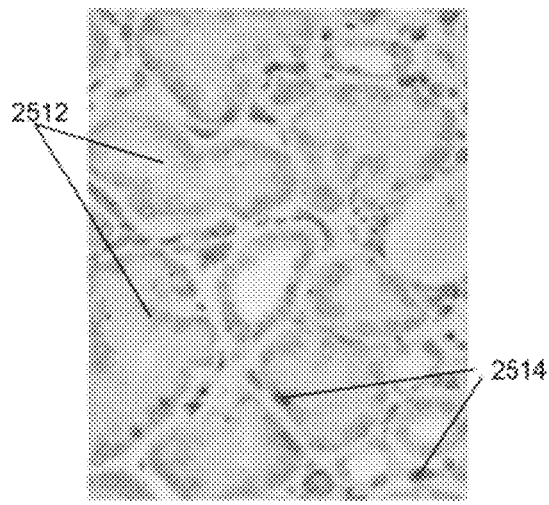
Figure 25D:
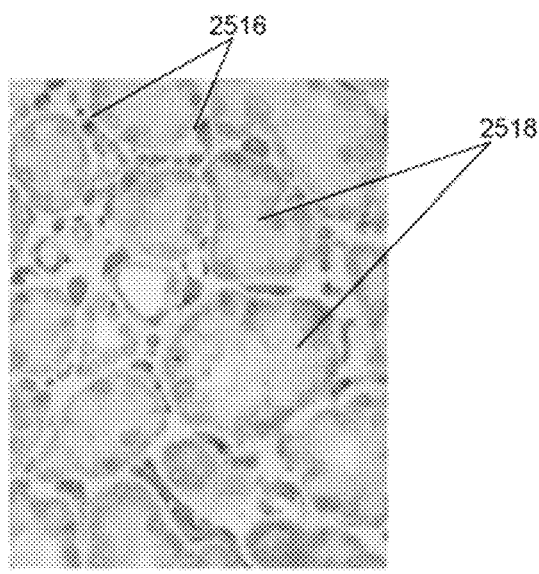

FIGS. 24A-B show an image of a specimen stained by red and green quantitative fluorescence assays providing evidence that the programmable dots are each attached to a single target molecule. Additional detail regarding these experiments is provided in the Additional Examples and Embodiments section.

FIGS. 25A-25D show images of a specimen processed four times using decreasing concentrations of secondary tagged antibodies with a programmable quantitative assay. Additional detail regarding these experiments is provided in the Additional Examples and Embodiments section.

Figure 26:
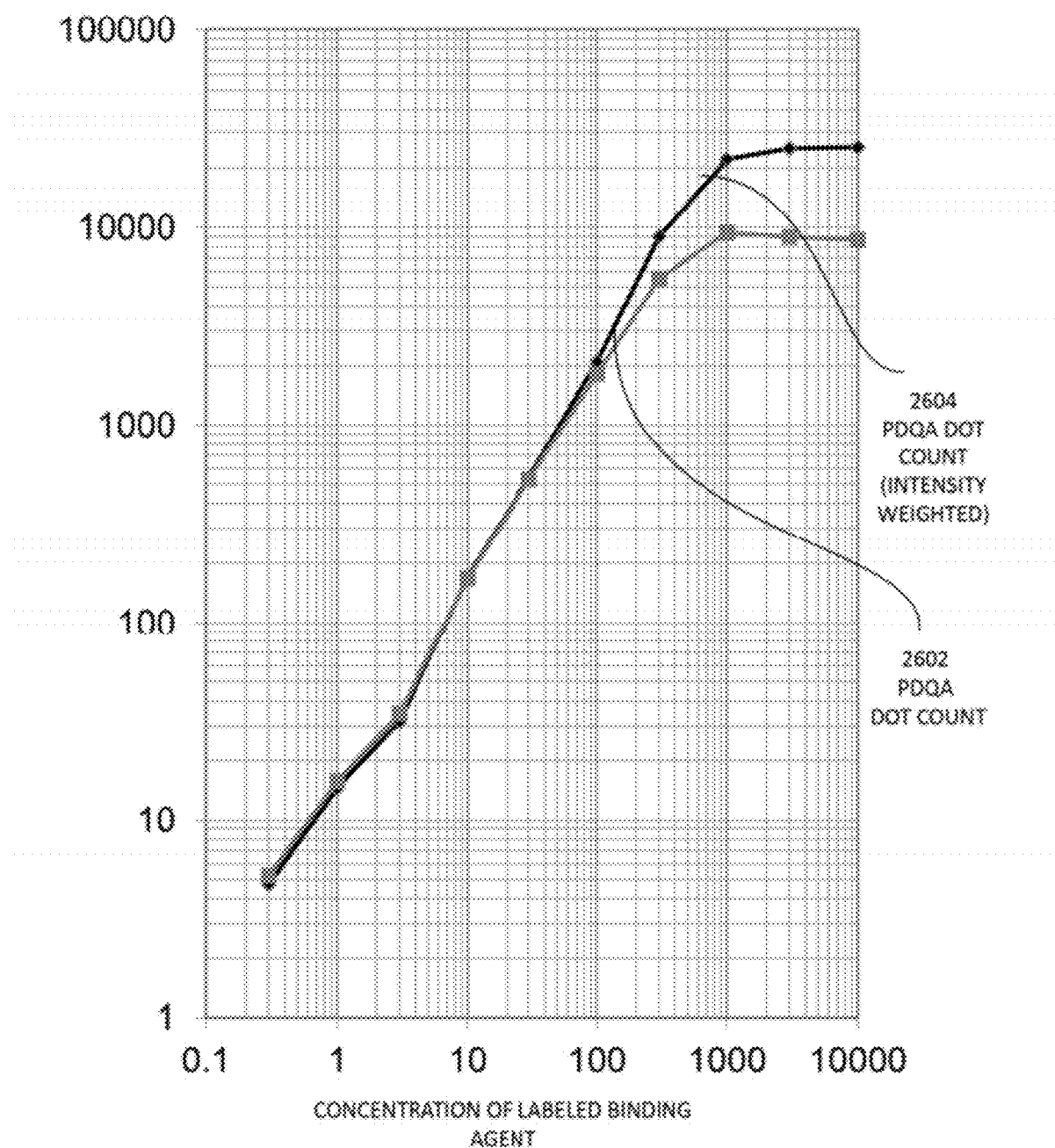
FIG. 26 illustrates linearity of dot counts and dot intensity produced using an embodiment of a method of image analysis of a specimen processed by a programmable quantitative assay.

FIG. 26 illustrates linearity of dot counts and dot intensity produced using an embodiment of a method of image analysis of a specimen processed by a programmable quantitative assay. As FIG. 26 illustrates, the PDQA dot count 2602 increases proportionally to the increase in concentration of the labeled binding agent used in the processing. The proportional increase of the PDQA dot count 2602 levels off at high concentrations of labeled binding agent, an effect which may be caused by dots overlapping as their number and density increases with the increasing concentration of the labeled binding agent. This effect may be balanced by performing an intensity weighted count of the dots, which may more accurately account for overlapping dots. Thus, the intensity weighted PDQA dot count 2604 exhibits proportional increase with increasing labeled binding agent concentration over a greater concentration range of labeled binding agent. Additional detail regarding this embodiment is provided in the Additional Examples and Embodiments section.

Figure 27:
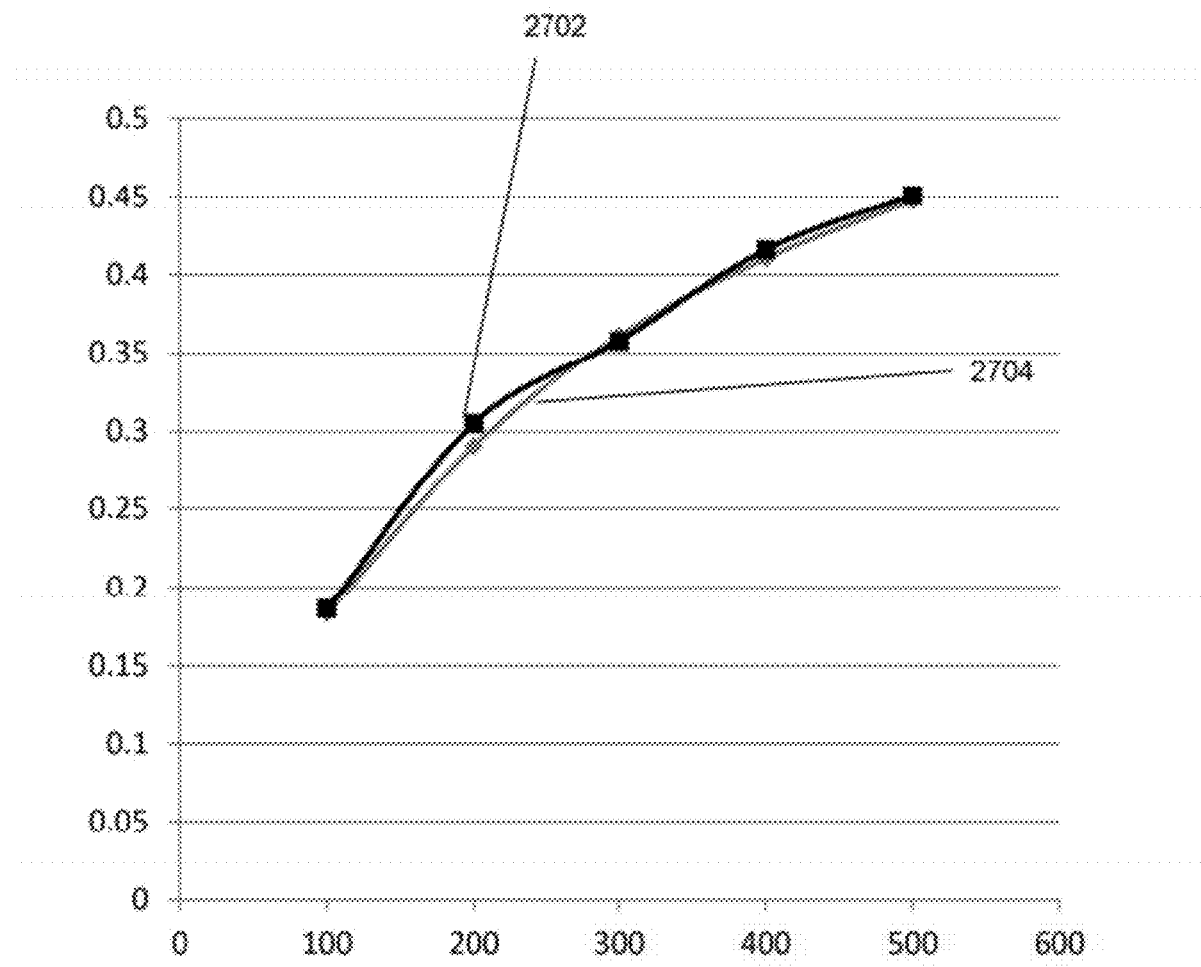
FIG. 27 shows a graph comparing predicted numbers of dots per cell versus measured numbers of dots per cell.

FIG. 27 shows a graph comparing predicted numbers of dots per cell versus measured numbers of dots per cell. The chart shows that the predicted dot count 2704 corresponds to the actual dot count 2702. Additional detail regarding this experimental data is provided in the Additional Examples and Embodiments section.

Figure 28A:
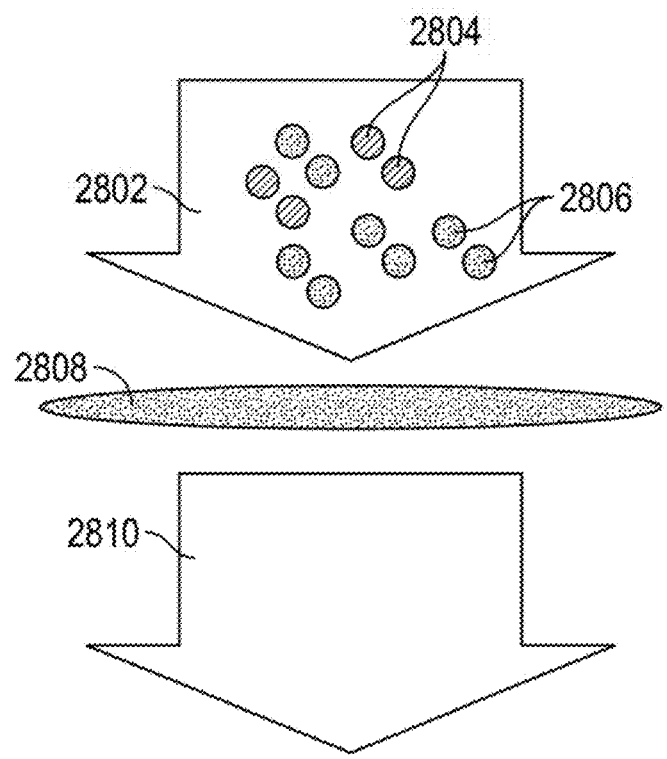
FIGS. 28A-28B depicts an embodiment of performing image analysis of a specimen produced by passing a liquid through a porous substrate and then processing the specimen-carrying substrate by a programmable quantitative assay.
Figure 28B:
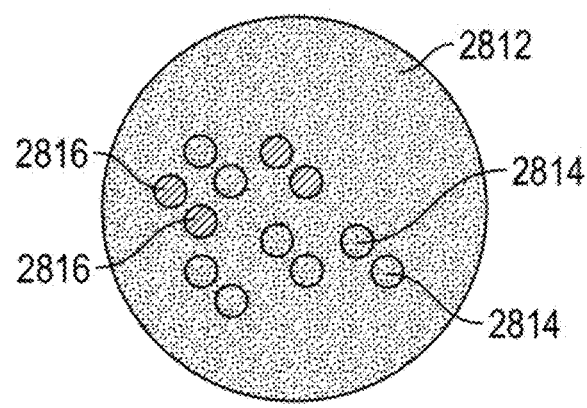

FIGS. 28A-28B depict an embodiment of performing image analysis of a specimen produced by passing a liquid 2802 comprising at least one first target 2804 and optionally at least one second target 2806 through a porous substrate 2808 and then processing the specimen-carrying substrate by a programmable quantitative assay using embodiments and methods described above and in the Additional Examples and Embodiments section with respect to various specimen type. Specimen 2802 and first target molecules 2804 and second target molecules 2806 need not be biological specimens and targets or even organic. Any substance to which a binding agent may be bound can be used to implement various embodiments of PDQA imaging, so long at the effective chemical compounds may be conjugated or otherwise linked to the binding agent. Further discussion of these aspects of the invention may be found in the Additional Examples and Embodiments section.

Figure 29:
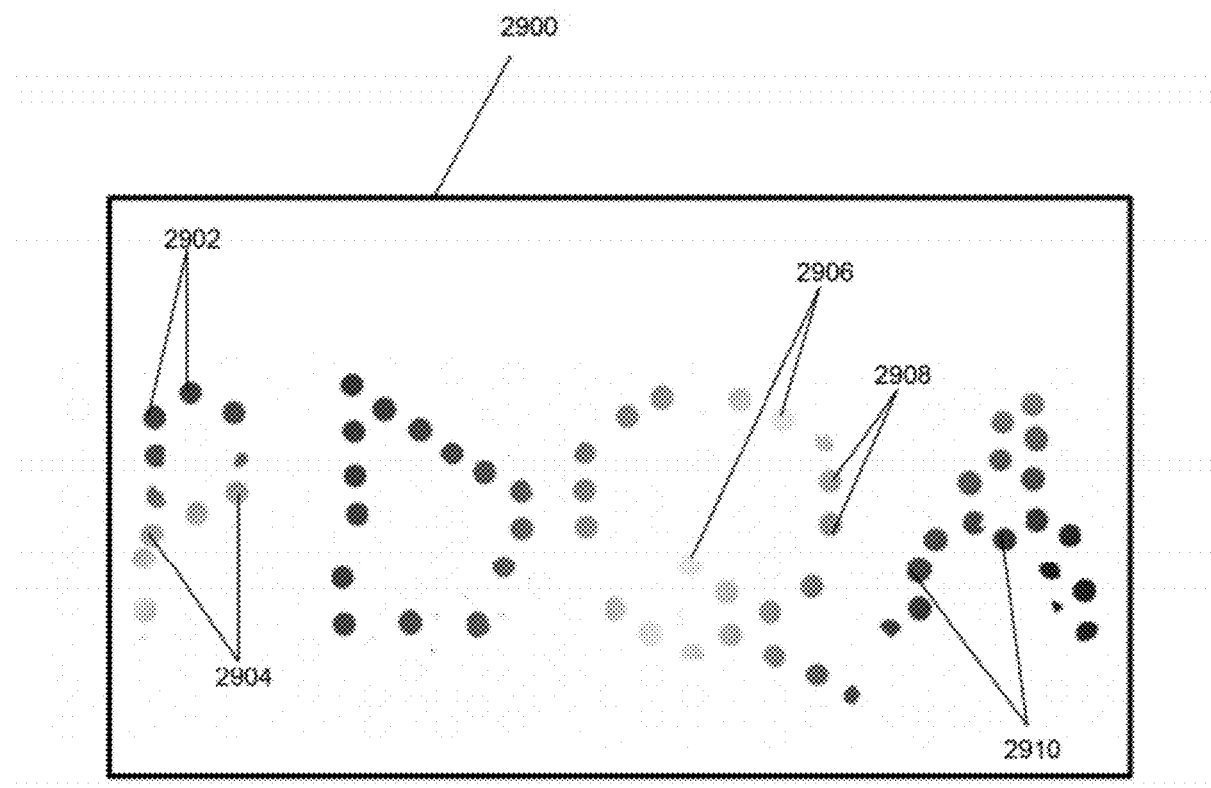
FIG. 29 depicts an embodiment of image analysis results of processing biochemical encrypted printing using detectable markers by a programmable quantitative assay.

FIG. 29 depicts an embodiment of image analysis results of processing biochemical encrypted printing using detectable markers by a programmable quantitative assay. Since the optical features of PDQA include colors, biomicroprinting or biomicroencryption may be performed using PDQA and appropriate image analysis techniques. For example, target molecules of a single type or of different type could be deposited on a substrate 2900 which could be a piece of paper, or any solid substrate. The target molecules could be deposited in a desired arrangement, for example by an inkjet printer using target molecule solutions of different types in place of ink. Substrate 2900 could then be processed by a programmable dot quantitative assay so as to produce dots with desired optical features such as red dots 2902, orange dots 2904, yellow dots 2906, green dots 2908 and blue dots 2910. Other optical features such as size, degree of dot overlap, etc., may also be programmed to suit any desired application. Since the dots are may appear invisible even under microscopic magnification until they have been processed with an antibody or other binding agent to the target molecules, only someone who knows the proper antibody or binding agent to use would be able to decrypt the information.

ADDITIONAL EXAMPLES AND EMBODIMENTS

The term "sample" may mean a representative part or a single item from a larger whole or group, an amount or portion of a matter or object that may contain a target to be detected, e.g. a portion or amount of biological, chemical, environmental material comprising a target molecule, particle, structure to be analyzed, e.g. a biopsy sample, a food sample, a soil sample, etc. A sample may show what the rest of the matter or object is or should be like. A sample may be, for example, a sample from a biological specimen, an environmental sample, e.g. a sample of a soil or a sample of a spillage, a food sample, and a portion of a library of organic molecules.

A biological sample may be a sample including suspended cells and/or cells debris, e.g. blood sample, suspension of cloned cells, body tissue homogenate, etc; a sample including intact or damaged cells of an animal body, a body tissue, smear or fluid or a sample of a tumor, e.g. a biopsy sample; a fresh tissue sample or preserved tissue sample, e.g. a formalin fixed paraffin embedded tissue sample; a sample including a living organism, e.g. a sample of a medium including an animal, plant, bacterium, fungi, etc; a sample including viral particles, debris thereof, or viral products, e.g., a body smear including viral nucleic acids, proteins, peptides, etc; a sample including a cell organelle(s); a sample including natural or recombinant biological molecules, e.g. blood plasma sample, conditioned cell culture media; and a sample including plant cells or debris thereof.

The above mentioned embodiments of biological samples are exemplary and for the purpose of illustration only.

Examples of chemical samples may be illustrated by and are not limited to samples of libraries of chemical compounds, e.g. peptide libraries. Examples of the environmental samples may be illustrated by and are not limited to soil, water or air samples and food samples.

Embodiments consistent with the present disclosure may relate to samples including an immobilized target, i.e., to samples, where the target is prevented from freedom of movement during detection procedures consistent with embodiments of the present disclosure. For example, samples, where the target motion is substantially reduced or eliminate by mechanical or chemical means, as in the case of samples or targets attached to or within a certain support or medium. Thus, a sample including single individual units of a target of interest may in one embodiment be immobilized onto a slide before the detection procedure, e.g. a solid body tissue sample immobilized on a glass slide. Examples of samples including immobilized targets of the invention include but are not limited to body tissue samples immobilized on glass or plastic slides, or to samples comprising biological or chemical molecules immobilized onto membranes or ELISA plates. A target of a sample in these embodiments may be immobilized either within the sample, e.g. a protein fixed within a tissue sample, or may be immobilized on the surface or within certain material, such as, e.g., a portion of a solid material or a gel such as a nitrocellulose membrane, etc. In one embodiment the slide may be a three-dimensional structure, e.g. a collagen or agar block, and a target may be immobilized within the structure.

Additional examples of targets may include, for example, a particular protein including all molecules of that particular protein in a sample; another example of a target of the invention may be a particular molecular complex or structure including substantially all objects of the sample that comprise that particular molecular complex or molecular structure; another example of a target of the invention may be a viral particle or a bacterium, wherein total population of that viral particles or that bacteria of the sample is the target.

Biological objects such as molecules, molecular complexes, structures, particles or organisms which are associated with features that are characteristic for a particular cell type, tissue, cellular structure, physiological condition, etc., are often termed "biological markers" of that particular cell type, tissue, cellular structure, or physiological condition. Non-limited examples of such biological markers include but are not-limited to particular nucleotide sequences, proteins or other biological molecules, e.g. carbohydrates or lipids, chromosomal or membrane structures, viruses, bacteria, microorganisms etc. In some embodiments of the invention, the term "target" is used interchangeably with the term "biological marker" and relates to a molecule, molecular complex, structure or particle that is characteristic for a particular cell type, tissue, physiologic condition, etc, wherein the total population of any of the latter biological markers in the test sample is considered to be the target.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, e.g. fragments, precursors, mutants of target proteins or nucleic acids, etc. may also be targets in some embodiments of the invention.

Thus, in different embodiments of the invention the target may be a biological or chemical target molecule, or a particle, or a molecular or cellular complex, or molecular or cellular structure, or a virus, or a microorganism, or a fragment of said target molecule, particle, complex, structure, virus or microorganism. Among targets contained in chemical and environmental samples may be different pollutants, toxins, warfare substances, members of molecular libraries, industrial noxious waste compounds, etc.

The invention may relate to targets that may be represented in a sample by a plurality of independent substantially identical units, the invention may relate to single individual units of a target.

The term "unit" may refer to a single quantity of a target regarded as a whole in calculation and serving to perform one particular function. The term "individual" may mean that a unit is separable from the other units of the same kind or other components of the environment (by physical features of a function) and can be considered and counted separately. The term "individual unit" may be interchangeably used with the term "single unit". The term "single" in the present context may mean a target unit is consisting of a separate whole, is consisting of only one in number, is consisting of one as opposed to or in contrast with many. For example a single/individual unit of a target protein means a single individual protein molecule of the target protein, i.e. one molecule of plurality molecules of the same kind. The term "substantially identical units" means that a plurality of single units of a target possesses one or more features that make these units be considered as the target. The term "independent" means that a single unit of a target exists as a distinct entity and do not depend on the existence of other distinct entities of the same kind in the sample.

The invention is some embodiments relate to a single unit being a single part of a molecule. The term "single part of molecule" relates to a part of a molecule that has particular properties that allow considering this part of the molecule separately from the other parts of the same molecule, e.g. a proteolytic fragment of a target protein, a part of a fusion protein, a particular domain of a target protein, a particular structure of a nucleic acid, an epitope, etc.

Thus, in one embodiment, the invention may relate to single/individual units of a target being single individual target molecules, i.e. to a plurality of single individual target molecules present in a sample, in another embodiment the invention may relate to single/individual units of a target being single individual parts of a molecule, e.g. a particular molecular structures that presents in a plurality target molecule in a sample, e.g. an epitope. In another embodiment the invention may relate to a plurality of single individual viral particles making a pool of viral particles present in a sample.

In different embodiments a plurality of single units of a target may be represented by single individual biological or chemical molecules, single individual single particles, single individual molecular or cellular complexes, single individual molecular or cellular structures, or single individual viruses or single individual microorganisms, or single individual fragments of said molecules, particles, complexes, structures viruses or microorganisms.

In one embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. The methods of the invention allow a simple and rapid visualization and quantification of said biological markers.

The methods of the invention allow visualizing and quantifying single individual units of a target present in a sample in a broad dynamic range. Both very high amounts and very low amounts of a target may be visualized and quantified in one and the same sample, or they may be evaluated in separate samples. Two or more different targets may be visualized in one or the same sample, e.g. a protein target and nucleic acid target, or two or more different protein targets, or two or more different nucleic acid targets, etc.

In one embodiment, single units of a target may be distributed substantially homogeneously throughout a sample, in other embodiments, single units of a target may present as more abundant in one part of a sample and less abundant in other parts thereof. In all the latter embodiments, single units of the target may be visualized and quantified in one and the same sample using methods of the present invention. In some embodiments, wherein a single target unit is associated with another target of interest, e.g. present in a particular molecular association or a structure in which said particular association or structure is a biomarker of a pathological condition, said another target of interest may be visualized and quantified by visualizing and quantifying single target units in the sample as well.

In one embodiment, the invention relates to a fractional sub-population of single target units present in a sample, such as a majority or a minority of the total number of single individual target units present in the sample. The term "fractional subpopulation" in the present context means a portion of the total population of single target units that is equal or less than 99.9%. e.g. equal or less than 98%, 97%, 95%, 94%, 93%, 92%, 91% or 90% of the total quantity of single units of the target in the sample, such as between 90% and 85%, less than 85%, e.g. 85%-80%, 80%-75% of the total quantity of units of the target in the sample, such as less than 75%, for example from 1% to 74% of the total quantity of single units of the target in the sample, such as .from 1% to 60%, 1% to 50%, 1% to 40%, 1% to 30% or 25% of the total quantity of units of the target in the sample, etc. A fractional sub-population single target units that is represented by 50%-99.9% of the total population is defined according to the invention as a majority of single target units present in the sample. A fractional sub-population that is represented by less than 50% of the total population of single target units in a sample is defined according to the invention as a minority of single target units present in the sample.

In one embodiment, a majority of individual single target units may be involved in formation of discrete single target sites of the invention; in another embodiment, a minority of individual single target units may be involved in formation of discrete single target sites of the invention. In one embodiment, substantially all individual single units of a target may be involved in formation of complexes with one or more binding agents, wherein only a fractional sub-population of said complexes is involved in formation of discrete single binding sites of the invention.

Methods of the invention may include a step wherein a sample presumably comprising a target is incubated with one or more binding agents.

The term "binding agent" designates a molecule that is capable of directly or indirectly specifically binding to a single unit of a target, e.g. an individual molecule of a target protein. The term "specifically" means that the binding agent has a particular affinity to the target, e.g. affinity to a target molecule, or particular affinity to an agent that is bound to the target, e.g. affinity to a primary antibody bound to a target protein, affinity to a hapten conjugated with a primary antibody, etc. The term "directly" means that a binding agent having a specific affinity to a single individual unit of target interacts and forms an immediate bond with this single individual unit upon interaction, e.g. a primary antibody binds directly to a single individual target molecule that was used as an antigen for raising said primary antibody. The term "indirectly" in the present context relates to a binding agent, wherein said binding agent has no specific affinity to a single individual unit of the target, but wherein said binding agent has a specific affinity to another substance that is capable of specifically binding to that single individual unit, e.g. a primary antibody, or wherein said binding agent has a specific affinity to a substance that is associated or linked to said single individual unit, e.g. to a hapten; said binding agent directly interacts with the latter substances and forms a bond with said substance, and thereby the binding agent becomes indirectly bound to the single unit of the target.

A binding agent which is capable of directly specifically binding to a single unit of target is typically represented herein by a first binding agent. A binding agent which is capable of indirectly specifically binding to a single unit of target is typically represented by a second binding agent. However, a detection system according to the invention may comprise further binding agents that can be indirectly bound to the single unit of the target, e.g. third, fourth, and further binding agents.

Typically, a first binding agent or, in some embodiments, a second or third binding agent, is used to contact the sample to recognize the target, bind to it and form a complex with it. Second, third and further binding agents may be used in further steps of methods according to the invention, e.g. for recognition of deposits of detectable molecules at target sites described below. In some embodiments, second, third and further binding agents are used to amplify a signal associated with a target. These binding agents are also useful to add flexibility to the detection system, e.g. to change the original signal associated with the target, e.g. a red fluorescent signal to green, etc, Binding agents of the invention may be members of different specific binding pairs. A number of different specific binding pairs are known in the art, these are the pairs of two different molecules which are capable of specific binding to each other. Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino) benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the first binding agent and the secondary antibody represents the second binding agent; Antibody systems comprising 3 or 4, or more antibody members may be used in another embodiment. In other embodiments of the invention the immune binding pair may be represented by a hapten-anti-hapten system. In such embodiments the first binding agent may be represented by a conjugate comprising a molecule having affinity to the target and a hapten, e.g. a primary antibody or nucleic acid sequence linked to a hapten, and the second binding agent may be represented by an anti-hapten antibody.

The term "hapten" designates a small molecule which can be considered as, an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. A part of an antibody can include any fragment which can still bind antigen, for example, an Fab, F(ab')$_2$, Fv, scFv. The origin of the antibody is defined by the genomic sequence irrespective of the method of production.

Primary antibody, in the context of the present disclosure, refers to an antibody binding agent, e.g. a whole antibody molecule, a fragment or a derivative of said molecule, e.g. a conjugate comprising an antibody or a polymerized antibody, that specifically binds to a target, more specifically to a single unit of a target of a sample, e.g. to a single target molecule. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention may be a single Her2/Her3 dimer, and the target may be a population of Her2/her3 dimers in a sample including all said dimers of the sample. Primary antibodies may be derived from any warm blooded species, e.g. mammals, birds.

Secondary antibody, in context of the present disclosure, refers to an antibody binding agent, e.g. a whole antibody molecule, a fragment or a derivative of said molecule, e.g. a conjugate comprising an antibody or a polymerized antibody, that has an antigen binding domain that specifically binds to the primary antibody, or a hapten deposited in the target site, or hapten linked directly or indirectly to a primary antibody or another binding agent.

Tertiary antibody, in context of the present invention, refers to an antibody binging agent, e.g. a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody. Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments a primary antibody contains an antigen binding region which can specifically bind to a biological marker, in particular to a single individual unit of said biological marker, expressed by cells of a biological sample. The marker may be expressed on the cell surface or within the cell membrane, i.e., on the interior of the cell, e.g., within the cytoplasm, within the endoplasmic reticulum, etc. In some embodiments the biological marker may be extracted from the cell and thus it is present in a cell-free medium, e.g. in an aqueous solution, or it is a soluble molecule present in a cell culture media, blood plasma, cerebrospinal fluid, etc. Examples of the corresponding samples are described above.

In certain embodiments, a secondary antibody contains an antigen binding region which specifically binds to a primary antibody, e.g., to the constant region of the primary antibody. In certain embodiments, a secondary antibody may be conjugated to a polymer. In some embodiments, 2-20 secondary antibodies, such as 5-15 secondary antibodies may be conjugated with a polymer. In other embodiments, a polymer may be conjugated with 1-10 secondary antibodies, such as 1, 2, 3, 4, 5, 6, 7, 8, 9 or 10 secondary antibodies.

In certain embodiments, a tertiary antibody may contain an antigen binding region which specifically binds to a secondary antibody, e.g., to a constant region of a secondary antibody, or to a hapten linked to a secondary antibody, or to a polymer conjugated with a secondary antibody. In certain embodiments, a tertiary antibody is conjugated to a polymer. In some embodiments, 1-20 tertiary antibodies may be conjugated a polymer. In other embodiments, 1-5 tertiary antibodies, such as 1, 2, 3, 4 or 5 tertiary antibodies may be conjugated with a polymer.

Some embodiments may include polymers comprising a single binding unit of a binding agent, e.g. a polymer conjugated with one molecule of primary, secondary or tertiary antibody.

Antibodies that may be used for the purposes of the invention include monoclonal and polyclonal antibodies, engineered antibodies including chimeric, CDR-grafted and artificially selected antibodies produced using phage display or alternative techniques.

Antibody binding agents of the invention may be produced by any of numerous methods well-known in the art. Nucleic acids encoding antibodies may be isolated from a cDNA library. Nucleic acids encoding antibodies may be isolated from a phage library. Nucleic acids encoding antibodies can be obtained by gene shuffling of known sequences. Nucleic acids encoding antibodies can be isolated by in vivo recombination. The antibodies used in the methods of the invention include humanized immunoglobulins. Antibodies of the invention may be altered in any possible way, presuming that they retain their binding affinity, e.g. they may fused with an effector protein, toxin, label, etc. Methods of conjugation of antibody with different agents are described in exemplary embodiments of the invention below.

In one embodiment of the invention, an antibody binding agent is represented by the Fab region.

In one embodiment an antibody binding agent may be a composition comprising two or more different antibody binding agents, e.g., a composition comprising a first antibody binding agent and a second antibody binding agent, wherein the two or more different antibody agents are of different immune binding pairs. In one embodiment, in the composition, at least one of two or more different antibody binding agents is an antibody that is capable of specifically binding to a target and at least one other is an antibody which comprises a an enzyme.

In another embodiment, the invention may relate to binding agents that are members of non-immune specific binding pairs, such as complementary nucleotide sequences, or nucleic acid analog molecules.

A binding agent comprising a nucleic acid or nucleic acid analog molecule, e.g., a DNA molecule, an RNA molecule, a PNA molecule, may be useful for the visualization and quantification of single individual units of nucleic acid targets.

Nucleic acid sequences used as binding agents for the purposes of the invention may be synthesized chemically or produced in recombinant cells. In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. In other embodiments, the binding agent may comprise a locked nucleic acid (LNA).

A nucleic acid binding agent, in some embodiments, may comprise at least one oligo- or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other.

In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, may include conditions that can be readily determined by those having ordinary skill in the art based on, for example, the length of the DNA. Exemplified conditions include use of a prewashing solution of 5×SSC, 0.5% SDS, 1.0 mM EDTA (pH 8.0) hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents that are peptide sequences or comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding agent may also be small molecules which can bind specifically to certain structural units of large biological molecules.

In some embodiments binding agents may comprise a detectable label, e.g. a fluorescent substance, hapten, enzyme, etc. In one embodiment, the invention relates to labeled binding agents, i.e. labeled first, second, third or further binding agents, that are capable of specifically binding to their binding partners in the sample, e.g. units of the target, other binding agents, deposited detectable molecules. Such binding agents may be used for visualization of target units in the sample or target sites of the invention. In one embodiment, the invention relates to a binding agent comprising a label which is an enzyme. Non-limiting examples of suitable enzyme labels may be horseradish peroxidase (HRP), alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO). In one embodiment, a binding agent may comprise HRP as a label. In another embodiment, a binding agent may comprise AP as a label. Other enzyme embodiments are discussed below.

Amounts of binding agents necessary for forming target sites of the invention may vary depending on different factors, e.g. sample species, target species, binding agent species, binding affinity of binding agents, etc. An appropriate binding agent and the amount needed may be selectively determined for every particular embodiment. In some embodiments the amounts of binding agents used for forming the target sites may be adjusted so that not all single units of a target present in the sample, but a fractional sub-population thereof is involved in formation of the target sites, e.g. these embodiments may relate to a sample comprising a target in abundant amounts, or a target present in a broad dynamic concentration range. In other embodiments, it may be that all or substantially all single units of a target are involved in formation of target sites of the invention, e.g. in case of samples with a very low target expression of a target or single units of a target. In the latter embodiments, binding agents in amounts that will secure formation of binding sites with a substantial majority of individual single units of the sample may be used, i.e. a substantial majority of single units of a target present will be involved in formation the target sites.

In one embodiment, a binding agent may be a mixture of unlabelled and labeled binding molecules of the same species that have affinity to the same binding partner, e.g. a mixture of labeled and unlabelled primary antibody to a particular target protein, or a mixture of labeled and unlabelled secondary antibody against a particular species of primary antibodies, or the like. Using the latter mixtures of binding molecules, wherein a portion of the labeled binding molecules is predetermined, the target sites formed (and then visualized as visually distinct dots) with a certain fractional sub-population of single target units that is predetermined by the portion of the labeled binding agent. This allows the determination of the precise quantity of single target units in the sample, and, thus, the quantity of the target, including a relative and total amount of the target in the sample.

In some embodiments, the invention relates to a binding agent, e.g. a member of a specific binding pair, for which a binding affinity to its specific binding partner is a known binding affinity to its binding partner in the sample.

The affinity between members of specific binding pairs is commonly described by the dissociation constant, e.g. ligand and receptor, antibody and antigen, and the like, i.e. how tightly one binding partner (BP1) binds to another binding partner (BP2) of the pair.

The formation of a complex between the binding partners (BP1:BP2) can be described by a two-state process:

BP1: BP2<=>BP1+BP2; the corresponding dissociation constant is defined $$Kd = \frac{[BP1][BP2]}{[BP1:BP2]}$$

where [BP1], [BP2] and [BP1:BP2] represent molar concentrations of the BP1, BP1 and complex of BP1 and BP2, respectively.

The dissociation constant has molar units (M), which correspond to the concentration of BP1 at which the binding site on BP2 is half occupied, i.e. the concentration of BP1, at which the concentration of BP2 with BP2 bound [BP1:BP2], equals the concentration of BP2 with no ligand bound [BP2]. The smaller the dissociation constant, the more tightly bound the BP1 is, or the higher the affinity between BP1 and BP2. For example, a BP1 with a nanomolar (nM) dissociation constant binds more tightly to a BP2 than a BP1 with a micromolar (µM) dissociation constant.

The dissociation constant for a particular BP1 to BP2 interaction can change significantly with solution conditions (e.g. temperature, pH and salt concentration). The effect of different solution conditions is to effectively modify the strength of any intermolecular interactions holding a particular BP1:BP2 complex together. Conditions of media relevant to formation of BP1:BP2 complex for the purposes of the present invention are discussed in further sections below.

In the specific case of antibodies (Ab) binding to antigen (Ag), usually the affinity constant (Ka) is used. It is the inverted dissociation constant. That is:

$$Ab + Ag \Longleftrightarrow Ab:Ag;$$

$$Ka = \frac{[Ab:Ag]}{[Ab][Ag]} = \frac{1}{Kd}$$

This chemical equilibrium is also the ratio of the on-rate (kforward) and off-rate (kback) constants. Two antibodies can have the same affinity, but one may have both a high on- and off-rate constant, while the other may have both a low on- and off-rate constant.

$$Ka = \frac{K_{forward}}{K_{back}} = \frac{\text{on-rate}}{\text{off-rate}}$$

A binding agent with known Kd or Ka may be obtained from a commercial provider, or Kd and/or Ka may be predetermined be any technique known to the skilled in the art. A method of determining Kd of a first and second binding agent in a histological sample using a visualization system of the invention, and use this determination for quantifying a target in a histological sample is described below.

At least one binding agent may include an enzyme that binds, directly or indirectly, a single unit of the target and forms a complex with said unit.

An enzyme may be an enzyme with oxidoreductase activity (interchangeably termed herein as "oxidoreductase" or "enzyme of the invention"). By the term "enzyme with oxidoreductase activity" is meant an enzyme classified as EC 1 in the EC number classification of enzymes that catalyzes the transfer of electrons from one molecule (the reductant, also called the hydrogen or electron donor) to another (the oxidant, also called the hydrogen or electron acceptor). In some embodiments, the invention relates to oxidoreductases classified as E 1.10. (phenoloxidases) and E 1.11. (peroxidases).

One embodiment the invention may relate to phenoloxidases, in particular to the family of copper-containing oxidase enzymes, laccases (E 1.10.3.2). Laccases act on phenols and similar molecules; performing one-electron oxidation. Laccases play a role in the formation of lignin by promoting the oxidative coupling of lignols, a family of naturally occurring phenols.

The term "laccase" is used herein to designate an enzyme with phenoloxidase activity of the invention, however it is understood then laccase is one of many embodiments of phenoloxidase that are suitable for the purposes of the invention.

In another embodiment, the invention may relate to a peroxidase enzymatic activity catalyzing a reaction of the form:

ROOR'+electron donor(2e⁻)+2H⁺→ROH+R'OH

In one embodiment of the invention, the enzyme with peroxidase activity is horseradish peroxidase (HRP). In another embodiment of the invention, the enzyme with peroxidase activity is soyabean peroxidase (SP).

For some peroxidases the optimal substrate is hydrogen peroxide, some others are more active with organic hydroperoxides such as organic peroxides. The nature of the electron donor is dependent on the structure of the enzyme, e.g. horseradish peroxidase (HRP) can use a variety of organic compounds both as electron donors and acceptors. HRP has an accessible active site, and many compounds can reach the site of the reaction.

The enzymatic activity, i.e. oxidireductase activity, e.g. phenoloxidase or peroxidase activity, may be represented by a full-length molecule of an enzyme which is directly or indirectly linked to the molecule of a binding agent, or a fragment of the enzyme conflated with the enzymatic activity, e.g. 51% to 99.9% of the full size of the enzyme molecule, or less than 51%, e.g. 40%, 30% or less.

A binding agent of the invention may be directly or indirectly conjugated with one or more enzyme moieties, (the term "moiety" in the present content means a part of molecule of the enzyme that is capable of oxidoreductase activity, it includes both entire or substantially entire enzyme molecule and portions of said molecule that are capable of oxidoreductase enzymatic activity). Molecules of both or either first and/or second binding agents may be conjugated with one or several functionally active moieties of an oxidoreductase. In one embodiment at least one molecule of a first binding agent may be conjugated with one or more enzymatic moieties capable of oxidoreductase activity; in another embodiment at least one molecule of a second binding agent may be conjugated with one or more such moieties. Molecules of third and further binding agents may also be conjugated with an oxidoreductase. The term "directly conjugated" means that an enzyme moiety is linked to a molecule of a binding agent via a chemical bond. The term "indirectly conjugated" means that a moiety of an enzyme is linked to the molecule of a binding agent via a linking molecule, which has one chemical bond with binding agent and another chemical bond with the enzyme.

In one embodiment the moiety of oxidoreductase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the moiety of oxidoreductase may be a moiety of soybean peroxidase (SP). In another embodiment the moiety of oxidoreductase may be a moiety of laccase.

Non-limiting examples of binding agents which comprise an enzyme with oxidoreductase activity may be antibody molecules or derivatives thereof, e.g. a Fab, conjugated with one or more moieties of HRP, and nucleic acid binding agents conjugated with HRP. Such binding agents may bind directly or indirectly to single target units, e.g. single target molecules, and form thereby complexes, wherein a single such complex comprises a single individual unit of the target and one or more of binding agents wherein one or more of the binding agents comprise an enzyme with oxidoreductase activity.

In one embodiment, the binding agent is a conjugate comprising one, or two or more moieties of a peroxidase wherein said moieties are directly linked to the binding agent, e.g. an antibody molecule directly conjugated with one or more moieties of HRP. In another embodiment the binding agent may be a conjugate that comprises two or more enzymes with peroxidase activity, e.g. two or more moieties of HRP, that are linked to the binding agent indirectly, e.g. a conjugate wherein one or more molecules of an antibody and one or more HRP moieties independently linked to a backbone polymer, i.e. the enzyme with peroxidase activity is indirectly linked to the binding agent, i.e. to the antibody.

The number of HRP per molecule of binding agent may vary, from being 1 enzyme moiety per binding agent, to 20-50 per a binding agent, or even higher. Some embodiments may use binding agents wherein the number of HRP moieties is at least two, including from two to twenty-twenty five enzyme moieties per binding agent, e.g. between three and twenty, such as 4, 5, 6, 7, 8, 9, 10 etc. Some embodiments may use binding agents comprising more than two enzyme moieties per binding agent, including between 5 and 20, for example from 5 to 15. Binding agents with more than four enzyme moieties may be favorable for formation of target sites which can be visualized as substantially identical in size dots. In some embodiments, it may be even that each binding agent molecule comprising the enzyme of a pool of such binding molecules comprises approximately the same number of enzyme moieties, e.g. 4-6 per binding agents of a pool, 5-7, 6-8,7-9, 8-10, etc moieties of enzyme per binding agent molecule, e.g. 5-6 or 6-7 HRP moieties per an antibody molecule, e.g. per primary or per secondary antibody molecule. The latter mentioned binding agent constructs comprising multiple moieties of HRP are exemplary. To achieve the mentioned effect, a binding agent may comprise multiple moieties of any enzymes with oxidoreductase activity of the invention discussed above. The binding agent may also comprise a combination of multiple moieties of different oxidoreductase enzymes.

In some other embodiments, relatively small conjugate molecules of binding agents, e.g. single antibody molecules or isolated Fab regions of antibodies that are conjugated with one, or two, or more moieties of an enzyme, e.g. HRP, may be used. Such binding agents are relatively compact molecules and this may be advantageous for detecting individual units of targets that are "hidden" or masked in a target or in a sample, e.g. individual single target molecules may be masked by other molecules of the surroundings, single target structures can be hidden in a target molecule, or single viral particles may be hard to reach in complicated biological samples comprising cells.

In some other embodiments, large conjugates comprising a binding agent and tens to hundreds enzyme moieties may be used. Such binding agents may be advantageous e.g. in cases where very fast target detection is concerned or obtaining large deposits per individual target site is desirable.

A single unit of a target bound (directly or indirectly) to a binding agent comprising an enzyme with oxidoreductase activity, e.g. peroxidase activity, may constitute a single target site of the invention.

In one embodiment, a single target site of the invention comprises a single target unit of a target, at least one primary antibody, or a derivative thereof, and at least one secondary antibody, or a derivative thereof, conjugated with one, two or more enzymes with peroxidase activity, e.g. HRP.

In another embodiment, a single target site may comprise a single unit of a target, at least one primary antibody molecule conjugated with a hapten and an antibody against hapten which are conjugated with one, two or more enzymes with peroxidase activity, e.g. HRP.

In another embodiment, a target site may comprise a single unit of a target, one or more first nucleic acid/nucleic acid analog binding agents specific for the target, and one or more second nucleic acid/nucleic acid analog binding agents specific for the first nucleic acid/nucleic acid analog binding agents.

The above embodiments are not limiting. Other embodiments may relate to any combination of a single unit of any target discussed above with any binding agents discussed above making a target site of the invention.

A single target site in one embodiment may be a single site of a slide comprising a single unit of a target labeled with enzymatic activity of the invention, i.e. conjugated directly or indirectly with an enzyme with oxidoreductase activity, or a single unit of recombinant fusion molecule comprising a an enzyme with oxidoreductase activity. In one embodiment an oxidoreductase enzyme may be the target; correspondingly, a target site in this embodiment may comprise just a single unit of an oxidoreductase enzyme, such as an immobilized moiety of an oxidoreductase enzyme, e.g. HRP or laccase which is immobilized on or within a slide.

After incubation with one or more binding agents and formation of target sites of the invention as described above, a sample comprising one or more single target sites according to the invention may incubated in an aqueous solution (i). An aqueous solution (i) according to the invention comprises a first substrate of an enzyme associated with a single target site of the invention, wherein said first substrate is a water soluble electron rich organic compound which is (1) capable of generating a stable radical upon a reaction with the enzyme; and (2) capable of cross-linking molecules of a second substrate of said enzyme in the presence of both the enzyme and a peroxide compound, thereby producing a water insoluble polymeric product of said second substrate. An aqueous solution (i) according to the invention may also include a second substrate of an enzyme associated with a single target site of the invention, wherein said second substrate is a conjugate molecule including at least two compounds that are capable of serving as substrates of said enzyme and a detectable label, wherein the detectable label is selected from the group consisting of a fluorescent, luminescent, radioactive or chromogenic matter or a member of a specific binding pair.

A first substrate of an enzyme associated with a single target site of the invention (also termed hereafter as "first substrate") may be a substrate of an enzyme with oxidoreductase activity. This substrate (1) may be a water soluble electron rich organic compound, (2) may be capable of generating a radical upon a reaction with said enzyme, and (3) may be capable of cross-linking water soluble molecules of a second substrate of said enzyme (in the presence of said enzyme and a peroxide compound) producing thereby a water insoluble polymeric product of said second substrate.

By the term "water soluble" is meant that molecules of the first substrate are soluble in water and water containing solutions. By the term "electron rich compound" is meant an organic compound that comprises a conjugated system of connected p-orbitals including compounds with alternating single and multiple bonds. Lone pairs and radicals may be part of the system. The compound may be cyclic, acyclic or both. By "conjugated" is meant that there is an overlap of one p-orbital with another across an intervening sigma bond (in larger atoms d-orbitals can be involved). A conjugated system has a region of overlapping p-orbitals, bridging the interjacent single bonds. They allow a delocalization of pi electrons across all the adjacent aligned p-orbitals, which in general may lower the overall energy of the molecule and increase stability. The pi electrons of a conjugated system do not belong to a single bond or atom, but rather to a group of atoms.

The group of enzymes with oxidoreductase activity of the invention includes diverse enzymes that can utilize a great number of substrates. Among these substrates, the substrates of the invention are those compounds that are water soluble organic electron-rich organic compounds comprising a conjugated pi-system, which are capable of generating radicals, including stable radicals, upon a reaction with an enzyme with oxidoreductase activity of the invention. The term "stable radical" in the present context means that under conditions of the present invention, e.g. in an aqueous solution (A) (described below), a radical of the first substrate has a life time of at least 20 seconds, including from about 1 minute to about 15 minutes, or longer e.g. 2, 3, 4, or 5 minutes, between 5 and 10 minutes, etc. Further, radicals of compounds that make up the group of the first substrates of the invention are capable of cross-linking water soluble molecules of the second substrate of the invention and thereby converting said water soluble molecules into a water insoluble polymeric product.

In particular, in one embodiment the invention relates to the first substrate which is represented a group of a water soluble organic electron-rich compounds that comprise a group of interconnected carbon atoms, wherein every second bond is a double bond, including compounds that comprise a chain of at least three (C—C=) repeats, or compounds comprising an aromatic ring structure.

In one embodiment, the first substrate may be represented by a compound comprising a structure of formula (I):

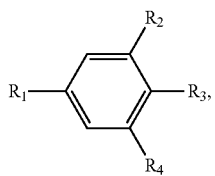

wherein R1 is an aryl or vinyl, R2, R3 and R4 is independently H, N—(X)$_2$, O—(X)$_2$, wherein X is an alkyl, vinyl or aryl, or H, and wherein R2, R3 and R4 are not simultaneously H, wherein N is nitrogen, H is hydrogen; O is oxygen.

Non-limiting examples of compounds of above formula that have capacity as the first substrate of an enzyme with oxidoreductase activity of the invention may be 3'3'-diaminobenzidine, ferulic acid, hydroxycinnamic acid and derivatives thereof.

In one embodiment the invention relates to 3'3'-diaminobenzidine (DAB) as the first substrate.

The present invention utilizes the capacity of DAB to form a stable radical which can cross-link molecules of the second substrate in the presence of an enzyme with oxidoreductase activity, i.e. horse radish peroxidase (HRP), and a peroxide compound, i.e. hydrogen peroxide, and deposit the cross-linked molecules of the second substrate discretely at single target sites.

Another embodiment may relate to ferulic acid as the first substrate.

Ferulic acid is capable of cross-linking molecules of second substrates of the invention in the presence of an enzyme with oxidoreductase activity, i.e. horse radish peroxidase (HRP), and a peroxide compound, i.e. hydrogen peroxide, and deposit said second substrate discretely at single target sites of the invention. Ferulic acid as the first substrate is particular useful in embodiments where larger deposits of the second substrate at target sites are desirable, e.g. dots of more than 2 micrometer in diameter.

In some other embodiments the invention may relate to derivatives of 3'3'-diaminobenzidine or ferulic acid. The term "derivative" means in the present content a compound that is derived from 3'3'-diaminobenzidine, ferulic acid or a compound that can be imagined to arise from 3'3'-diaminobenzidine, ferulic acid, if one atom in the latter molecules is replaced with another atom or group of atoms. The invention relates to derivatives of 3'3'-diaminobenzidine and ferulic acid that meet the requirements for the first substrate of the invention discussed above, e.g. alpha-cyano-4-hydroxy-cinnamic acid as derivative of ferulic acid.

In another embodiment, the invention relates to 4-hydroxy-cinnamic acid and derivatives thereof as the first substrate, e.g. alpha-cyano-4-hydroxycinnamic acid. Alpha-cyano-4-hydroxycinnamic acid as the first substrate is in particular useful in embodiments when small and compact deposits of the second substrate are desirable, e.g. dots around 2 micrometers and smaller.

For the purposes of the present invention, i.e. to produce deposits of the second substrate under conditions of the invention that are larger than 0.4 micrometer in diameter, such around 1 micrometer, 1.5 micrometers, 2 micrometer, 3 micrometer or 4 micrometer, the amount of a first substrate in the aqueous media (A) and/or aqueous media (B) may vary from around 0.05 mM to around 15 mM, depending on the structure of the compound representing the first substrate.

For example, the amount of a ferulic acid or a derivative thereof as the first substrate in the aqueous media (A) may vary between 0.5 mM and 5 mM, such as for example, around 0.5 mM, around 1 mM, around 1.5 mM, around 2 mM, around 2.5 mM, around 3 mM. The term "around" means a deviation of 1-25% from the indicated value.

Derivatives of hydroxycinnamic acid, such as Alpha-cyano-4-hydroxycinnamic acid, as the first substrate may be used in the range from about 1.5 mM to about 15 mM, e.g around 1.5 mM, around 1.75 mM, around 2 mM, around 2.5 mM, around 3 mM, between 3 mM and 4 mM, between 4 mM and 5 mM, between 5 mM and 6 mM, between 6 mM and 7 mM, between 7 and 8 mM, between 8 mM and 9 mM, between 9 and 10 mM, between 10 mM and 11 mM, between 11 mM and 12 mM, between 12 mM and 13 mM, between 13 mM and 14 mM, between 14 mM and 15 mM (including both end points of all mentioned intervals and all values within).

When DAB is used as the first substrate, its amount in an aqueous solution (A) may be less than 1 mM, including within the range of 0.05 mM to 1 mM, such as between 0.05 mM and 0.08 mM, e.g. around 0.07 mM, i.e. from 0.066 mM to 0.074 mM, or between 0.08 mM to 0.1. mM, e.g. around 0.09 mM, or between 0.1. mM and 0.3 mM, e.g. around 0.15 mM, around 0.2 mM, around 0.25 mM, or between 0.3 mM and 0.6 mM, e.g. around 0.35 mM, around 0.4 mM, around 0.45 mM, around 0.5 mM, around 0.55 mM, or between 0.6 mM and 1 mM, e.g. around 0.7 mM, around 0.75 mM, around 0.8 mM, between 0.8 mM and 1 mM.

According to the invention the second substrate of an enzyme of the invention (also termed herein as "second substrate") is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair.

In some embodiments the invention relates to a large group of conjugate molecules as second substrates that share the following features:

The conjugate molecules are water soluble molecules comprising two or more substances that can serve as substrates of the enzyme of the invention, including as substrates of HRP, and one or more labels wherein the substrates and labels are linked together via a water soluble linker compound (termed hereafter "linker");

The enzyme substrate moieties are "concentrated" in the conjugate molecule in one part of said molecule and the labels are "concentrated" in another part of said molecule, wherein the label(s) are distanced away from the substrates by approximately 30 consecutively interconnected atoms or more, i.e. separated approximately by 2.5 nm or more, including by more than 3 nm The enzyme substrates are separated from each other by a distance that is less than 2.5 nm, e.g. separated within molecule of the conjugate by less than 30 interconnected carbon or heretoatoms, such as carbon, nitrogen, sulphur and/or oxygen atoms or less, including not more than 5-20 atoms;

The linker is a compound which comprises at least 30 consecutively connected atoms;

The conjugates do not precipitate from an aqueous solution (ii) containing a peroxide compound and a first substrate of the invention in the absence in the environment of an enzyme with oxidoreductase activity.

The conjugates do not precipitate from an aqueous solution (ii) containing a peroxide compound in the presence of an enzyme with oxidoreductase activity and in the absence the first substrate of said enzyme in the environment.

The conjugates precipitate from an aqueous solution (ii) containing a peroxide compound and the first substrate of an enzyme with oxidoreductase activity of the invention in the presence of said enzyme in the environment.

Deposits of the second substrate may be directly recognizable by visual means because they, in some embodiments, may comprise a chomogenic, fluorescent or luminescent label. In other embodiments the precipitated second substrate may be "stained" in steps following the deposition to be visible. In both cases, the deposits of the second substrate will "report" to the observer the presence a single target site of the invention in the surroundings. The molecules of second substrate of the invention are thus interchangeably termed herein "reporter" molecules.

Non-limiting embodiments of second substrate molecules suitable for the purposes of the present disclosure may be described in more detail below.

In one embodiment the invention relates to a second substrate which is a water soluble conjugate molecule that comprises one or more detectable substances (termed interchangeably "label") at least two substances, which are capable of serving as substrates of the enzyme of the invention, and a linker wherein said linker is a compound comprising at least one linear chain consisting of at least 30 consecutively connected atoms that contains at least two branching points, wherein said brunching points are separated by a molecular distance of at least 30 consecutively connected atoms; wherein the labels (i) and oxidoreductase substrate moieties (ii) are attached to the linker at its two branching points that are separated by a distance of at least 30 consecutively connected atoms, and wherein any two neighboring enzyme substrates are separated from each other by a molecular distance that is less than 30 consecutively interconnected atoms The term "detectable substance" means that the substance can give off a detectable chromogenic, fluorescent, luminescent or radioactive signal be detected by visual means, or it can be detected using its specific binding partner, e.g. an antibody, nucleic acid sequence, nucleic sequence analog sequence, hapten, antigen, receptor, receptor ligand, enzyme, etc.

In some embodiments a water soluble conjugate molecule of the invention may additionally comprise moieties that may enhance its features, e.g. improve its capacity as the label or enzyme substrate, or increase/reduce its water solubility.

In one embodiment, conjugate molecules of the invention may be selected from a group of compounds of the following formula:

(Y)n-L-(Z)m, wherein Y is a moiety capable of serving as substrate of an enzyme with oxidoreductase activity; Z is a detectable label; L is a linker compound, wherein n is an integer from 2 to 150, and m is an integer from 1 to 150

In one embodiment Y may be selected from compounds of the following formula (II):

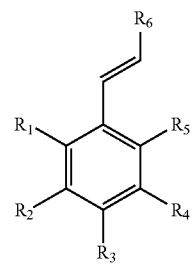

wherein R1 is —H, —O—X, N(X)$_2$ or —S—X; R2 is —H, —O—X, —N(X)$_2$, or —S—X, R3 is —H, —OH, —NH$_2$ or —SH; R4 is —H, —O—X, —N(X)$_2$, or —S—X, R5 is —H, —O—X, N(X)$_2$, or —S—X, R6 is —CON(X)$_2$, or CO—X, wherein H is hydrogen; O is oxygen; S is sulphur; N is nitrogen, and X is H, alkyl or aryl.

In one embodiment at least one of the compounds that are capable of serving as substrate of an enzyme with oxidoreductase activity is a compound of formula (II).

In one embodiment at least two of the compounds that are capable of serving as substrate of an enzyme with oxidoreductase activity in the conjugate molecule are compound of formula (II).

In one embodiment at least two of the compounds that are capable of serving as substrate of an enzyme with oxidoreductase activity in the conjugate molecule are identical compounds of formula (II).

In one embodiment at least two of the compounds that are capable of serving as substrate of an enzyme with oxidoreductase activity in the conjugate molecule are different compounds of formula (II).

In one embodiment all compounds that are capable of serving as substrate of an enzyme with oxidoreductase activity in the conjugate molecule are defined by formula (II). In one embodiment these are identical compounds, in another embodiment the conjugate molecule comprises any combination of different compounds defined by formula (II).

In one embodiment Y may be a residue of cinnamic acid; in another embodiment Y may be a residue of ferulic acid. In another embodiment Y may be a residue of caffeic acid; in another embodiment Y may be a residue of amino cinnamic acid. In another embodiment Y may be a residue of sinapinic acid. In another embodiment, Y may be a derivative of ferulic acid, cinnamic acid, caffeic acid, amino cinnamic acid or sinappinic acid.

A residue Y defined by the formula (II) may be connected to a linker L via group R6.

In one embodiment the conjugate comprises two to four identical residues Y. In another embodiment the conjugate comprises a combination of two to four different residues Y. In one embodiment the two to four residues Y are compounds defined by the formula (II).

In one embodiment, the conjugate may comprise two to four residues ferulic acid or residues of derivatives thereof, in another embodiment the conjugate may comprise two to four residues cinnamic acid or residues of derivatives thereof; in another embodiment the conjugate may comprise two to four residues of caffeic acid or residues of derivatives thereof; in another embodiment the conjugate may comprise two to four residues amino cinnamic acid; in another embodiment the conjugate may comprise two to four residues sinapinic acid or residues of derivatives thereof. The two to four derivatives of the latter compounds may be the same compound or may be different compounds.

In one embodiment a conjugate molecule may comprise two Y compounds of formula (II), or two derivatives thereof, e.g. two ferulic acid residues, or two cinnamic acid residues, or two amino cinnamic acid residues, or two caffeic acid residues, or two sinapinic acid residues, etc. and one or more detectable labels; in another embodiment the conjugate may comprise three molecules of formula (II) or three derivatives thereof, such as three ferulic acid, cinnamic acid, caffeic acid, amino cinnamic acid, sinapinic acid, etc., and one or more detectable label; in another embodiment the conjugate may comprise four compounds of formula (II) or four derivatives thereof, e.g. four ferulic acid, cinnamic acid, caffeic acid, amino cinnamic acid, sinapinic acid, or four derivatives the latter, and one or more detectable labels.

In some embodiments the number of Y compounds may be higher than 4, e.g. such as 5-10, 10-15, 15-20, 20-50, 50-100, or 100-150 compounds. Non-limiting examples of such conjugate molecules are described in Examples. In some embodiments such conjugates may comprise more than one linear chain of at least 30 consecutively connected atoms, e.g. 30-150 atoms, wherein two to four Y compounds are attached to each linear chain at first and the same branching point of the chain, and several of such linear chains are linked to another water soluble linker molecule, e.g. a dextran, via a second (another) branching point of said linear chains.

In one embodiment, a conjugate molecule may comprise a combination of two or four different compounds of formula (II), or a combination of two or four derivatives thereof, e.g. two ferulic acid residues and one cinnamic acid residue, two sinapinic acid residues and two caffeic acid residues, etc.

In one embodiment Y may be a residue of amino acid tyrosine or residue of a derivative thereof. A conjugate may comprise 2 to 4 or more such residues.

In one embodiment conjugate molecule may comprise a combination of substrates of the enzyme with oxidoreductase activity, wherein at least one of said substrates is tyrosine. In one embodiment the conjugate molecule comprises at least one tyrosine residue and at least one compound of formula (II), or a derivative thereof. and at least one another is a compound of formula (II) a derivative thereof, e.g. one tyrosine residues and two residues of sinapinic acid or derivatives thereof.

In some embodiments it may be that the conjugate comprises 4 to 6 residues Y, wherein Y is represented by any compound or a combination of any compounds as described above.

Y compounds may be located in a conjugate molecule as a group, and may grouped as two to four Y compounds per group, (i.e. a conjugate comprising more than four Y compounds may comprise several groups of two to four Y compounds, wherein said groups are separated in the conjugate molecule by a group of atoms, e.g. by a molecular distance corresponding to 30 connected atoms or more). The two to four Y compounds in such groups may be linked together via a spacer compound that provides a distance between two neighboring Y residues which is not longer than 5-15 interconnected atoms, e.g. 5-10, 6-12, 7-13, 8-14, 9-15, etc., For example, 2-4 Y compounds may be attached to amino acids making up a peptide chain comprising 2 to 4 amino acid residues, e.g. residues of lysine, serine, cystein, etc., wherein the Y compounds are attached to reactive groups of the amino acid residues of the peptide, e.g. to the epsilon amino groups of lysine residues. Two to four compounds Y may also be connected to each other via other short polymers which comprise a number of brunching points, wherein a molecular distance between these branching points corresponds to a chain of not more than 3-7 atoms, including 3-5 atoms, wherein the Y compounds may be directly indirectly linked to the branching points. Two to four compounds Y may also be grouped together being conjugated to a non-polimeric molecule that have two to four reactive groups allowing attaching any two to four Y compounds. Such grouped location of Y compound is termed thereafter "Y-head" of the conjugate molecule.

In one embodiment, the Y-head comprises two to four Y-residues linked via a short polymer, e.g. a short PNA molecule or a short peptide, wherein the peptide comprises lysine, serine glutamate and/or cystein residues. However, any other polymeric or non-polimeric water soluble molecules that comprise 15 or less atoms that can be conjugated with at least two Y-residues and a linker L may be suitable.

In one embodiment one Y-head comprising two to four compounds Y may be linked to a polymer comprising two or more repeats of the following formula (III):

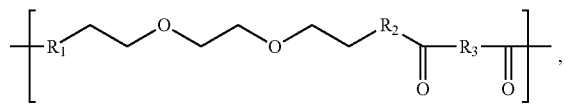

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups. The resulting conjugate may be further conjugated with one (or more) detectable label, or it may be conjugated with another water soluble molecule which comprises one or more reactive groups allowing attaching one or several such conjugates. One non-limiting example of such water soluble molecule may be a dextran polymer.

Close spacing of Y compounds in conjugate molecules has influence on functional capacity of the conjugates as second substrates of the invention, namely the conjugates remain soluble in aqueous solutions containing a peroxide compound and the first substrate of an enzyme with oxidoreductase activity (as described above), in the absence of the enzyme in the environment, but rapidly and efficiently precipitates from such solutions when an enzyme with oxidoreductase activity presents in the environment (compared to conjugates that comprise only one Y compound or comprise several Y compounds that are not "concentrated" in the conjugate molecule in form of an Y-head, i.e. molecular space between two neighboring Y residues is larger than the discussed above distance. Such compounds are not efficient to form discrete deposits at single target sites of the invention).

The detectable label of a conjugate molecule may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carbox-amido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetylglucosaminidase, β-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxiginin, fluorescein, Texas Red, tetra methyl rhodamine, nitrotyrosine, acetylaminoflurene, mercury trintrophonol, estradiol, bromodeoxy uridine, dimethylaminonaphthalene sulfonate (dansyl), amino acids tyrosine, serine, etc. As examples of suitable specific binding pairs may also be mentioned biotin, streptavidin, complementary natural and non-natural oligonucleotide sequences, zink fingers binding domain pairs, etc. Other examples are discussed above.

In one embodiment the label is a hapten. In another embodiment, the label is a fluorescent substance. In another embodiment, the label is a member of a specific binding pair. Other labels may be in other embodiments.

The number or detectable labels per conjugate molecule (as any of the described above) may vary. In some embodiments the number of labels may be from 1 to 3, for example 1, 2 or 3 labels per conjugate molecules. In some other embodiments, the conjugate may comprise more from 4 to 150 labels per conjugate molecule.

In one embodiment a conjugate (as any of the described above) comprises one detectable label. In one embodiment a conjugate molecule may comprise one Y-head (as any of the discussed above) and one label.

According to the invention, in a conjugate molecule the detectable substance (a single label or a plurality thereof) is separated from the compounds that are substrates of an enzyme with oxidoreductase activity, e.g. from an Y-head, by a molecular distance of more than 2.5 nm, e.g. separated by a chain of at least 30 consecutive atoms, e.g. 30-150 or more consecutive atoms. In embodiments where the conjugate comprises one chain of connected atoms as L linker between an Y-head and 1 (or more) labels, the Y-head and the label(s) are linked to said chain at branching points located at least 30 atoms apart from each other, e.g. on the opposite ends of a chain of 30 connected atoms.

In some embodiments, when a conjugate comprises more than 1 label, it may be that the labels are grouped so that there is a molecular distance between the labels, that correspond to a chain of at least 30 consecutively connected atoms (termed "spacer"), including 60 consecutively atoms or more, e.g. 90 consecutively interconnected atoms. It is that the spacer between the labels is a hydrophilic compound. The latter group of labels is then attached to a linker compound linking said labels and enzyme substrate moieties in a conjugate molecule in the way described above, i.e. a label of the group that is positioned closest to the Y-head is distanced away from any of the enzyme substrates of the Y-head by at least 30 interconnected atoms, i.e. by at least 2.5 nm distance. Such arrangement of multiple labels in a conjugate molecule is termed thereafter "Z-tail".

A spacer of at least 30 consecutive atoms between labels of a Z-tail may be a polymeric compound comprising two or more repeats of the following formula (III):

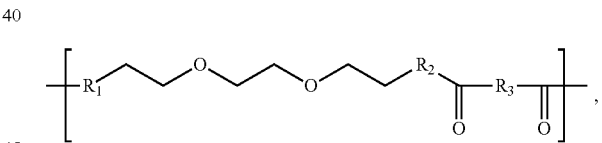

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Multiple labels attached to and separated by the above spacer may be conjugated with one Y-head or several Y-heads via any suitable linker, e.g. water soluble polymers allowing multiple attachments, e.g. dextran. In some embodiments several Y-heads may be conjugated with several Z-tails via such polymer.

In one embodiment multiple labels of a conjugate molecule of the invention may be same detectable substances, in another embodiment the labels may be different detectable substances.

The Z-tail arrangement of labels has advantages in that (1) conjugates comprising multiple hydrophobic labels remain good solubility in water solutions, and (2) the labels are better accessible for binding agents, when binding agents are used to detect the deposited conjugates.

The linker between the oxidoreductase substrates and labels (e.g. between Y head and Z tail), L, is according to the invention a molecule that comprises a chain of at least 30 contiguous atoms, such as 30-150 atoms or more, e.g. 30, 45, 60, 90, 150, 300, 500 atoms or more. In one embodiment, L comprises 150 contiguous atoms. In some embodiments, a linker molecule comprises a linear chain of atoms wherein every two connected carbon atoms are followed by an atom of oxygen or nitrogen.

In one embodiment L may be a single linear polymer molecule; in another embodiment L may be a conjugate molecule which may comprise several different polymers conjugated together.

In one embodiment L is a linear polymer that comprises a chain of atoms wherein two consecutive carbon atoms are followed by a heteroatom selected from oxygen or nitrogen, e.g. such as a linker as described below, or polyethylene glycol, etc.

In another embodiment the linker is a compound comprising two or more repeats of the following formula (III):

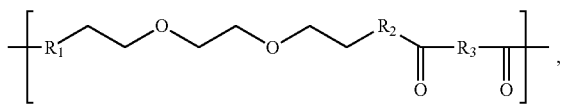

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

L may comprise at least two repeats of the following formula:

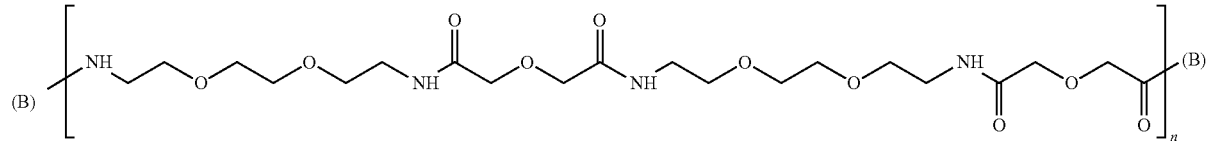

wherein both $R_1$ and $R_2$ are NH and $R_3$ is $CH_2OCH_2$. L may comprise one or more repeats of the following formula (IV) wherein n is an integer from 1 to 10, and (B) is a branching point.

By the term "branching point" is meant a point in a polymer molecule wherein a branch, e.g. a side chain of the same polymer, or other molecules may be attached. The branching point may be an atom, a group of atoms, or a functional group via which compounds Y and Z may be directly or indirectly conjugated to L.

There is a great variety of polymer molecules that may be used as linker L. Examples include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethyl-amino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly (acrylic esters), poly(2-hydroxy ethyl methacrylate), poly (methyl methacrylate), poly(maleic acid), poly(maleic anhydride), poly(acrylamide), polyethyl-co-vinyl acetate), poly (methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one embodiment the linker compound between oxidoreductase substrates and labels is a dextran polymer or a conjugate molecule comprising a dextran polymer.

Methods of conjugating polymers with different chemical substances, e.g. labels, are well known in the art and can be used to make conjugates of the invention. For example, the polymer may be activated with vinylsulfon and mixed with a detectable label and a molecule of formula (II) to form the polymer conjugate. In other embodiments, aldehydes can used to activate a polymer, e.g. dextran, which is then mixed with a detectable label and a molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and a detectable label can be attached to the polymer via a linking compound. Examples of this method include the use of homobifunctional linker compounds such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide.

Exemplary conjugates comprising linkers that are polymers comprising various number of repeats of formula (III), such as a polymer comprising two L30 repeats, (termed L60), such as a polymer comprising three L30 repeats (termed L90), such as a polymer comprising five L30 repeats (termed L150) are described further below.

The amount of the second substrate in the aqueous media (ii) may vary from about $10^{-10}$ M to about $10^{-4}$ M, for example, in case a conjugate (as any of the described above) comprises a radioactive label, the applicable amount may be from about $10^{-10}$ M to about $10^{-6}$ M, and from about $10^{-9}$ M to about $10^{-4}$ M, in case a conjugate comprises a fluorescent label or a label which is a member of a specific binding pair.

In one embodiment a sample comprising single units of a target is incubated during a visualization procedure according to the invention in different aqueous media (collectively termed herein "incubation media").

The term "incubation media" means in the present context an aqueous solution where the sample is maintained during a certain period of time (termed herein "incubation time") in order to achieve results of a desirable reaction.

Time for maintaining/incubating the sample in an incubation medium, i.e. incubating time, may vary depending on the technical effect which is desired to be achieved following the incubation. In different embodiments an incubation may lasts from approximately 3 seconds to approximately 3 min, e.g. around 10 seconds, 20 seconds, 30 seconds, 1 minute, 2 minutes, 5 minutes, 10 minutes, or longer, e.g. one-two hours, overnight. In some embodiments, all steps needed to produce the dots (e.g. on a dewaxed, target retrieved/fresh tissue) on a specimen may be completed within a 60 minute period. In other embodiments the dots are produced within a 100 minute period. In one embodiment, incubating time at all steps of the method may have the same duration, i.e. every incubating may lasts 5 to 10 minutes, etc. In another sample in an aqueous solution comprising a binding agent (termed hereafter "binding agent solution/media" or "BAM") may lasts 1-3 minutes, incubating in an aqueous media (i) and/or aqueous solution (ii) media may lasts 10 minutes.

Incubating may be performed at various temperatures, depending on the type of target, binding agent, etc. The procedures according to the invention are substantially temperature independent and can be performed at a temperature from around +4° C. to around +40° C. In some embodiments, it may be advantageous to perform all dot producing steps at a single temperature (e.g. room temperature or less than +30° C.). This may simplify automated processing protocols and equipment However, if desired, the temperature may be used for extending or reducing duration of an incubation, e.g. lower temperatures may be used to prolong the incubating time, and, vice versa, higher temperatures may be used to shorten the time for incubating.

On step (a) of the methods of the invention a sample is incubated with one or more binding agents (such as described above). Accordingly, in one embodiment, the invention relates to an aqueous solution comprising a binding agent, such as e.g. a binding agent comprising an enzyme with oxidoreductase activity. This medium is termed herein "binding agent medium".

One desired technical effect to be achieved due to incubation of the sample in such media is to form target sites according to the invention. Accordingly, the binding agent medium is an aqueous medium, in which the chosen binding agent is soluble and is capable of binding to a single target unit. Basically, the binding agent medium is a buffered aqueous solution of one or more binding agents that has pH in the range from 4 to 9. In some embodiments the binding agent medium may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in binding agent media may range from approximately $10^{-3}$ M to saturation, e.g. from approximately 20 mM to approximately 200 mM, or from approximately 50 mM to approximately 500 mM. In one embodiment, the media may comprise salt in the amount from approximately 10 mM to 500 mM. In another embodiment the medium may be free of salt.

As mentioned, typically, the pH value of binding agent media may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. The pH value of the media may be essential for binding of binding agent to the target; it may be optimized depending on the nature of the binding agent and the target.

In some embodiments binding agent media may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments binding agent media may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments binding agent media may comprise a binding agent stabilizing agent, e.g. bovine serum albumin or dextran. The amount of the stabilizing agent may vary from 0.01% to 20% (w/v).

In some embodiments binding agent media may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, binding agent media may comprise one or more blocking agents for saturating non-specific binding sites, i.e. sites of the slide that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats, accordingly, composition of the binding agent medium may vary and should be adjusted for every particular embodiment using the knowledge of the art. Further examples of binding agent media are described below.

Amounts of a binding agent in binding agent media may vary depending on the species of the biding agent, sample, target, composition of the media, etc. For example, in one embodiment, when a sample comprise a target that present in a low concentration range, relatively high amounts of binding agents may be used in a binding agent media in which composition (e.g. pH, salt concentration, etc) and incubation conditions (e.g. duration of incubation with the sample, temperature) are optimized to facilitate interaction between the binding agents and the target (or other binding partners). Optimization of binding between partners of specific binding pairs is a routine procedure for most of binding agents used for the purposes of the invention, so that a skilled in the art can do it by following guidelines of the art. Such optimization sometimes is necessary to secure binding of a binding agent to the maximal possible number of single units of the target or to another binding agent (e.g. a binding agent bound to the target) in the sample.

In one embodiment, the quantity of a binding agent in the binding media may be adjusted to bind all or a fractional sub-population of single target units present in the sample. In another embodiment, a quantity of binding agent is adjusted to bind all or a fractional sub-population of complexes of single target units with another binding agent of the sample. In one embodiment, the fractional sub-population corresponds to a majority of single target units of the sample. In another embodiment, the fractional sub-population corresponds to a minority single target units of the sample. In such embodiments, the composition of binding agent media, e.g. pH, salt content, etc., or incubating conditions, such as temperature, duration etc, may be adjusted so that the affinity of the binding agent to its partner in the sample will be diminished or enhanced and the binding agent will therefore form the binding complexes with a larger or smaller fractional subpopulation of single units of the target present in the sample. In one embodiment, the amount of a binding agent that is capable of specifically binding to its partner in the sample, e.g. a first binding agent, second binding agent and/or amount of binding molecules in a first or second binding agent mixture (see below), is relatively high to saturate all available binding sites in the sample even in conditions that do not favor the partner binding.

The term "fractional subpopulation" in the present context means a portion of the total population of the binding agent partner units in the sample that is equal or less than 99.9%, e.g. equal or less than 99%, 98%, 97% etc, e.g. 75-80%, less than 75%, less than 60%, etc, for example from 1% to 50%, such as .from 1% to 25%, etc. In some embodiments the fractional subpopulation may be less than 1% of the total quantity of units of the binding agent partner present in the sample.

In some embodiments, a detectable fractional sub-population of a binding partner of a binging agent in the sample may be predetermined. This may be done by using a mixture of binding molecules of the binding agent, wherein the binding molecules of the mixture are all of the same species and have essentially the same affinity to the (common for all said binding molecules) binding partner in the sample ("essentially" in the present context means that +/−10% difference in the affinity is included), and wherein a portion of said binding molecules is detectably labeled and a portion of said binding molecules is unlabeled, and the both portions are predetermined. The term "labeled binding molecules" means that said binding molecules are associated/linked to a detectable label, e.g. a fluorescent label or enzyme. In one embodiment, the label is an enzyme; in one embodiment the enzyme is an oxidoreductase enzyme, (such as a described above, e.g. HRP). The unlabelled binding molecules do not comprise any detectable label.

In one such embodiment, the binding agent may be a first binding agent that is capable of binding to a single unit of the target and form a complex with said single unit. In another such embodiment, the binding agent may be a second binding agent that has affinity to the first binding agent bound to single target unit in the sample. In some embodiments, the binding agent may be a third binding agent that is capable of binding to the second binding agent, or to a label linked to the second binding agent, or to a reporter deposit at a target site.

Using the binding agent (as any of the mentioned) comprising a predefined ration of labeled and unlabeled binding molecules, it is possible to quantify the amount of a target in the sample precisely by quantifying the target sites (visualized as dots) formed with the labeled binding agent. Methods of quantification of the target in histological samples using mixtures of labeled and unlabelled binding molecules are described in more detail below.

Following the incubation in a binding agent medium, the sample is incubated in an aqueous solution (A) (also termed herein as "reporter deposition media" or "RDM") comprising a first substrate of the enzyme with oxidoreductase activity and, a second substrate of the enzyme with oxidoreductase activity and a peroxide compound.

Optionally, before the incubation in the aqueous solution (A), the sample may be incubated in an aqueous solution (B), which composition is as of an aqueous solution (A) without the second substrate.

Accordingly, in one embodiment the invention relates to incubation media which is in an aqueous solution (A) and in another embodiment the invention relates to incubation media which is an aqueous solution (B).

Both aqueous solution (A) and aqueous solution (B) may be an aqueous buffered solution with a suitable buffer capacity, e.g. phosphate buffered saline (PBS) and imidazole buffer. The pH value of the solutions may be adjusted in order to achieve the technical effect of the incubation, namely formation of discrete deposits of the second substrate of an enzyme with oxidoreductase activity at discrete single target sites of the invention, for example adjusted to pH ranging from about 4 to about 9. However, pH of the aqueous solutions (A) and (B) is of minor importance for the technical effect of the incubation.

Both aqueous solution (A) and aqueous solution (B) may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in an aqueous solution (A) and aqueous solution (B) may range from approximately $10^{-3}$ M to saturation, e.g. from approximately 20 mM to approximately 200 mM, or from approximately 50 mM to approximately 500 mM. In one embodiment, the media may comprise salt in the amount from approximately 10 mM to 500 mM. In another embodiment the medium may be free of salt.

Both aqueous solutions (A) and aqueous solutions (B) may in different embodiments further comprise: an organic modifier and/or, an enzyme enhancer, and/or an iron chelator, and/or a detergent, and/or an anti-microbial agent.

The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-7}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

Essential components of an aqueous solution (A) are a first substrate of an enzyme with oxidoreductase activity, a second substrate of said enzyme and a peroxide compound.

Embodiments of the first substrate and the second substrates are discussed in detail above.

In one embodiment the first substrate may be 3,3"-diaminobenzidine (DAB) or a derivative thereof. In another embodiment, the first substrate may be ferulic acid or a derivative thereof.

The amount of the first substrate in an aqueous solution (A) may vary depending on the compound chosen as the first substrate (see discussion above). For example, in embodiments, when DAB is chosen as the first substrate, the amount of DAB in an aqueous solution (A) and in aqueous solution (B) is less than 1.4 mM, and may be less than 1.2 mM, or less than 1 mM, such as from around 0.005 mM to around 0.5 mM, for example around 0.3 mM, or around 0.2 mM, such as around 0.15 mM, etc. In embodiments when ferulic acid is used as the first substrate, the amount of said compound is less than 2.5 mM, and may be less than 2 mM, e.g. around 1.5. mM. The term "around" in the present context means +/–0.05-0.5 mM.

Amounts of the other first substrates of the invention in the aqueous solutions (A) or (B) are discussed in the previous sections.

The aqueous solution (i) may comprise various amounts of the second substrate of the enzyme, such as from about $10^{-10}$ M to about $10^{-4}$ M. For example, in embodiments when the second substrate (as any of the described above) comprises a radioactive label, an applicable amount may be in the range from about $10^{-10}$ M to about $10^{-6}$ M. In other embodiments, e.g. when the second substrate comprises a fluorescent label or a label which is a member of a specific binding pair, the amount may be in the range from about $10^{-9}$ M to about $10^{-4}$ M.

In one embodiment, an aqueous solution (A) may comprise a population of identical conjugate molecules of second substrate. In another embodiment, an aqueous solution (i) may comprise a population of different conjugate molecules of second substrate.

A peroxide compound of the invention is hydrogen peroxide, however, other peroxide compounds may also be used in different embodiment, e.g. in some embodiments it may be an organic peroxide such as e.g. tert-butyl peroxide, ditert-butyl peroxide, peracetic acid, etc, or in some embodiments it may be an adduct of hydrogen peroxide, such as hydrogen peroxide urea adduct.

The amount of a peroxide compound in an aqueous solution (i) and an aqueous solution (ii) may not be higher than 5 mM, and may be less than 5 mM, including in the range of 0.1 mM to 5 mM, e.g. between 0.1 mM and 1 mM, between 1 mM and 2 mM, between 2 mM and 3 mM, or between 3 mM and 4 mM, including in the range between from around 1 mM to around 2 mM, such as around 1.5 mM. The term "around" in the present context means +/–0.05-0.5 mM An aqueous solution (A) comprising a first substrate of enzyme with oxidoreductase activity, a second substrate of said enzyme and a peroxide compound is termed herein "deposition medium".

An aqueous solution (B) may comprise the same compounds in the same amounts as an aqueous solution (A), with the exception that the aqueous solution (ii) does not comprise the second substrate of enzyme with oxidoreductase activity.

In some embodiment a sample comprising single target sites may be initially incubated in an aqueous solution (B) and sequentially in an aqueous media (A).

In another embodiment a sample comprising single target sites is incubated an aqueous solution (A), without preincubation in an aqueous solution (B).

According to the invention the deposition media is a stable solution, i.e. no precipitation of the solved compounds occurs for a relatively long period of times, such as at least 5 hours. To prolong the shelf-life of the media it may be useful to store the media at temperatures below +20° C., e.g. at +4-+10° C., and/or to add to the media an anti-microbial compound. The anti-microbial compound may be any anti-microbial compound commonly used for such purpose, e.g. sodium azid, Proclin™ or Bronidox®.

In one embodiment the invention relates to a method comprising one or more steps following the step (b) which comprise detection of discrete single deposits of the second substrate at single target sites, e.g. a sample comprising discrete deposits of the second substrate may be incubated in incubation media comprising a binding agent capable of specifically binding to a detectable label of the deposited molecules of second substrate.

An incubation medium comprising a binding agent capable of specifically binding to a detectable label of the deposited molecules of second substrate will typically have a similar or the same composition as the binding agent medium discussed above.

The binding agent bound to a detectable label of the deposited second substrate may in one embodiment comprise an enzyme, e.g. horse radish peroxidase (HRP) or alkaline phosphotase (AP). Such binding agent can be detected using a standard visualization system employing chromogenic substrates of the enzymes, e.g. an enzyme substrate solution or a color developing solution. This kind of media may be any suitable media known in the art which is to be selected depending on available means for visualization and following the common general knowledge of the art concerning the nature of the detectable label of the deposits.

Alternatively, in case the binding agent comprises HRP, the visualization method of the invention may comprise a further step of incubation of a sample comprising discrete deposits of the second substrate bound to the binding agent in the deposition media described above. Such further step may be advantageous in some embodiments when a signal associated with the deposited second substrate may weak, or the size of the primary deposit is relatively small. The additional deposition step allows further amplification of the signal associated with the deposit and it may also increase the size of recognizable deposits at single target sites. Further, the step also allows modifying the character of the recognizable signal, e.g. changing spectral characteristics of the signal, e.g. the initial label detectable as a red signal may be substituted for a label detectable as a green signal by using conjugate molecules comprising said green label for this additional deposition instead of conjugate molecules comprising a red label used for the initial deposition (at step (b) of the method). Such flexibility of the method of the invention, however do not add an extra complexity to reagents used in additional steps of detection, as all embodiments of incubation media of steps (a) and (b) (discussed above) of the method may be successfully used without substantial modifications in these addition steps.

In one embodiment the invention relates to washing media, i.e. media for removing the rests of compounds (of incubation medium) from the sample after the technical effect of the incubation has taken place. The method of the invention may comprise one or more washing steps typically following a step of incubation of the sample in media described above, e.g. between steps (a) and (b), etc. Typically, a washing medium will be the same medium that has been used for incubating of the sample in a step preceding the washing step without the essential compounds of the incubation media, i.e. without binding agent, substrates of the enzyme, etc.

In one embodiment, the invention relates to a media for quenching the endogenous oxidoreductase activity. This type of media may be any media of such kind that is routinely used for the purpose in the art, for example a solution of hydrogen peroxide. This medium may be used before step (a) of the method. It can also be used after step (b) and before additional steps of detection of the deposited second substrate. Application of this medium at this stage of the procedure may used for quenching the residual oxidoreductase activity in the sample.

So, the methods and systems for analyzing images of specimens processed by a programmable quantitative assay, can be seen to have significant advantages in terms of image processing simplicity and speed. Also a wide variety of diagnostic and non-diagnostic applications have been described in the various embodiments. The programmability of optical features and the discrete and distinct nature of the dots produced provide many benefits as compared to historical chemical and immunohistochemical imaging of stained specimens.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

It has been found that using particular conditions of deposition media comprising particular conjugate molecules of the second substrate of enzyme with oxidoreductase activity and relatively low amounts of the first substrate of enzyme with oxidoreductase activity a peroxide compound, such as DAB and hydrogen peroxide, it is possible to form discrete deposits of said conjugate molecules at single target sites of the invention that have distinct physical features, namely round-shaped deposits larger than 0.4 micrometer in diameter, which can be directly observed using a regular microscopic optics or visualized as distinct dots. Using a similar amplification system (that employs the HRP-DAB mediated deposition of detectable conjugate molecules it has been possible to improve the traditional HRP-DAB IHC staining in that the homogeneous color pattern of target staining has become more crisp improving thereby the intracellular resolution of cellular structures, e.g. membrane, cytoplasm, and nucleus. The present visualization system provides instead a dotted pattern of target staining, wherein one single dot correspond to one individual target unit, such as one individual target molecule, allowing thereby the intracellular resolution of individual single target units such as single target molecules.

The deposits of detectable conjugate molecules of the invention produced by the method of the invention are three dimensional and have a substantially spherical shape, which in a two dimensional field, e.g. a microscopic field, are observed as distinct substantially rounded dots. Accordingly, the term "rounded dot" (interchangeably used herein with terms "dot" and "distinct dot")" designates in the present context a spherical deposit of recognizable conjugate molecules of the invention observed in a two-dimensional field as a distinct substantially rounded dot. The term "distinct" in the present context means that a dot of the invention is distinguishable to the eye or mind as discrete The term "substantially rounded" means that a distinct dot of the invention has eccentricity that is around or less than 0.65. A dot according to the invention has a diameter of around or greater than 0.4 microns. The term "around" in the present context means +/−0.05-0.5 micrometer. In comparison, a "dot" of a deposit of the DAB stain by the traditional DAB-HRP method, or a single deposit of the stain at target sites obtained by some conventional methods, or biotinyl- and fluorescyl-tyramide deposits by the CARD method has a size that is under the resolution limits of the regular microscopic optics (such as 4× or 10× magnification bright field or fluorescent optics), e.g. less than 0.1 microns. Accordingly, it is impossible to directly observe individual single target units visualized by the latter methods in a low magnification microscopic field (such as 4× or 10×). The method described herein allows detecting and visualizing single deposits of recognizable conjugate molecules of the invention at single target sites and thereby observe immobilized single units of targets in samples using low-magnification optics.

The term "one single deposit of the second substrate" (of enzyme with oxidoreductase activity) or "one single deposit of detectable conjugate molecules" (of the invention) relates to a single accumulation of a plurality of conjugate molecules of the second substrate. According to the invention, one distinct deposit of second substrate the invention may comprises from about 1000 and up to 1000000 conjugate molecules or more.

As discussed above, the second substrate deposited at a single target site may comprise visually identifiable molecules, e.g. molecules that comprise a visually detectable label, e.g. a fluorescent label. Accordingly, in one embodiment, a dot of deposit of such second substrate may be detected by a microscopist by using a conventional fluorescence microscope straight after the deposit has been formed. Deposits of reporter molecules that comprise labels that are not directly observable by standard microscopic optics, e.g. a member of a specific binding pair, are to be visualized according to the invention using at least one an additional step detection step, e.g. an additional step (c) described above.

The number of dots, their size and visual appearance can be controlled. For example, in different embodiments dots of a particular size and particular appearance (e.g. particular color) may be produced.

In one embodiment, the size of deposit and the dot size may be varied by using binding agents involved in formation of target sites of the invention comprising different number of enzyme moieties (the terms "enzyme moieties" or "enzyme" is in the present context mean an enzyme with oxidoreductase activity), e.g. the number of HRP per binding agent. In another embodiment the dot size may be controlled by duration the deposition process. In another embodiment, the dot size may be regulated by the content of the deposition media, such as the amount of first and/or second substrates, or a peroxide compound in the deposition media.

Thus, in one embodiment the number of the enzyme units per molecule of binding agent used for formation of a target site may influence the size of a dot. It is found that the dot size may be directly correlated to the number of the enzyme moieties per complex comprising one or more binding agents and one single unit of a target: Larger dots are observed when binding agents used for formations the target sites comprise a larger number of enzyme moieties per molecule (under otherwise the same deposition conditions (i.e. same incubation time, same composition of the deposition media) compared to the dots obtained with use of the same binding agents, but comprising less enzyme moieties per molecule.

To produce a visible dot corresponding to one single deposit under conditions of the invention, it is sufficient that the target site comprises a single, i.e. one enzyme moiety, e.g. a binding agent involved in formation of a target site comprises a single HRP moiety; however, in embodiments when two or more enzyme moieties are present at the same target site, the dot associated with this target site is larger than the dot in the first case. Accordingly, in one embodiment, a binding agent associated with one single target site may comprise one single moiety of HRP, in another embodiment, the binding agent may comprise two or more moieties of HRP, e.g. 2, 3, 4, 5, 6, 7, 8, 9 or 10. In one embodiment, the number of the enzyme moieties per binding agent is at least 2, including from 3 to 10, such as from 4 to 8 moieties.

It was surprisingly found that using binding agents that involved in formation of target sites of the invention wherein the number of enzyme moieties is at least 2 per molecule of binding agent, it is possible to produce dots of approximately equal size, under otherwise the same conditions, i.e. same conditions of the visualization procedure. Accordingly, in one embodiment, the invention relates to a method, wherein a sample comprising a immobilized target is incubated to one or more binding agents, wherein at least one of the binding agent comprises at least two enzymes with oxidoreductase activity. Thus, individual units of the target in this embodiment are visualized as individual substantially identical dots, i.e. as dots of the same size. In one embodiment the pool of molecules of a binding agent comprising an enzyme with peroxidase activity may be heterogeneous in that said molecules of comprise different number of the enzyme moieties per molecule, such as e.g. between 2 and 10 molecules, between 11 and 20 molecules, etc. In another embodiment, invention relates to the method, wherein every molecule of the pool of molecules of binding agent comprising an enzyme with peroxidase activity comprises the substantially identical number of the enzyme moieties per molecule of the binding agent, such as 1-3, 2-4-, 3-5, 4-6, 5-7, 6-8, 7-9, 8-10, 9-11, 10-12 etc. enzyme moieties per binding agent molecule.

In another embodiment the size of a dot is regulated by the amount of the first substrate in a deposition media, e.g. by the amount of DAB. Large dots, i.e. the dots which diameter is equal or larger than 0.4 microns, or equal or larger than 1 micron, or equal or larger than 2 or 3 microns, such as 4 or 5 microns, wherein the amount of deposited reporter (per dot) is not less than 1000 molecules, may be formed when the amount of DAB in the deposition media (in otherwise the same conditions of the visualization procedure, i.e. same binding agent, same reporter, same amount of the reporter, same concentration of the peroxide, same incubation time, etc) is in the range from about 0.01 mM about 1 mM, e.g. between 0.05 mM and 0.75 mM, such as from around 0.075 mM to around 0.5 mM, such as from around 0.1 mM, e.g. 0.15 mM, or around 0.3 mM, e.g. 0.28 mM, etc. Dots of a smaller size, i.e. less than 0.4 microns, may be observed when both the higher and lower amounts of DAB in deposition media are used.

Composition and structure of the conjugate molecules of the inventions influence the capability of said molecules to be deposited as the second substrate of the invention (discussed above), and therefore they influence size of the deposits and apparent size of a dot. Further, a label of the conjugate may influence the appearance of a dot. For example, in embodiment when the conjugate molecule comprises a fluorescent label, the nature of the fluorofore group of the label will influence the appearance of the dot, e.g. under identical conditions conjugates comprising Lissamine (red fluorofore group) produce more intense dots than similar conjugates comprising Fluorescein (green fluorofore group). Further, higher amounts of the second substrate in the deposition medium, under otherwise the same conditions, may lead to formation of larger deposits.

The size of a dot may also be regulated by the time used for deposition of the second substrate. Longer incubation time in a deposition media allows depositing a larger amount of conjugate molecules at single target sites, increasing thereby the size of a single deposit and sequentially the size of a single dot. Increasing incubation time from 30 seconds to 10 minutes, in otherwise the same conditions, i.e. the same binding agent, same media, etc, may allow to the enzyme producing deposits that can be observed as single dots of a diameter around 5 micrometer. However, a further increase in duration of the incubation does not increase the size of a single deposit. However, longer times of the incubation in the deposition media do not decrease the size of single deposits, and if desirable, longer incubation times, e.g. up to 20 or 30 minutes or longer may be used. Thus, in different embodiments the duration of the deposition step of the method may vary from about 30 seconds to about 20 minutes, e.g. 1, 2, 3, 4, 5, 10, or 15 minutes, e.g. in one embodiment, the incubation time may be about 30 seconds, in another embodiment the time may be about 2 minutes. In one embodiment conjugate molecules may be deposited during 5-10 minutes.

The amount of a peroxide compound in the deposition media may also be used as a factor for the regulation of size of the reporter deposit and, accordingly, the dot size. To obtain single dots that are up to 5 micrometers in diameter, the amount of a peroxide compound, such as e.g. hydrogen peroxide, in the deposition media should be less than 2 mM, and in some embodiments the amount may not exceed 1.5 mM. Higher amounts of a peroxide compound lead to formation of dots of a smaller size.

All the factors discussed above are termed in the present context "primary factors" as they influence formation of the initial, i.e. primary deposit of the second substrate. As mentioned, such primary deposits may be observed immediately after the deposition has taken place, e.g. in case conjugate molecules of the second substrate comprise a fluorescent label. In other embodiments, the primary deposits are not directly observable, however they may be visualized in one or more detection steps (termed in the present context "secondary visualization procedure") following the deposition step, e.g. in case the conjugates comprise a label that is a member of a specific binding pair, e.g. a hapten. Several factors of the secondary visualization procedure may also influence the visual size and appearance of the deposit as a dot, adding thereby to flexibility of the visualization system of the present invention. These factors are termed "secondary factors" accordingly.

The deposits of reporter molecules comprising a label that is a member of a specific binding pair may be visualized performing following detection steps (c') and (c") which directly or indirectly follows the deposition step:

(c') incubating a sample comprising discrete deposits of second substrate at single target sites with one or more binding agents capable of directly or indirectly binding to a detectable label of the deposited second substrate, wherein at least one of the binding agents comprises one or more detectable labels selected from radioactive, fluorescent or luminescent substances, members of specific binding pairs, or enzymes, thereby forming a complex comprising the deposited reporter and said at least one binding agent, (c") detecting in the sample the binding agent comprising the detectable label, thereby visualizing one or more reporter deposits at one or more individual target sites, and thereby visualizing one or more individual units of the target in the sample.

The term "indirectly" in the present context means that it may be one or more optional steps between the step (b) and (c'), e.g. a washing step.

By using reporter recognizing binding agents that comprise multiple enzyme moieties (as detectable labels) that can utilize chromogenic or fluorescent substrates, e.g. HRP or alkaline phosphotase (AP), it is possible to "stain" the deposits and produce distinct visibly detectable dots. In this case, the original size of a single deposit may be "increased" or "decreased" by producing a distinct visually detectable dot of a certain size. In one embodiment, using a binding agent labeled with HRP or another oxidoreductase enzyme, and optimal conditions of the deposition (discussed above) the step of deposition may be repeated one or more times, thereby increasing the size of a detectable deposit at a single target site after every repetition. In another embodiment, using a binding agent labeled with HRP or another oxidoreductase enzyme, and sub-optimal conditions of the deposition (discussed above), the deposition step may be repeated yielding in deposits of a smaller size and, accordingly, smaller size of H the corresponding detectable dots. In one embodiment, the deposition step may be repeated using conjugate molecules as second substrate which are different from the conjugate molecules used for the primary deposition, e.g. comprising another label, e.g. Lissamin label instead of Fluorescein label. In other embodiment, deposition time or deposition media conditions may be optimized to produce smaller or larger secondary deposits at the primary single target sites.

Thus, the visualization system used in of the present invention is a flexible and powerful amplification system. The double regulation system provide en extra flexibility which may be particular advantageous in some embodiments, e.g. in an embodiment when it is desirable to visualize large primary deposits as dots of smaller size. Dots of a smaller size may allow a more precise target unit positioning in the sample and also may allow detection of a larger dynamic range of target.

The double regulation described above may also be desirable in embodiments when two or more different targets are to be detected, or in embodiments when a target is present in the sample in a broad dynamic concentration range, or in embodiments when the primary deposit provides a weak detectable signal, etc. Visualization and quantification of targets present in a sample in a broad dynamic concentration range, i.e. there is a gradient of target concentration in the sample, may be challenging. At the lowest end of the range the number of the target site related dots may be insufficient to provide statistically valid information about the presence of the target throughout the entire sample, whereas at the highest end of the dynamic range, visualization of single units of the target may be challenged by the presence of a number of overlapping dots that cannot be visually distinguished separately from each other. Use of the primary and/or secondary factors described above to decrease an apparent size of the dots corresponding to large primary deposits may allow overcoming these problems and visualize and quantify targets present in samples in broad dynamic ranges.

Methods of detection of primary deposits of the second substrate may be different depending on type of the sample, features of the deposited molecules, etc. Any suitable method of the art may be used, e.g. in histological samples the deposits may be detected by using any standard IHC staining e.g. HRP-DAB staining, ELISA visualization or immunoblot staining may be used in other embodiments, etc.

EXPERIMENTAL EXAMPLES

Example 1. Quantification of a Target in a Histological Sample

In order to define a number of single entities of a target in a sample and, in particularly, total number of said units, e.g. single target protein molecules, several complex equilibrium experiments may be performed, employing:

Several Reference samples of a test material with identical, but unknown, levels of an immobilized protein molecules, Pr. (e.g. serial sections of a single block of homogeneous Her2 reference cells lines);

A primary antibody, Ab1 (e.g. a high affinity monoclonal Rabbit-anti-HER2) with unknown dissociation constant, Kd1 that binds to said protein, An Enzyme labeled secondary antibody, Ab2 with unknown dissociation constant, Kd2, that binds to said primary antibody.

According to the present invention the level of immobilized target in a sample, e.g. a protein, can be expressed as counted single molecule dots (PDQA) per nucleus (e.g. in reference cell lines samples), or per area or volume of a tissue sample, etc; the number of molecules can via Avogadro's Number be translated into concentration of said molecules in the sample.

It is generally accepted that theoretical framework for antibody protein interaction is a complex equilibrium. The antibody will reach equilibrium with the target protein:

$$Ab1+Pr \leftrightarrow Ab1{:}Pr \qquad \text{F1}$$

Governed by the dissociation constant, Kd1 of the antibody:

$$\frac{[Ab1] \times [Pr]}{[Ab1{:}Pr]} = Kd1 \qquad \text{F2}$$

Under such equilibrium conditions, total protein, PrTotal and total antibody, Ab1Total will be distributed between free protein and complex and free antibody and complex.

$$PrTotal = Pr + Ab1:Pr \quad\quad\quad F3$$

$$Ab1Total = Ab1 + Ab1:Pr \quad\quad\quad F4$$

From F2 follows:

$$[Pr] = \frac{[Ab1:Pr] \times Kd1}{[Ab1]} \quad\quad\quad F5$$

Substituting F5 into F3 gives:

$$PrTotal = \frac{[Ab1:Pr] \times Kd1}{[Ab1]} + [Ab1:Pr] \quad\quad\quad F6$$

F6 can then be rearranged as the following:

$$PrTotal = [Ab1:Pr] \times \frac{Kd1 + [Ab1]}{[Ab1]} \quad\quad\quad F7$$

The first experimental challenge lies in determining when this first equilibrium has been reached. [Ab1:Pr] can be detected and determined by a subsequent second equilibrium experiment with enzyme labeled Ab2 followed by PDQA visualization. The first series of experiments, Exp1, can be used to establish that a sequential application of a constant concentration of Ab1 to samples with a constant amount of immobilized protein will eventually result in a constant amount of Ab1:Pr being detected in a subsequent second visualization step using enzyme labeled Ab2 and PDQA detection.

The need to use multiple sequential additions of Ab1 arises from the fact that a single addition of Ab1 to a sample with immobilized protein will result in Ab1:Pr complex formation, and thus in a decrease in both Ab1 and Pr concentration. The first equilibrium may apparently be reached, but sequential additions of Ab1 to identical reference samples until a constant level of Ab1:Pr is detected must be used to access when a true equilibrium reflecting the concentration of Ab1 has been reached, i.e. when further additions of Ab1 will no longer result in an increase in Ab1:Pr being detected. A single or a few additions of Ab1 will result in equilibriums reflecting the total amount of protein in the immobilized samples rather than the concentration of Ab1. Ab1 will be depleted due to complex formation and the effective concentration in equilibrium will be significantly lower than the concentration of Ab1 applied.

Formula 4 reflecting the effects of lowered concentration of free antibody can be ignored, if multiple additions of antibody confirm that depletion or slow kinetics is not a case.

Experimental set-up to confirm the above theory may be designed as the following: A constant concentration of Ab1 is sequentially applied to samples with constant concentration of immobilized protein. The Ab1:Pr complexes formed are subsequently detected using an enzyme labeled secondary antibody and PDQA visualization. Thus, a true equilibrium reflecting the concentration of Ab1, not the amount of immobilized protein, can be established. (The experiment confirming this theory is described below in experiment 12.3a, which shows that, after four to five sequential 10 min-incubations reference samples with Ab1 no further increase in Ab1:Pr complexes is detected).

The theory behind the second complex equilibrium step is identical to the theory regarding the first (discussed above).

The second equilibrium is established between the enzyme labeled secondary antibody and the immobilized primary antibody protein complex:

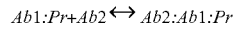

$$Ab1:Pr + Ab2 \leftrightarrow Ab2:Ab1:Pr \quad\quad\quad F8$$

Governed by the dissociation constant, Kd2 of the labeled secondary antibody:

$$\frac{[Ab2] \times [Ab1:Pr]}{[Ab2:Ab1:Pr]} = Kd2 \quad\quad\quad F9$$

$$Ab1:PrTotal = Ab1:Pr + Ab2:Ab1:Pr \quad\quad\quad F10$$

$$Ab2Total = Ab2 + Ab2:Ab1:Pr \quad\quad\quad F11$$

From F9 follows:

$$[Ab1Pr] = \frac{[Ab2:Ab1:Pr] \times Kd2}{[Ab2]} \quad\quad\quad F12$$

Substituting F12 into F10 gives:

$$Ab1:PrTotal = \frac{[Ab2:Ab1:Pr] \times Kd2}{[Ab2]} + [Ab2:Ab1:Pr] \quad\quad\quad F13$$

F13 can then be rearranged into F14

$$ab1:PrTotal = [Ab2:Ab1:Pr] \times \frac{Kd2 + [Ab2]}{[Ab2]} \quad\quad\quad F14$$

This second equilibrium can only be established, if the concentration of Ab1:Pr remains essentially constant during the second equilibrium experiment, i.e. that no significant dissociation between protein and primary antibody takes place during washing steps and incubation with enzyme labeled secondary antibody. If this condition is observed, it is possible to substitute Ab1:PrTotal of Formula 14 for [Ab1:Pr] of Formula 7.

This gives the next equation (Formula 15):

$$PrTotal = [Ab2:Ab1:Pr] \times \frac{Kd1 + [Ab1]}{[Ab1]} \times \frac{Kd2 + [Ab2]}{[Ab2]} \quad\quad F15$$

Formula 15 can be regarded as the theoretical foundation of the absolute count experiments, i.e. experiments where the total number of target molecules in a sample is determined, because it describes a relationship between Kd1 and Kd2, which can be determined in equilibrium experiments in connection with the antibody titrations, and the total protein concentration and complexes of the protein with the antibodies that are visualized as dots.

These experiments may be performed as the following: A constant concentration of Ab1 is sequentially applied to samples with constant concentration of immobilized protein.

The Ab1:Pr complexes formed are subsequently detected using an enzyme labeled secondary antibody and PDQA visualization. The enzyme labeled secondary antibody (a constant amount thereof) is likewise sequentially applied multiple times. The experiment confirming this theory (described in experiment 12.3b) has shown that after four to five sequential 10 min-incubations of enzyme labeled Ab2 with reference samples previously equilibrated with primary antibody no further increase in formation of Ab2:Ab1:Pr complexes was detected, neither a decrease (potentially resulting from a significant protein-Ab1 dissociation during washing steps and establishment of the second equilibrium) was detected. Thus, a true equilibrium reflecting the concentration of immobilized protein, [Ab1] and enzyme labeled [Ab2] can be established confirming the equation of Formula 15.

For the same reasons as discussed for Formula 4, now Formula 11 may be ignored. The effects of lowered concentration of free secondary enzyme labeled antibody can be ignored if multiple additions of this antibody confirm that depletion or slow kinetics is not a problem.

Tissue samples with unknown protein concentration level may be routinely incubated with primary antibodies in order to determine said unknown protein concentration. This step may be followed by steps of incubation with enzyme labeled secondary antibody followed by, yet, extra steps of visualization.

As a rule, in routine IHC staining procedures only single incubations with primary and secondary antibodies are used, and a physical agitation, either uncontrolled (due to gravity, evaporation or wicking) or controlled by active stirring of reagents on the slide, is an established practice. However, using mixing and/or relative high concentrations of both primary and secondary antibody, pseudo equilibrium conditions may be reached by a single reagent application, resulting in reproducible results (this is how the well-known histological staining systems work now, e.g. Envision system). Consecutive additions of an antibody reagent (primary or enzyme labeled secondary) results in relative stable equilibriums, and thus can also act as a safeguard against antibody depletion and allow, in contrary to the traditional IHC staining, the precise evaluation of the amount of the target in an IHC sample.

As described in experiments below, the necessity of use of low amounts of high affinity primary antibody arises from the low value of Kd1 of the Her2 clone tested in combination with the need to use concentrations below Kd1 in order to measure Kd1. For routine use concentration well above Kd1 may be used, reducing the need for multiple additions. In case of the secondary antibody, it is the need to reduce dot overlap that prevents use of higher concentration. At higher concentrations the overlapping dots may prevent an accurate dot count, at least when counting is done manually.

When the staining conditions leading to forming non-overlapping PDQA dots are observed, the PDQA dots can be counted as Pr, and, if PrTotal can be kept constant (e.g. in case of use of sequential sections of same reference material), experiments with varying [Ab1] and constant [Ab2] will allow determining Kd1; PrTotal and Kd2 will still remain unknown, but constant. This allows rearrangement of Formula 15 into Formula 16:

$$\text{Dots} = \text{Constant} \times \frac{[Ab1]}{Kd1 + [Ab1]} \qquad \text{F16}$$

The Constant (C) reflects the value of PrTotal of the sample and the fraction of Ab1:Pr complexes that are detected in the second equilibrium reaction with constant [Ab2]. And it is the absolute number of Dots that can be detected under those conditions. The equation of F16 means that at high and increasing [Ab1] the number of Dots will approach, but never reach a constant level. At low and decreasing [Ab1] the number of Dots, which is a hyperbolic function of [Ab1], will approach a linear function of [Ab1].

The number of Dots as function of [Ab1] is a hyperbolic function, and Formula 16 is used to determine Kd1 by fitting experimental data correlating Dots with [Ab1] in experiments with constant reference material and constant [Kd2]. However, using sequential additions of Ab1 at concentrations close to Kd1 reproducibly allow accurate determination of Kd1 via an excellent fit to Formula 16.

Experimental set-up that allows determination of Kd2 is slightly more complex. The challenge is that concentrations of enzyme labeled secondary antibody that are close to Kd2 invariably will lead to formation of dots the number of which will be too high to count due to overlap problems. Use of a very low concentration of primary antibody and/or use of reference material with a low protein concentration would not be a solution, as a background from high concentrations of secondary antibody will give a very high background noise due to unspecific bound secondary antibodies, thus would not accurately reflect the protein concentration. This is further compounded by difficulties of establishing the equilibrium at very low primary antibody concentrations. An approach to overcome these challenges is to use both primary and secondary antibody in relative high concentrations, in case of the secondary antibody with concentrations around Kd2, and visualizing the bound secondary antibody by conventional IHC. By conventional IHC is meant that the enzyme labeled secondary antibodies are used to generate a brown deposit of 3,3'-diaminobenzidine (DAB), e.g. by using the Envision system, rather than PDQA visualization. The intensity of such conventional DAB deposits is not linear and does not correctly reflect the quantity of molecules of a target in the sample, however the intensity of two deposits may be visually compared and determined to be of approximately of the same intensity. Indeed, this is how the IHC-staining results are at present interpreted: they are evaluated by comparing the intensity of the brown deposit in test samples and reference samples and follow the graphic or descriptive guidelines for the interpretation.

Using identical reference material, PrTotal (of F15) can be kept constant. If [Ab1] and [Ab2] are also constant, and Ab2:Ab1:Pr is visualized by conventional IHC as a brown deposit, the staining will be of constant intensity. Evidently, the intensity has to be within the dynamic range of conventional IHC so that variations in Ab2:Ab1:Pr are reflected in variable intensity of the brown deposit. IHC slides are normally scored on a scale: 0 (negative) (no color at all), 1+(weakly positive), 2+(moderately positive), and 3+(highly positive/brownish-black). In order to accurately reflect [Ab1:Ab2:Pr], the score should be within the 0.5+ to 2.5+ range, so that upwards or downwards variation is detected, including within the 1+ to 2+ range, where the intensity variation as function of [Ab1:Ab2:Pr] is most pronounced and the background noise is minimal.

Having established a reference system in the desired dynamic range (i.e. within 1+ to 2+ and [Ab2] around [Kd2]) experiment 12.3d (described below is carried out using a lower constant concentration of Ab1, $[Ab1]_2$ with variable and increasing concentration of Ab2 relative to the initial reference experiment By increasing [Ab2], the concentration of [Ab2:Ab1:Pr] will at some point reach a level identical to the prior established reference level, resulting in an identical intensity of brown deposit. When the intensity of the brown DAB deposit is of identical intensity to the deposit formed with [Ab1]$_1$ and [Ab2], it is to be concluded that:

$$[Ab2:Ab1:Pr]_1 = [Ab2:Ab1:Pr]_2$$

Thus, the identical staining levels have been reached by two different combinations of [Ab1] and [Ab2] and constant PrTotal. It follows to the equation:

$$\frac{Kd1+[Ab1]_1}{[Ab1]_1} \times \frac{Kd2+[Ab2]_1}{[Ab2]_1} = \frac{Kd1+[Ab1]_2}{[Ab1]_2} \times \frac{Kd2+[Ab2]_2}{[Ab2]_2}$$

As Kd1 is known, as well as [Ab1]$_1$ and [Ab1]$_2$ from experimental conditions, the equation may be reduced to Formula 17 (C1 and C2 are Constants):

$$C_1 \times \frac{Kd2+[Ab2]_1}{[Ab2]_1} = C_2 \times \frac{Kd2+[Ab2]_2}{[Ab2]_2} \quad \text{F17}$$

Dividing by $C_1$ gives:

$$\frac{Kd2+[Ab2]_1}{[Ab2]_1} = C_3 \times \frac{Kd2+[Ab2]_2}{[Ab2]_2} \quad \text{F18}$$

Formula 18 may be rearranged to allow isolation of Kd2:

$$(Kd2 \times [Ab2]_2) + ([Ab2]_1 \times [Ab2]_2) = (C_3 \times Kd2 \times [Ab2]_1) + (C_3 \times [Ab2]_1 \times [Ab2]_2),$$

which can be reduced to:

$$Kd2 = \frac{(1-C_3) \times ([Ab2]_1 \times [Ab2]_2)}{(C_3 \times [Ab2]_1) - [Ab2]_2} \quad \text{F19}$$

Where $C_3$ (which is equal to C2/C1, see above) is defined by:

$$C_3 = \frac{(Kd1+[Ab1]_2) \times [Ab1]_1}{[Ab1]_2 \times (Kd1+[Ab1]_1)} \quad \text{F20}$$

$C_3$ relates to two hyperbolic functions on top of each other reflects a constant level of the brown staining that is derived from two different sets of experimental conditions: first, a reference level is established by reaching a first equilibrium reflecting [Ab1]$_1$ and [Ab2]$_1$: then, the same reference level is reached by using [Ab1]$_2$ and [Ab2]$_2$. Kd1 is known, Kd2 can thus be determined.

A reference level of the conventional staining intensity may be produced using [Ab1]$_1$ and [Ab2]$_1$. Using a different concentration of Ab1, [Ab1]$_2$ allows titration of [Ab2] until a level of identical staining intensity is reached by [Ab2]$_2$. This allows determination of Kd2 from Formula 19.

Returning to the original Formula 15, having determined Kd1 and Kd2, any PDQA staining experiment fulfilling the proviso of reaching equilibrium in both steps and allowing an accurate PDQA dot count, will allow determination of PrTotal in the reference sample(s) used.

Any reference sample, wherein PrTotal has been determined in this way, obtains a status of "absolute reference".

The absolute number of proteins (or any other immobilized target compound) in the immobilized sample has been counted and may be expressed in absolute terms such as molecules per area/volume/cell etc. depending on the nature of the immobilized sample.

Experimental Support

Abbreviations

MBHA 4-Methylbenzhydrylamine
NMP N-Methyl Pyrolidon
HATU 2-(1h-7-azabenzotriazole-1-yl)-1,1,3,3 tetramethyl uronium hexafluorophosphate; methenamminium
DIPEA DiIsopropyl EthylAmine
DCM Dichloro Methane
TFA TriFluoroacetic Acid
TFMSA TriFluor Methyl Sulphonic Acid
Flu Fluorescein
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane
L60, L90, L120, L150 different polymers of L30, comprising 2, 3, 4 or 5 L30 repeats
ClZ 2-chloroZ=2-chloro Benzyloxycarbonyl
FITC FlouresceinIsoThioCyanate
HRP Horse Radish Peroxidase
GaM Goat anti-Mouse antibody
DNP 2,4 dinitro-fluorbenzene (DiNitroPhenyl)
ACim 4-amino-Cinnamic acid
LPR Liquid Permanent Red (Dako K0540)
Sin sinnapinic acid (4-hydroxy-3,5-dimethoxy cinnamic acid)
Caf caffeic acid (3,4-dihydroxy cinnamic acid)
Alpha-CHC apha-ciano-4-hydroxycinnamic acid
PNA-X peptide nucleic acid oligomer (N-(2-aminoethyl)-glycine) comprising different substituents coupled to the central nitrogen
A adenine-9-acetic acid,
C cytosine-1-acetic acid,
D 2,6-diaminopurine-9-acetic acid,
G guanuine-9-acetic acid,
Gs 6-thuioguanine-9-acetic acid,
P 2-pyrimidinone-1 acetic acid,
T thymine-1-acetic acid,
Us 2-thiouracil-1-acetic acid.
Dpr 2,3 diamino-propionic acid,
Phe phenylalanine,
Tyr tyrosine,
Trp tryptophane,
Lys lysine,
Cys cysteine,
betaala betaalanine, N,N diacetic acid
FFPE formaldehyde fixed paraffin embedded
PDQA programmable dot quantitative assay also known as single molecule detection
Cross-linker a first substrate of an enzyme with oxidoreductase activity
Reporter a second substrate with an enzyme with peroxidase activity
RDM Reporter Deposition Medium
BAM Binding Agent Medium Materials and Protocols
 1. Second Substrate (Reporter):
  Sin-Lys(Sin)-Lys(Sin)-L150-Lys(Flu) (0328-018/D21047/D21067)

Synthesis is performed solution phase following solid phase synthesis of intermediates carrying free N-terminal amino groups and free lysine side chains amino groups. Alpha-N-Boc-(epsilon-N-2-Cl-Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

Boc-(Lys(2-Cl-Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M sinnapinic acid (4-hydroxy-3,5-dimethoxy cinnamic acid) in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

Binding Agents:
 2.1. Goat anti-Rabbit antibody conjugated with Dex70 conjugated with HRP (L348.111, fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluted product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%. Assuming direct proportionality between incorporated HRP and Dextran showed that fractions 10-11 contained 10.9 HRPs and 0.96 antibodies per Dextran. Only these two fractions were used for experiments.

2.2. Anti-HER2-antibody conjugated with Dex70 conjugated with HRP (D21100, fractions 9-10)

4.6 nmol 70 kDA MW dextran was reacted with 202 nmol HRP in 125 microliters of buffer A (100 mM NaCl, 25 mM NaHCO$_3$, pH 9.5) for 3 h at 30 C. Thereafter 18 nmol antiHer2 in 489 microL of water was added to the dextran-HRP conjugate and the mixture was allowed to react for further 21 h at 30 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiHer2 and HRP. The product was divided into 4 fractions based on conjugate size: The first two fraction containing product (Frac. 7-8) eluded as a first peak, presumably containing some cross linked conjugates, then followed by a broad shoulder that was divided into fractions 9-10 (homogeneous large conjugates) and fractions 11-19 (smaller variable conjugates) and finally unconjugated enzymes and antibodies in fractions 20-41. Measurements on individual product fractions, as well as fractions containing non-conjugated antibody and HRP, showed a total conjugate recovery of 68%. Assuming direct proportionality between incorporated HRP and Dextran showed that fractions 9-10 contained 9.1 HRPs and 0.6 antibodies per Dextran. Only these two fractions were used for experiments.

2.3. antiFITC antibody conjugated with Dex70 conjugated with HRP (AMM 353-022 fractions 8-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 66 nmol antiFITC in 196 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluted product was a dextran conjugate comprising antiFITC and HRP. The product was divided into 3 fractions based on conjugate size: The first fractions (8-11) containing product eluded as a first peak, then followed by a broad shoulder (smaller variable conjugates, frac. 12-27) and finally unconjugated enzymes and antibodies in fractions 28-45. Measurements on individual product fractions, as well as fractions containing non-conjugated antibody and HRP, showed a total conjugate recovery of 90%. Assuming direct proportionality between incorporated HRP and Dextran showed that fractions 10-11 contained 11.7 HRPs and 0.80 antibodies per Dextran. Only these two fractions were used for experiments.

3. First Substrate

DAB, ferulic acid and alpha-ciano-4-hydroxycinnamic acid (alpha-CHC) were used as the first substrate at the following conditions:

TABLE 1

|  | DAB | Ferulic acid | Alpha-CHC |
| --- | --- | --- | --- |
| Optimal amount (Range) | 0.14 mM (0.1 mM-less than 1 mM) | 1.5 mM (0.5 mM to 5 mM) | 5 mM (1.5 mM and 15 mM) |
| Optimal H$_2$O$_2$ amount | 1.5 mM | 0.9 mM | 0.6 mM |
| Optimal deposition time | 5-10 min | 10-15 min | 10-15 min |
| Optimal second substrate | Contains Fer or Sin | Contains Sin | Contains Fer |
| Dot diameter | 3-4 microns | 3-4 microns | 2-3 microns |

Compared to DAB, dots of a similar diameter with ferulic acid were obtained when incubation time was doubled; with alpha-ciano-4-hydroxycinnamic acid the incubation time was as for DAB, however the dots were smaller (2-3 microns in diameter compared to 3-4 microns for DAB).

4. Other Reagents

DAB chromogen solution (Dako K3465)
LPR chromogen solution (Dako K0640)
Hematoxylin counterstain (Dako S3301)
Wash buffer (Dako S3306)
Target retrieval solution (Dako S1699)
Mounting media Dako Fairmount (S3025)

5. Test Material

As a test material serial sections of pellets of formalin fixed paraffin embedded cell lines sk45, df45, df23 expressing Her2 were used (these cell lines will further be referred to as the 0 (i.e. negative), the 1+ and the 3+ cell line, correspondingly). These cell lines are the 0, 1+ and 3+ control material for FDA approved Dako HercepTest for breast cancer. Pellets of the cell lines were embedded in a single block of paraffin to provide sections where the every cell lines present. The choose of the test material reflects availability of the material (e.g. each single block provides hundreds of serial sections, the presence of three different cell samples on each test slide allows inter correlation between the results of one staining procedure of three different test samples).

6. Pretreatment of Test Material:

Slides with FFPE sections of blocks containing the three cell lines (further referred as "slides") were deparaffinized by emersion in xylene (2×5 min) followed by 96% ethanol (2×2 min) and 70% ethanol (2×2 min). Then, the slides were washed with deionized water and transferred to Target retrieval solution, either the high pH solution (Dako S2375), diluted 10× (examples 1 and 2 with anti cytokeratin) or low pH solution (Dako S1700) (see examples 10.3-10.8 below). The slides were then heated to boiling in a microwave oven (approx 5 min) and gently boiled for 10 min. Afterwards the slides were allowed to cool for min 20 min and then were transferred to a wash buffer (Dako S3006) diluted 10×.

7. Primary Antibodies:

Pan specific anti-cytokeratin antibody (Dako M3515, monoclonal mouse) was used both as concentrate and diluted solution. Antibody dilutions were made based on total protein concentration (indicated on each vial) and considering the molecular weight of the antibody (150 kDa/mol). This antibody is further referred as "anti-cytokeratin".

Anti-Her2 antibody was a monoclonal rabbit antibody (Dako clone 25-11-3). Dilutions were made based on calculated total protein concentration in a concentrated solution and the molecular weight of the antibody of (150 kDa/mol). The antibody is referred herein as "anti-HER2".

8. Media

Binding agent medium (BAM): 0.1% 4-aminoantipurine, 0.2% Procline 2% BSA, 0.2% Casein, 2% PEG, 0.1% Tween20, 0.1 M NaCL, 10 mM HEPES, pH 7.2. (ABCPT-buffer)

Reporter deposition medium (RDM): 50 mM imidazole HCl pH 7.5, 0.1% Nonidet P40, 0.1%, benzalkonium chloride, 0.005% (1.5 mM) hydrogen peroxide.

9. Instruments.

Dako Autostainer Classic. This instrument is a totally open and freely programmable automated IHC instrument where reagents and incubation times can be used and set at will. The instrument performs four basic actions Aspirate reagent.
Blow wash buffer off horizontally placed slide.
Dispense reagent onto slide. (Known as sip and spit.)
Wash a slide by flushing it with wash buffer.

A typical program for a single slide is described below in protocol 1. For all PDQA experiments the initial peroxidase block and the dot forming steps were kept invariable:

10. Staining Protocol 1

Peroxidase block, 5 min in Dako S2023
Wash
Formation of Target Sites:
Primary antibody,
Wash
HRP-Labeled secondary antibody.
Wash.
Formation of reporter deposits at target sites
Incubation of samples (a) 10 minutes with 0.28 mM DAB and 5 pM reporter (D21047) in RDM.
Wash
c) Detection of reporter deposits at single target sites
Anti-FITC-AP, 10 min, 20 nM D20036 in BAM
Wash
LPR, 10 min, Dako K0640
Wash
d) Haemotoxylin counterstain
Haematoxylin, 5 min
Wash with deionized water
f) Mounting Additional washes may be introduced into the automated protocol. The automated scheduler will keep overall protocol time at a minimum, by reducing duration of washing steps to a minimum; however, duration of washing steps will depend on loading of the instrument. If a single slide is programmed to be stained, a single washing step might be reduced to 20 seconds, while a full load of 48 slides significantly increase washing time. To keep this time variation minimal, 10 slides in average were stained in each run. Accordingly, washing step duration was kept approximately 2 min per step. Multiple washes following reporter deposition and incubation of the deposits with anti-FITC-AP assures a minimal LPR background staining. Despite of massive amplification (it is estimated that each red Dots derived from a single antibody-dextran-HRP molecule bound to the target comprise in average 100 billion molecules of LPR) there can virtually no background be detected.

Extra washing might be recommended in order to reach the highest level of amplification and lowest background staining, while reporter and reporter binding agent are used in relative high amounts.

11. Evaluation of Staining

Dot counting was initially performed manually, by visual inspection of PDQA stained slides and their images. Automated image analysis was performed using the freeware JMicrovision vs. 1.27. In an exemplary embodiment, LPR red Dots produced as described and haematoxylin stained nuclei were automatically counted. Automated counts were verified by visual inspection and manual counts. Segmentation and object abstraction could be based on hue alone in Hue, Saturation, Intensity, (HSI) color space, i.e. both intensity and saturation set to full 0-255 range. Dot hue was set to 188(violet)-255 and 0-16 (orange), nuclear hue to 76 (green) to 163 (blue). Dot-nuclear contrast was enhanced by over exposing red (1.2), neutral green (1.0) and under exposure of blue (0.56) during image capture performed on an Olympus BX51 microscope fitted with a DP50 5.5 Mpixel camera and CellD image capture software.

12. Experiments 12.1. Determination of Kd of Anti-Cytokeratin Antibody.

8 slides with FFPE sections 0, 1+ and 3+ cell lines were pretreated and stained as described above (see pretreatment and protocol 1).

The primary antibody (anti-cytokeratin), was applied for 20 min in varying concentrations as described in table 2:

TABLE 2

| Slide number | Concentration of M3115 in BAM |
|---|---|
| 1 | 40 nM |
| 2 | 33 nM |
| 3 | 25 nM |
| 4 | 20 nM |
| 5 | 13 nM |
| 6 | 10 nM |
| 7 | 5 nM |
| 8 | 2.5 nM |

The slides were then mounted with aqueous Faramount. 3 images of each cell line pellet on each slide were captured, red colored dots were manually counted in each image and the number of counted dots was compared to a theoretically calculated number of dots in the samples.

Presuming that one molecule anti-cytokeratin (cAb) is associated with one dot, the theoretical number of dots (Ndot) may be calculated using the following formula:

$$Nd = \frac{[cAb_c] \times Ndot_{max}}{Kd + [cAb]}$$

Wherein [cAb] is the concentration of anti-cytokeratin antibody, and Kd is the dissociation constant of the anti-cytokeratin antibody, i.e. cAb, and $Ndot_{max}$ is a constant.

The constant named $Ndot_{max}$ means maximal number of dots and in the present content means that the number of dots approaches the maximum value when the used concentration of an antibody is significantly above its Kd value, i.e. when the anti-cytokeratin antibody are used in a concentration that is far beyond the Kd value.

This formula is derived from the formula for the dissociation constants for the primary and secondary antibodies with the prerequisite that the absolute concentration of protein in every test sample (i.e. samples of cells 0, 1+ and 3+, 8 slides of each cells line with different concentrations of the antibody as indicated in table 3 below) is constant and the concentration of the secondary antibody is kept unvarying between slides.

Table 3 shows the number of experimentally obtained and theoretically calculated dots for every sample 1-8 for all three test cell lines:

TABLE 3

| Slide | Concentration of primary antibody nM | Dots counted and calculated, total of 3 images in 0 cell line | | Dots counted and calculated, total of 3 images in 1+ cell line | | Dots counted and calculated, total of 3 images in 3+ cell line | |
|---|---|---|---|---|---|---|---|
| | | counted | calculated | counted | calculated | counted | calculated |
| 1 | 2.25 | 165 | 170 | 318 | 316 | 376 | 389 |
| 2 | 5 | 293 | 292 | 445 | 542 | 627 | 667 |
| 3 | 10 | 384 | 411 | 731 | 765 | 879 | 941 |
| 4 | 13.3 | 487 | 458 | 920 | 851 | 1043 | 1048 |
| 5 | 20 | 502 | 518 | 968 | 962 | 1140 | 1185 |
| 6 | 25 | 581 | 547 | 1026 | 1015 | 1333 | 1250 |
| 7 | 30 | 669 | 567 | 1159 | 1054 | 1546 | 1297 |
| 8 | 40 | 629 | 595 | 1269 | 1106 | 1663 | 1361 |

By fitting the curves generated from the formula above to the curves generated from the experimental data, approximate values of Kd1 and $Ndot_{max}$ can be determined. Thus, Kd1 was set to 7 nM, for all three calculated series, $Ndot_{max}$ to 700 (0), 1300 (1+) and 1600 (3+).

A Kd value of 7 nM is in good agreement with experimental count across all three cell lines. In case of the 1+ and 3+ cell lines, calculated values are slightly below measured values for high concentrations of antibody. Anti-cytokeratin antibody M 3515 has a broad specificity and it recognizes several different cytokeratin subtypes. Theoretically, for each cytokeratin subtype the antibody may have a slightly different Kd since the surroundings the antigen may be different and it may influence the antibody binding. This explains a "non-perfect fit" with the hyperbolic curve. Furthermore, that some unspecific binding might take place at concentrations well above the Kd value.

The performed quantification can be considered to be precise because the results from experiments where different slides and different cell lines were used can be directly compared, i.e. dot staining pattern provides an easy and rapid digitalized quantitative evaluation of samples, i.e. by counting the visually distinct dots, e.g. 600 dots are easily distinguishable from 300 dots in another sample.

The Kd value of the used secondary antibody (D20168) is not known, and it has not been shown that an equilibrium is reached in this step of affinity binding, however control experiments did show that further incubation with primary antibody (prolonged incubation time and additional portions of antibodies) did not lead to significant increase in signal. Thus, if a constant fraction of primary antibodies is recognized by the secondary antibody during the experiment, the latter has no influence on the Kd measurement. Using multiple applications of secondary antibodies twice as many dots can be produced. In these applications maximal number of dots per slide ($Ndot_{max}$) is also doubled, but these does not influence measurement the Kd.

12.2. Determination of Kd of a Second Binding Agent (Goat-Anti-Mouse-Dextran-HRP Conjugate (D20168).)

This experiment was performed using conventional IHC stains (Dako Envision system).

Slides were pretreated as described, and subjected to the following staining protocol 2:

Peroxidase block, 5 min
Wash
Anti-Cytokeratin, 20 min in incubation media 1
Wash
HRP-labeled secondary antibody (D20168), 20 min in incubation media 1
Wash
DAB chromogen solution, 10 min
Wash
Haematoxilin stain, 5 min
Wash with water
Wash
Wash with de ionized water.

12 samples of each of the three cell lines (0, 1+ and 3+) were divided in two series, wherein six slides of the first series were incubated with of 2.5 nM anti-cytokeratin antibody and further incubated with 6 different concentrations of D20168 (100 nM, 50 nM, 25 nM, 15 nM, 10 nM and 5 nM), and six slides of the second series were incubated with 10 nM anti-cytokeratin antibody and further incubated with 6 different concentrations of D20168 (100 nM, 50 nM, 25 nM, 15 nM, 10 nM and 5 nM). The slides of both series were than stained with DAB (as chromogen) and Haemotoxilin according to the above protocol.

For all three cell lines staining intensity increased with increasing concentration, but leveled off within the dynamic range of the IHC staining (below a score of 2.5+).

As expected, using a higher concentration of primary antibody resulted in higher intensities of staining. The staining of the slide treated with 2.5 nM anti-cytokeratin and 100 nM D20168 (further referred as slide A) (of each cell line) was compared to the staining of slides with 10 nM anti-cytokeratin (within each cell line). Two independent mock observers were used to estimate the intensity of staining. They found that for all three cell lines the intensity of staining of the slide A was identical to the intensity of staining of the slide treated with 10 nM anti-cytokeratin and 15 nM D20168 (slide B). Because of the reference material was constant (same cell line control slides) and approximately the same staining intensity was observed in slides treated with different amounts of the primary and secondary antibody. it was concluded that the number of Cytokeratin-anti-Cytokeratin-D20168 complexes present in slides A and B (within one cell line) was the same. Accordingly, the following equation could be used to calculate Kd (i.e. Kd2) of the secondary antibody of D20168:

$$Kd2 = \frac{(1-C_3) \times ([Ab2]_1 \times [Ab2]_2)}{(C_3 \times [Ab2]_1) - [Ab2]_2}$$

Wherein $C_1$, $C_2$ and $C_3$; $[Ab1]_1$=2.5 nM, $[Ab1]_2$=10 nM, $[Ab2]_1$=100 nM, $[Ab2]_2$=15 nM, and wherein $C_3$ defined from the following equation:

$$C_3 = \frac{C_2}{C_1} = \frac{(Kd1 + [Ab1]_2) \times [Ab1]_1}{[Ab1]_2 \times (Kd1 + [Ab1]_1)}$$

Thus, Kd2 of D20168 was calculated to be 25 nM.

12.3a. Establishment of Equilibrium Conditions for Primary HER2 Antibody.

Due to a low Kd (i.e. high affinity) value for the HER2 antibody clone tested, initial attempts to determine the Kd value by means similar to example 1 might give results that would not fit well with equilibrium conditions: a single application of a very low concentrations (100 pM) of the primary antibody may lead to formation of incomplete equilibrium. Therefore, in order to defined and secure conditions of the equilibrium conditions for the HER2 antibodies, sequential additions of the primary antibody were applied to the samples of all three lines. Slides treated with the lowest concentration (100 pM) of the antibody, where antibody depletion and incomplete equilibrium problems were expected to be most severe, were as well treated with two sequential additions of high concentrations of the secondary antibody, to compensate depletion in of the primary antibody step.

The staining was done according to protocol 1 with the specific concentrations, incubation times and number of sequential additions for the primary and secondary antibodies, as the following.

100 pM HER2 antibody, 1-6 sequential incubations, 10 minutes each:

TABLE 4

| Slide number | Number of additions |
| --- | --- |
| 1 | 1 |
| 2 | 2 |
| 3 | 3 |
| 4 | 4 |
| 5 | 5 |
| 6 | 6 |

One wash followed each addition (prior to the following addition); 5 pM HRP-Labeled Goat-anti-Rabbit (L348-111 frac. 9-10), two sequential incubations, 10 min each.

Three images (10× magnification) of each 0 and 1+ cell line samples were taken and the number of PDQA dots per nucleus was counted. The 3+ cell line samples were disregarded due to a very intensive staining which did not allow an accurate count the dots. The results are presented in Table 5 below.

TABLE 5

| Additions of anti-HER2 | Dot/nuclei(0) | Dot/nuclei(1+) |
| --- | --- | --- |
| 1 | 0.158 | 0.407 |
| 2 | 0.258 | 0.665 |
| 3 | 0.305 | 1.031 |
| 4 | 0.42 | 1.309 |
| 5 | 0.532 | 1.536 |
| 6 | 0.532 | 1.513 |

From the results of the experiment it was concluded that at least 5 additions of the HER2 primary antibody solution, were the amount of the antibody is 100 pM, is required to avoid depletion and establish true equilibrium condition in the tested samples.

12.3b. Establishment of Equilibrium Conditions for Secondary Antibody.

To define the equilibrium conditions for the secondary antibody, a high concentration of the HER2 primary antibody was used in the first step of the procedure which would expected to give a high level of bound primary antibody to the target, and a series of applications of low concentration of the secondary antibody (L348-111, fractions. 9-10), where depletion of the antibody would be expected to be most sever, was performed in the second step of the procedure.

The staining was done according to protocol 1 with the specific concentrations, incubation times and number of additions for the primary and secondary antibodies described below:

500 pM HER2 antibody, 2 sequential additions, 10 min each;
Wash
−5 pM L348-111, 1-5 sequential additions, 10 min each:

TABLE 6

| Slide number | Number of additions |
|---|---|
| 1 | 1 |
| 2 | 2 |
| 3 | 3 |
| 4 | 4 |
| 5 | 5 |

One wash was applied after each addition, prior to the following addition.

Three images (10× magnification) of each 0 and 1+ cell sample were taken and the number of PDQA dots per nucleus was counted. The 3+ cell line samples were disregarded due to a very intensive staining which did not allow an accurate count the dots.

The results are presented in Table 7:

TABLE 7

| Additions of Secondary antibody | Dots/nucleus (0) | Dot/nucleus (1+) |
|---|---|---|
| 1 | 0.077 | 0.327 |
| 2 | 0.083 | 0.609 |
| 3 | 0.195 | 0.889 |
| 4 | 0.318 | 1.216 |
| 5 | 0.364 | 1.31 |

From the results of the experiment, it was concluded that at least 5 additions of 1.5 pM L348-111 frac. 9-10 was required to reach the equilibrium.

12.3c Determination of the Kd Value of the Anti-HER2.

From examples 12.3a and 12.3b it has been known that 6 sequential additions of 100 pM HER2 antibody and subsequently 5 additions of 5 pM L348-111 were required in order to reach the equilibrium conditions and measure the Kd values. Accordingly, PDQA staining of 12 slides of samples of the tree cell lines was performed according to protocol 1 with the specific concentrations, incubation times and number of additions for the primary and secondary antibodies as described below:

6 concentrations of the HER2 antibody, 6 sequential additions, 10 minutes each:

TABLE 8

| Slide number | Concentration of HER2 |
|---|---|
| 1 and 2 | 100 pM |
| 3 and 4 | 200 pM |
| 5 and 6 | 300 pM |
| 7 and 8 | 400 pM |
| 9 and 10 | 500 pM |
| 11 and 12 | 1 nM |

One wash step was applied after each addition and prior to the following;
5 pM L348-111, 5 sequential additions, 10 min each.

Three images (10× magnification) of samples of each 0 and 1+ cell lines were taken and the number of PDQA dots per nucleus was counted. The 3+ were disregarded due to very intensive staining, likewise, the slides incubated with the highest concentration of the primary antibody (1 nM).

The results of the experiment with samples of the 0 cell line are presented in Table 9:

TABLE 9

| Concentration of Anti-HER2 | Theoretically calculated number of dots Kd 280, max 0.7 dot/nucleus | Dot/nucleus experimentally counted in 0 cell line |
|---|---|---|
| 100 | 0.183246 | 0.186 |
| 200 | 0.290456 | 0.305 |
| 300 | 0.360825 | 0.358 |
| 400 | 0.410557 | 0.416 |
| 500 | 0.44757 | 0.451 |
| 1000 | 0.546022 | 0.69 |

Use of very low concentrations of both primary and secondary antibodies (100-500 pM and 5 pM correspondingly), combined with multiple sequential additions is necessary to reach the equilibrium conditions as demonstrated in experiments 12.3a and 12.3b. The 6 times addition of primary antibody at a concentration well above Kd (1 nM) should led to some background, which is expected, however the fit obtained from the 5 double determinations around Kd is very good. Using an iterative process of adjusting the Kd and the $Ndot_{max}$ of Formula 1 is an alternating way: the data was fitted to a Kd value of 282 pM and a maximum dot count of 0.70 dots per nucleus at (hypothetical) target saturation.

12.3d. Determination of Kd of L348-111 (Goat-Anti-Rabbit-Dextran-HRP conjugate).

This experiment was performed using conventional IHC stains. Slides were pretreated as described, and subjected to the following staining protocol 3:
Peroxidase block, 5 min
Wash
Anti-HER2 in incubation media 1, 6 additions, 10 min each;
Wash
L348-111 in incubation media 1, 3 additions, 10 min each;
Wash
DAB stain, 10 min
Wash
Haematoxilin stain, 5 min
Wash with water
Wash
Wash with de ionized water.

For each of the three cell line, three slides were stained (in triplicate) with 100 pM anti-HER2 and 50 nM L348-111. The other six slides were stained with 500 pM anti-HER2 and with decreasing concentrations of L348-111 (50 nM, 25 nM, 17 nM, 11 nM, 7.5 nM and 5 nM correspondingly). Two independent observes of the staining results found that for all three cell lines the intensity of the triplicate stain (100 pM anti-HER 2 and 50 nM L348-111) was identical to the slide treated with 500 pM anti-HER2 and 11 nM L348-111. As the reference material was constant (same cell line control slides) and a constant staining intensity was observed, it could be concluded that the same number of HER2-anti-HER2-L348-111 complexes were present. Accordingly, the following formula was used to calculate the Kd of the secondary antibody:

$$Kd2 = \frac{(1 - C_3) \times ([Ab2]_1 \times [Ab2]_2)}{(C_3 \times [Ab2]_1) - [Ab2]_2}$$

Wherein $[Ab1]_1$ and $[Ab1]_2$ are two different concentrations of the primary antibody, and $[Ab2]_1$ and $[Ab2]_2$ are different concentrations of the secondary antibody.

Calculating $C_3$ from the following equitation:

$$C_3 = \frac{C_2}{C_1} = \frac{(Kd1 + [Ab1]_2) \times [Ab1]_1}{[Ab1]_2 \times (Kd1 + [Ab1]_1)}$$

And using the values of $[Ab1]_1$=100 pM, $[Ab1]_2$=500 pM, $[Ab2]_1$=50 nM, $[Ab2]_2$=11 nM, Kd2 of L348-111 was found to be equal to 28 nM.

In the equilibrium titration of example 12.3c the results were fitted to 0.70 dots per nucleus (at conditions of saturation with primary antibody and use of L348-111 at 1.5 pM concentration). Accordingly, using the following equation it is possible to calculate the total amount of HER2 (PrTotal) present in 0 cells:

$$PrTotal = [Ab2:Ab1:Pr] \times \frac{Kd1 + [Ab1]}{[Ab1]} \times \frac{Kd2 + [Ab2]}{[Ab2]}$$

[Ab2:Ab1:Pr] is the concentration of complexes HER2-anti-HER2-L348-111, Kd1 is the constant dissociation of anti-HER2, and Kd2 is the constant dissociation of L348-111, $[Ab1]_1$ and $[Ab1]_2$ two different concentrations of the anti-HER 2, and $[Ab2]_1$ and $[Ab2]_2$ are two different concentrations of L348-111.

Setting [Ab2:Ab1:Pr] at 0.70 PDQA dots/nucleus, the first fraction to 1 and Kd2 to 28 nM and [Ab2] to 1.5 pM, the value of PrTotal is calculated to be 13.000 molecules/nucleus.

This value is in a good agreement with the data of the field that the 0 i.e. negative cell line express 21,600±6700 copies of the Her2 receptor on the surface of these cells.

Example 2. Quantification of a Target in a Histological Sample (Method II)

The method (II) for estimation of the total (absolute) number of target molecules in cells has a number of similar approaches compared to the method (I), however it has also some differences.

In the previously described method equilibrium conditions should be established for both primary antibody and labeled secondary antibody. In case of high target concentrations this may present a difficulty as depletion of binding agents during incubations will occur and it will thus require multiple and prolonged incubations with the binding agents. The present method utilizes that using very high concentration of binding agents a "top" level of binding (which means that essentially all binding sites in the sample will be saturated with the corresponding binding agent) can be established without having the depletion problems. Evidently never 100%, but 90-99% binding of a protein target with a high affinity primary antibody, and 50-75% binding of the primary antibody with labeled secondary antibody may be reached. Within these ranges, experiments with a varying but high concentration of reagents can be used to establish more precise binding levels.

Further, using a mixture containing a high concentration of unlabeled secondary antibody and low concentration of labeled (the same) secondary antibody, equilibrium conditions can be reached, while only a small fraction of the primary antibodies bound to the target will be labeled.

The present method further utilizes the possibility provided by the present visualization method that labeled secondary antibody may be visualized in several ways, depending on degree of amplification. In case of low amounts of the target bound primary antibody, a labeled secondary (or a mixture of labeled and unlabeled) antibody can be used to produce countable dots. In case of high amounts of the target bound primary antibody, the same reagent (or mixture) can be used to produce a conventional stain. The experiment thus may comprise several steps:

Incubations with high concentrations of binding agents are used to establish equilibrium conditions leading to recognition of a high and known fraction of targets. Such experiments are carried out with both primary and labeled secondary antibody. Such conditions will further be referred as "top level" conditions.

Then, a mixture of labeled secondary and unlabeled secondary antibody that recognizes an unknown fraction of primary antibodies is prepared and used for incubation of a tissue sample with a high target expression that has been treated with a primary antibody at the top level conditions. The incubation is followed by visualization of the bound labeled secondary antibody with a conventional stain.

Using conventional staining, titration of the target bound primary antibody by the labeled secondary antibody at the top level conditions is performed. The important point is that equilibrium conditions need not be established between the target and the primary antibody. It is sufficient that using constant test material (the constant test material refers to a test material wherein the amount of the target is constant), a reproducible amount of the target is recognized. At some low concentration of primary antibody, a staining intensity is obtained that is identical to the level of staining that observed in step 2.

Using a method for visualizing single molecules as dots (as described in the present invention), a mixture of labeled and unlabeled secondary antibody is used to access a fraction of the target recognized by the same low concentration of the primary antibody as in step 3, relative to the fraction of the target recognized by the top level conditions of primary antibody.

Using the low level of primary antibody as of step 3, and the mixture of labeled and unlabeled secondary antibody as of step 2, single molecules are stained as dots and the number of dots per nucleus is evaluated.

From these experiments, the absolute number of targets can be determined. From experiments of steps 1 and 4, it is known which fraction of the target is recognized by the low concentration of the primary antibody. From experiments of steps 1 and 3, it is possible to deduce which fraction of the primary antibodies is recognized by the mixture of labeled and unlabeled secondary antibody used in experiment 2. We use the fact that the identical conventional staining levels are obtained in experiments of step 2 and 3 (which means that there is the identical number of the bound labeled secondary antibodies in the samples). Thus, we now know both the fraction of the target molecules recognized by the low concentration of the primary antibody, and the fraction of the primary antibodies recognized by the mixture of labeled and unlabeled secondary antibody of experiment in step 5. Multiplying these two factors gives the fraction of target molecules visualized as. dots (see description of experiment 2.1c below). As we further have counted the number of dots per nucleus, we know the number of target molecules present per nucleus. Thus, an absolute count has been performed.

Experiments

Materials and methods used in the following experiments, if not specifically disclosed, are as described above.

It is established that the Kd of the primary anti-Her2 antibody is 280 pM. (See experiment 12.3c) Using the antibody under equilibrium conditions (multiple additions until no further increase in signal is observed) at a concentration of 13.3 nM will result in labeling of 13.3 nM/(13.3 nM+0.28 nM) which is equal to approximately 97.9% of the primary target molecules.

Likewise, it is established that the Kd of the labeled secondary antibody is 28 nM. (See experiment 12.3d). Using the labeled secondary antibody under equilibrium conditions (multiple additions until no further increase in signal is observed) at a concentration of 25 nM will result in labeling of 25 nM/(25 nM+28 nM) which is equal to approximately 47.1% of the bound primary antibodies.

Experiment 2.1a

A constant test material was used serial sections of pellets of formalin fixed paraffin embedded cell lines. The cell lines used were 3+ control material from Dako HercepTest.

Slides with FFPE sections of blocks containing the cell lines, from now on referred to as "slides" were de paraffinized by emersion in xylene (2×5 min) followed by 96% ethanol (2×2 min) and 70% ethanol (2×2 min). The slides were washed with de ionized water and transferred to low pH target retrieval solution (Dako S1700). The slides were then heated to boiling in a microwave oven (approx 5 min) and then gently boiled for 10 min. The slides were allowed to cool for min 20 min before being transferred to wash buffer, Dako S 2343.

The slides were then stained on the Autostainer using the following protocol:
Peroxidase block, Dako S2023, 5 min
Wash
Several sequential 10 minute additions of 13.3 nM anti-HER2 primary antibody
Wash
Several sequential 10 minute additions of 100 pM Goat-anti-Rabbit-Dextran-HRP (L348.111) mixed with 5 nM unlabelled Goat-anti-Rabbit.
Wash
DAB (Dako K5007), 10 min
Wash
Haematoxylin (Dako S3301), 5 min
Wash with water
Wash
Results:
Three 10 minute additions of 13.3 nM antiHER2 were sufficient to reach equilibrium conditions. A fourth addition did not lead to increased staining level. Two 10 minute additions of 100 pM Goat-anti-Rabbit-Dextran-HRP (L348.111) mixed with 5 nM unlabelled Goat-anti-Rabbit was sufficient to reach equilibrium conditions. A third addition did not lead to increased staining level. The maximum staining level reached corresponded to approx. 1+. (Although this cell line is referred to as 3+, the use of low concentration of labeled secondary antibody mixed with a high concentration of unlabeled secondary antibody leads to labeling of a small fraction of primary antibodies).

Experiment 2.1b

Slides were pretreated as in experiment 2.1a, and subjected to the following protocol (conventional DAB staining):
Peroxidase block, Dako S2023, 5 min
Wash
10 minutes anti-HER2 primary antibody in varying concentration in the range 30 to 50 pM.
Wash
Two sequential 10 minute additions of 25 nM Goat-anti-Rabbit-Dextran-HRP (L348.111). A control slide showed that a third addition did not lead to increased signal.
Wash
DAB (Dako K5007), 10 min
Wash
Haematoxylin (Dako S3301), 5 min
Wash with water
Wash
Results:
An incubation with 40 pM anti-HER2 for 10 minutes resulted in a staining intensity (1+) identical to the maximum staining level reached in experiment 2.1a. The 43 pM incubation resulted in a visibly higher staining intensity, whereas the 37 pM incubation gave a visibly lower staining intensity.

Experiment 2.1c

The slides were pretreated as in experiment 2.1a and subjected to the following protocol (PDQA staining):
Peroxidase block, 5 min with Dako S2023
Wash
AntiHER2 primary antibody. Either 3 sequential 10 minute additions of 13.3 nM (slide 1) or one 10 minute addition of 40 pM (Slide 2-5)
Wash
Two sequential 10 minute additions of 500 femtoM Goat-anti-Rabbit-Dextran-HRP (L348.111) mixed with 5 nM unlabelled Goat-anti-Rabbit (slide 1-3) or two sequential 10 minute additions of 100 pM Goat-anti-Rabbit-Dextran-HRP (L348.111) mixed with 5 nM unlabelled Goat-anti-Rabbit (slides 4-5)
Wash
FITC-Reporter deposit: 10 min with incubation media 2 with 0.28 mM DAB and 10 microM D21067.
Three washes
Anti-FITC-AP: 10 min incubation, 20 nM D20036 in BAM
Three washes
LPR 10 min with Dako K0640
wash
Haematoxylin (Dako S3301), 5 min
Wash with water
Wash The slides were subjected to image analysis. Images of the entire cell pellets were captured at 20× (approx. 300×300 nm pixels) using a ScanScope (Aperio) slide scanner. The images were analyzed using JMicrovision vs. 1.27 software. Red dots were identified in Intensity, Hue, Saturation color space as (I=0-234, H=187-37, S=52-255), blue nuclei were identified as (I=0-201, H=148-221, S=0-190). A size threshold was further applied to dots, objects bigger than 30 pixels were counted as two dots, objects bigger than 45 pixels were counted as three dots. A lower threshold of 100 pixels was applied to nuclei to filter away debris and smaller fragments of nuclei.

Note that the partially overlapping color spaces allow identifying individual pixels as both part of a red dot and as part of a nucleus, consistent with the dark violet appearance of dots on top of nuclei.

Results and Conclusions:

Results of the PDQA staining of slides and dot calculation are shown in the Table 10 below:

TABLE 10

| Slide | Dots | Nuclei | Dots/nucleus |
|---|---|---|---|
| 1 | 56918 | 12388 | 4.59 |
| 2 | 151 | 13817 | 0.0109 |
| 3 | 177 | 13925 | 0.0127 |
| 4 | 52011 | 13618 | 3.82 |
| 5 | 61040 | 12939 | 4.72 |

Comparison of slide 1 to the average of slides 2 and 3 shows 388 times less bound primary antibody. As slide 1 represents around 97.9% (the value is derived from Kd1 of anti-Her2) of bound target molecules, application of 40 pM primary antibody for 10 minutes on the same test material (slides 2 and 3) gives rise to 1 in 396 target molecules being bound to the primary antibody (or 0.252%).

This data was then used to analyze the results of experiments 2.1a and 2.1b. As mentioned, application of 40 pM primary antibody for 10 minutes results in labeling of 0.252% of the primary target. Subsequently, binding 47.1% (the value is derived from Kd of the secondary antibody) of the bound to the target primary antibodies to the secondary antibody results in 0.119% of the target being (indirectly) bound to the secondary antibody. This corresponds to experiment 2.1c, i.e. using 40 pM primary antibody for 10 min. This must also be the case (as staining levels are identical) for experiment 2.1b, where the 13.3 nM primary antibody incubation (97.9% of primary targets bound) was followed by the incubation with the mixture of 100 pM labeled secondary antibody with 5 nM unlabeled secondary antibody. Thus, it can be concluded that the use of this mixture leads to 0.119%/0.979=0.121% of the primary antibodies being bound to the labeled secondary; 0.121% of 0.252% of the target is equal to 3.06 ppm (parts per million). Accordingly, the 4.27 dots (in average) per nucleus observed in slides 4 and 5 count to 1.395.000 target molecule per nucleus (this follows from the following calculation: 4.27/ 0.00000306=1.395.000).

The precision of this evaluation can be made by comparing slide 2 and 3 with slides 4-5. There were observed 362 times more dots (in average) using the mixture with 100 pM labeled secondary (slides 2-3) antibody than with 500 fM (slides 4-5). As the mixture with 100 pM results in 0.121% primary antibodies being labeled, the mixture with 500 fM must lead to 362 times lower labeling the target with antibody, i.e. 0.121%/362=3.34 ppm. Using this figure to analyze slide 1 it can be calculated the level of labeling of target molecules in this slide: 97.9% of 3.34 ppm gives 3.27 ppm, and the observed 4.59 dots per nucleus corresponds to 1.402.000 target molecules per nucleus (4.59/ 0.00000327=1.402.000).

Many modifications and variations of this invention can be made without departing from its spirit and scope, as will be apparent to those skilled in the art. The specific embodiments and combinations of embodiments described herein are offered by way of example only and are not meant to be limiting in any way. It is intended that the specification and examples be considered as exemplary only, with a true scope and spirit of the invention being indicated by the following claims.

What is claimed is:

1. A method of optically quantifying expression of at least one target molecule in at least one region of interest of a specimen comprising:
producing optically recognizable dots at sites of the specimen wherein one dot corresponds to a single immunohistochemical binding agent bound to a single target molecule,
wherein the dots are characterized by in-situ programmable features of size and shape and at least one additional programmable optical feature,
wherein the number of dots produced at the sites within a given region are representative of a fractional subpopulation of a total population of target molecules within that region;
imaging the specimen;
selecting at least one region of interest within the image;
recognizing at least one dot within the at least one region of interest and;
quantifying the dots within the at least one region of interest.

2. The method of claim 1, further comprising assessing the expression of target molecules within the at least one region of interest.

3. The method of claim 1, wherein the at least one region of interest includes the entire specimen.

4. The method of claim 1, wherein the number of dots produced at the sites within a given region is representative of a localized expression of the target molecule present within the region.

5. The method of claim 1, wherein the recognizing and quantifying steps are performed across the entire region of interest without performing a background separation step.

6. The method of claim 1, wherein the at least one additional programmable optical feature includes at least one of fluorescence, diffraction level, sharpness, hue, intensity, and saturation.

7. The method of claim 1, wherein quantifying the dots includes at least one of counting the dots, measuring a total area of the dots, calculating a density of the dots in a unit area.

8. The method of claim 1, wherein quantifying the dots includes calculating statistical measures of the predetermined optical features of recognized candidate dots; comparing the optical features of a candidate object with the calculated statistical measures; and adjusting a dot count based at least in part on the results of the comparing step.

9. The method of claim 1, wherein the programmable feature of shape includes at least one of sphericity, eccentricity, compactness, elongation, min to max feret ratio, roundness, and concentric-ringedness.

10. The method of claim 1, wherein the programmable feature of size includes at least one of length, width, diameter, and area.

11. The method of claim 1, wherein the region of interest is selected prior to the quantifying step.

12. The method of claim 1, wherein the step of producing optically recognizable dots is performed using an enzyme-labeled molecular probe detection system.

13. The method of claim 1, wherein the step of producing optically recognizable dots comprises chromogenic staining.

14. The method of claim 1, wherein the step of producing optically recognizable dots comprises fluorescence staining.

15. The method of claim 1, wherein at least a percentage of the dots chosen from 70%, 80%, or 90% are capable of being optically recognized at a specified magnification when imaged at two different focus plane depths within the specimen, and wherein the two focus plane depths are separated by a distance that is at least a distance chosen from 10%, 20%, or 50% of the thickness of the specimen.

16. The method of claim 1, wherein imaging the specimen comprises producing an image of the specimen at a resolution within a range in microns per pixel chosen from 0.6 to 0.9, 0.9 to 1.2, 1.2 to 2.5, or 2.5 to 5 and at least 90% of the produced dots are capable of being optically recognized at the chosen resolution.

17. The method of claim 1, wherein imaging the specimen comprises producing an image of the specimen at a resolution of less than 1 micron per pixel, and at least a percentage of the produced dots chosen from 70%, 80%, or 90% are capable of being optically recognized at the resolution.

18. The method of claim 1, wherein recognizing at least one dot includes identifying dot origins of at least two dots; and
quantifying the at least one dot includes calculating at least one factor based on at least one distance measured between two dot origins.

19. The method of claim 1, wherein a total time to produce the optically recognizable dots is less than 100 minutes.

20. The method of claim 1, wherein producing the dots is carried out at a substantially fixed temperature.

21. The method of claim 20, wherein the substantially fixed temperature is less than 30 degrees C.

22. A system for optically quantifying expression of at least one target molecule in at least one region of interest in a specimen comprising:
a first kit for detecting a fractional sub-population of the at least one target molecule in the specimen;
a second kit for producing optically recognizable dots at sites of the specimen wherein one dot corresponds to a single immunohistochemical binding agent bound to a single target molecule,
wherein the dots are characterized by in-situ programmable features of size and shape and at least one additional programmable optical feature,
wherein the number of dots produced at the sites within a given region are representative of a fractional sub-population of a total population of target molecules within that region.

23. The system according to claim 22, further comprising a stainer adapted to execute a staining protocol using the first and second kits;
an imager adapted to image the specimen; and
a processor configured to:
recognize at least one dot within the at least one region of interest and;
quantify the dots within the at least one region of interest.

24. The system according to claim 22, wherein the first kit comprises a first binding agent and a predetermined portion of the first binding agent comprises a label; and
the second kit comprises a substrate including a staining precipitate.

25. The system according to claim 23, wherein the processor is further configured to assess the expression of target molecules within the at least one region of interest.

26. The system according to claim 23, wherein the at least one region of interest includes the entire specimen.

27. The system according to claim 22, wherein the number of dots produced at the sites within a given region is representative of a localized expression of the target molecule present within the region.

28. The system according to claim 23, wherein the processor is further configured to quantify the dots across the entire region of interest without performing a background separation step.

29. The system according to claim 22, wherein the at least one additional programmable optical feature includes at least one of fluorescence, diffraction level, sharpness, hue, intensity, and saturation.

30. The system according to claim 23, wherein the processor configured to quantify the dots is further configured to perform at least one of counting the dots, measuring a total area of the dots, calculating a density of the dots in a unit area.

31. The system according to claim 23, wherein the processor configured to quantify the dots is further configured to calculate statistical measures of the predetermined optical features of recognized candidate dots; compare the optical features of a candidate object with the calculated statistical measures; and adjust a dot count based at least in part on the results of the comparison.

32. The system according to claim 22, wherein the programmable feature of shape includes at least one of sphericity, eccentricity, compactness, elongation, min to max feret ratio, roundness, and concentric-ringedness.

33. The system according to claim 22, wherein the programmable feature of size includes at least one of length, width, diameter, and area.

34. The system according to claim 24, wherein the label of the first kit is an enzyme.

35. The system according to claim 23, wherein at least a percentage of the dots chosen from 70%, 80%, or 90% are capable of being optically recognized at a specified magnification when imaged at two different focus plane depths within the specimen, and wherein the two focus plane depths are separated by a distance that is at least a distance chosen from 10%, 20%, or 50% of the thickness of the specimen.

36. The system according to claim 23, wherein the imager is adapted to produce an image of the specimen at a resolution within a range in microns per pixel chosen from 0.6 to 0.9, 0.9 to 1.2, 1.2 to 2.5, or 2.5 to 5 and at least 90% of the produced dots are capable of being optically recognized at the chosen resolution.

37. The system according to claim 23, wherein the imager is adapted to produce an image of the specimen at a resolution of less than 1 micron per pixel, and at least a percentage of the produced dots chosen from 70%, 80%, or 90% are capable of being optically recognized at the resolution.

38. The system according to claim 23, wherein the processor is further configured to
identify dot origins of at least two dots; and
quantify at least one dot based on at least one distance measured between two dot origins.

39. The system according to claim 22, wherein the first kit and the second kit are adapted to detect the target molecules and produce the optically recognizable dots in less than 100 minutes.

40. The system according to claim 22, wherein the first kit and the second kit are adapted to detect the target molecules and produce the optically recognizable dots at a substantially fixed temperature.

41. The system according to claim 40, wherein the substantially fixed temperature is less than 30 degrees C.

42. A method of optically quantifying expression of at least one target molecule in at least one region of interest in a specimen comprising:

producing optically recognizable dots at sites of the specimen wherein at least one dot corresponds to a single immunohistochemical binding agent bound to a single target molecule, wherein the dots are characterized by in-situ programmable features of size and shape and at least one additional programmable optical feature, wherein the number of dots produced at the sites within a given region are representative of a fractional sub-population of a total population of target molecules within that region;

wherein each dot is representative of a predetermined number of target molecules to within predetermined statistical limits;

imaging the specimen;

selecting the at least one region of interest within the image;

recognizing at least one dot within the at least one region of interest; and quantifying the dots within the at least one region of interest.

43. The method according to claim 42, further comprising assessing the expression of target molecules within the at least one region of interest.

44. The method according to claim 42, wherein the number of dots produced at the sites within a given region is representative of a localized expression of the target molecule present within the region.

45. The method according to claim 42, wherein producing the optically recognizable dots comprises
detecting substantially all target molecules within the specimen with a first binding agent;
wherein the number of target molecules represented by each dot is determined by a predetermined portion of the first binding agent that comprises a label.

46. The method according to claim 45, wherein the label is an enzyme.

47. The method according to claim 45, wherein the portion of first binding agent that comprises a label is proportional to the number of target molecules represented by each dot.

48. The method according to claim 43, wherein quantifying the dots comprises calculating a dot density.

49. A system for optically quantifying expression of at least one target molecule in at least one region of interest in a specimen comprising:
a first kit for detecting a fractional sub-population of the at least one target molecule in the specimen; and
a second kit for producing optically recognizable dots at sites of the specimen wherein one dot corresponds to a single immunohistochemical binding agent bound to a single target molecule, wherein the dots are characterized by in-situ programmable features of size and shape and at least one additional programmable optical feature, wherein the number of dots produced at the sites within a given region are representative of a fractional sub-population of a total population of the at least one target molecule within that region; and wherein each dot is representative of a predetermined number of target molecules to within predetermined statistical limits.

50. The system according to claim 49, further comprising
a stainer adapted to execute a staining protocol using the first and second kits;
an imager adapted to image the specimen; and
a processor configured to:
recognize at least one dot within the at least one region of interest; and
quantify the dots within the at least one region of interest.

51. The system according to claim 50, wherein the processor is further configured to assess the expression of target molecules within the at least one region of interest.

52. The system according to claim 49, wherein the number of dots produced at the sites within a given region is representative of a localized expression of the target molecule present within the region.

53. The system according to claim 49, wherein the first kit comprises a first binding agent and a predetermined portion of the first binding agent comprises a label;
wherein the predetermined portion of the first binding agent comprising a label determines the number of target molecules that each dot is representative of;
wherein the second kit comprises a substrate including a staining precipitate.

54. The system according to claim 53, wherein the label is an enzyme.

55. The system according to claim 53, wherein the portion of the first binding agent that comprises a label is proportional to the number of target molecules represented by each dot.

56. The system according to claim 50, wherein the processor configured to quantify optically recognizable dots is further configured to calculate a dot density.

* * * * *

UNITED STATES PATENT AND TRADEMARK OFFICE
CERTIFICATE OF CORRECTION

PATENT NO. : 9,970,874 B2
APPLICATION NO. : 13/306470
DATED : May 15, 2018
INVENTOR(S) : Jesper Lohse et al.

It is certified that error appears in the above-identified patent and that said Letters Patent is hereby corrected as shown below:

In the Specification

In Column 4, Line 57, after "software" insert -- . --.

In Column 5, Line 7, after "dots" insert -- . --.

In Column 11, Line 31, delete "330 . . ." and insert -- 330. --, therefor.

In Column 11, Line 55, delete "benzadine" and insert -- benzidine --, therefor.

In Column 12, Line 27, delete "convention" and insert -- conventional --, therefor.

In Column 22, Line 3, after "order" insert -- . --.

In Column 22, Line 58, after "present" insert -- . --.

In Column 24, Line 56, delete "red . . ." and insert -- red. --, therefor.

In Column 32, Line 45, delete ".from" and insert -- from --, therefor.

In Column 36, Line 27, delete "a an" and insert -- an --, therefor.

In Column 40, Line 14, delete "soyabean" and insert -- soybean --, therefor.

In Column 42, Line 23, delete "a an" and insert -- an --, therefor.

In Column 45, Line 27, after "nm" insert -- . --.

In Column 45, Line 31, delete "heretoatoms," and insert -- heteroatoms, --, therefor.

Signed and Sealed this
Eighteenth Day of June, 2019

Andrei Iancu
*Director of the United States Patent and Trademark Office*

CERTIFICATE OF CORRECTION (continued)
U.S. Pat. No. 9,970,874 B2

In Column 45, Line 50, delete "chomogenic," and insert -- chromogenic, --, therefor.

In Column 46, Line 11, after "atoms" insert -- . --.

In Column 46, Line 31, after "150" insert -- . --.

In Column 47, Line 33, delete "6-8,7-9," and insert -- 6-8, 7-9, --, therefor.

In Column 47, Line 14, delete "sinappinic" and insert -- sinapinic --, therefor.

In Column 48, Line 9, delete "thereof." and insert -- thereof, --, therefor.

In Column 48, Line 31, delete "cystein," and insert -- cysteine, --, therefor.

In Column 48, Line 42, delete "non-polimeric" and insert -- non-polymeric --, therefor.

In Column 48, Line 49, delete "cystein," and insert -- cysteine, --, therefor.

In Column 48, Line 50, delete "non-polimeric" and insert -- non-polymeric --, therefor.

In Column 49, Line 53, delete "digoxiginin," and insert -- digoxigenin, --, therefor.

In Column 49, Lines 54-55, delete "acetylaminoflurene," and insert -- acetylaminofluorene, --, therefor.

In Column 49, Line 55, delete "trintrophonol," and insert -- trinitrophenol, --, therefor.

In Column 49, Line 60, delete "zink" and insert -- zinc --, therefor.

In Column 51, Line 53, delete "cellolosics" and insert -- cellulosics --, therefor.

In Column 52, Line 1, delete "polyethyl-" and insert -- poly(ethyl- --, therefor.

In Column 52, Line 56, delete "cabodiimide." and insert -- carbodiimide. --, therefor.

In Column 53, Line 39, delete "equipment" and insert -- equipment. --, therefor.

In Column 54, Line 18, delete "pyrolidone" and insert -- pyrrolidone --, therefor.

In Column 54, Line 25, delete "polyethylenglycol-p-isooctyphenyl" and insert -- polyethyleneglycol-p-isooctylphenyl --, therefor.

In Column 54, Line 26, delete "(NP-40))" and insert -- (NP-40) --, therefor.

In Column 54, Line 30, delete "5%/v/v" and insert -- 5% v/v --, therefor.

CERTIFICATE OF CORRECTION (continued)
U.S. Pat. No. 9,970,874 B2

In Column 54, Line 44, delete "Denhard's" and insert -- Denhardt's --, therefor.

In Column 55, Line 33, delete ".from" and insert -- from --, therefor.

In Column 56, Line 57, delete "pyrolidone" and insert -- pyrrolidone --, therefor.

In Column 57, Lines 9-10, delete "polyethylenglycol-p-isooctyphenyl" and insert -- polyethyleneglycol-p-isooctylphenyl --, therefor.

In Column 57, Line 35, delete "1.5." and insert -- 1.5 --, therefor.

In Column 58, Line 27, delete "azid," and insert -- azide, --, therefor.

In Column 58, Line 44, delete "phosphotase" and insert -- phosphatase --, therefor.

In Column 60, Line 22, delete "discrete" and insert -- discrete. --, therefor.

In Column 62, Line 23, delete "fluorofore" and insert -- fluorophore --, therefor.

In Column 62, Line 26, delete "fluorofore" and insert -- fluorophore --, therefor.

In Column 62, Line 27, delete "fluorofore" and insert -- fluorophore --, therefor.

In Column 63, Line 36, delete "phosphotase" and insert -- phosphatase --, therefor.

In Column 63, Line 61, delete "en" and insert -- an --, therefor.

In Column 69, Line 55, delete "[Ab2]$_1$:" and insert -- [Ab2]$_1$; --, therefor.

In Column 70, Line 14, delete "Pyrolidon" and insert -- Pyrrolidone --, therefor.

In Column 70, Line 17, delete "DiIsopropyl" and insert -- DiIsopropyl --, therefor.

In Column 70, Line 21, delete "TriFluor" and insert -- TriFluoro --, therefor.

In Column 70, Line 31, delete "FlouresceinlsoThioCyanate" and insert -- FluoresceinIsoThioCyanate --, therefor.

In Column 70, Line 37, delete "sinnapinic" and insert -- sinapinic --, therefor.

In Column 70, Line 40, delete "apha-ciano-" and insert -- alpha-cyano --, therefor.

In Column 70, Line 47, delete "guanuine" and insert -- guanine --, therefor.

In Column 70, Line 48, delete "6-thuioguanine" and insert -- 6-thioguanine --, therefor.

CERTIFICATE OF CORRECTION (continued)
U.S. Pat. No. 9,970,874 B2

In Column 71, Line 22, delete "sinnapinic" and insert -- sinapinic --, therefor.

In Column 71, Line 46, delete "cystein" and insert -- cysteine --, therefor.

In Column 72, Line 5, delete "cystein" and insert -- cysteine --, therefor.

In Column 72, Line 33, delete "cystein" and insert -- cysteine --, therefor.

In Column 72, Line 51, delete "-ciano-" and insert -- -cyano- --, therefor.

In Column 73, Line 3, delete "-ciano-" and insert -- -cyano- --, therefor.

In Column 74, Line 20, delete "pM" and insert -- μM --, therefor.

In Column 74, Line 27, delete "Haemotoxylin" and insert -- Haematoxylin --, therefor.

In Column 77, Line 10, delete "Haematoxilin" and insert -- Haematoxylin --, therefor.

In Column 77, Line 23, delete "Haematoxilin" and insert -- Haematoxylin --, therefor.

In Column 77, Line 42, delete "it" and insert -- It --, therefor.

In Column 80, Line 43, delete "Haematoxilin" and insert -- Haematoxylin --, therefor.

In Column 82, Line 63, delete "dots" and insert -- Dots --, therefor.

In the Claims

In Column 89, Line 2, in Claim 42, after "wherein" delete "at least".